US008673458B2

(12) United States Patent
Kwong

(10) Patent No.: US 8,673,458 B2
(45) Date of Patent: Mar. 18, 2014

(54) DELAYED FLUORESCENCE OLED

(75) Inventor: Raymond C. Kwong, Plainsboro, NJ (US)

(73) Assignee: Universal Display Corporation, Ewing, NJ (US)

( * ) Notice: Subject to any disclaimer, the term of this patent is extended or adjusted under 35 U.S.C. 154(b) by 508 days.

(21) Appl. No.: 12/901,871

(22) Filed: Oct. 11, 2010

(65) Prior Publication Data

US 2011/0304262 A1 Dec. 15, 2011

Related U.S. Application Data

(60) Provisional application No. 61/397,516, filed on Jun. 11, 2010.

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/E51.044; 546/10

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,051,569 | A | 9/1991 | Tsuruoka et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,515,298 | B2 | 2/2003 | Forrest et al. |
| 6,528,187 | B1 | 3/2003 | Okada |
| 6,687,266 | B1 | 2/2004 | Ma et al. |
| 6,836,469 | B1 | 12/2004 | Wu |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2001/0019782 | A1* | 9/2001 | Igarashi et al. ............... 428/690 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0073359 | A1 | 4/2006 | Ise et al. |
| 2006/0094875 | A1 | 5/2006 | Itoh et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2007/0278939 | A1 | 12/2007 | Tsuboyama et al. |

(Continued)

FOREIGN PATENT DOCUMENTS

| | | | | |
|---|---|---|---|---|
| EP | 0650955 | | 5/1995 | |
| EP | 1049117 | A2 * | 11/2000 | ............... H01G 9/20 |

(Continued)

OTHER PUBLICATIONS

English language machine translation of JP 2005/298483 A, 2005.*
Nguyen et al., "Gold(I) and Platinum(II) Tetracenes and Tetracenyldiacetylides: Structural and Fluorescence Color Changes Induced by σ-Metalation" Organometallics 2010, 29, 2422-2429.
Search Report corresponding to the PCT/US2011/040038 application.
Jose Ruiz et al: "New Pall adi um(II) and 1-5, Platinum(II) Complexes with 7-16, 9-Aminoacridine: Structures, Luminiscence, 20-25, Theoretical Calculations, and Antitumor 27-36, Activity", 38-41, Inorganic Chemistry, vol. 47, No. 15, Aug. 1, 2008, pp. 6990-7001.
L Monso Scolaro: "Geometrical configuration of monomethyl-platinum(II) complexes driven by the size of entering nitrogen ligands", Inorganica Chimica Acta, vol. 330, No. 1, Mar. 13, 2002, pp. 189-196.

(Continued)

*Primary Examiner* — Michael H Wilson
(74) *Attorney, Agent, or Firm* — Duane Morris LLP

(57) ABSTRACT

Novel organic compounds comprising a substituted anthracene or acridine ligand are provided. In particular, the compound includes an anthracene ligand substituted at the 9 and 10 positions. The compound may be used in organic light emitting devices to provide devices having improved efficiency and lifetime. In particular, these compounds may be especially beneficial for use in blue-emitting OLEDs.

27 Claims, 3 Drawing Sheets

(56) References Cited

U.S. PATENT DOCUMENTS

| | | | |
|---|---|---|---|
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0153034 | A1 | 6/2009 | Lin et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |

FOREIGN PATENT DOCUMENTS

| | | | |
|---|---|---|---|
| EP | 1725079 | 11/2006 | |
| EP | 2034538 | 3/2009 | |
| JP | 200511610 | 1/2005 | |
| JP | 2005/298483 A * | 10/2005 | .............. C07F 15/00 |
| JP | 2006282965 | 10/2006 | |
| JP | 2007123392 | 5/2007 | |
| JP | 2007254297 | 10/2007 | |
| JP | 2008074939 | 10/2009 | |
| WO | WO 0139234 | 5/2001 | |
| WO | WO 0202714 | 1/2002 | |
| WO | WO 0215645 | 2/2002 | |
| WO | WO 03040257 | 5/2003 | |
| WO | WO 03060956 | 7/2003 | |
| WO | WO 2004093207 | 10/2004 | |
| WO | WO 2004107822 | 12/2004 | |
| WO | WO 2005014551 | 2/2005 | |
| WO | WO 2005030900 | 4/2005 | |
| WO | WO 2005089025 | 9/2005 | |
| WO | WO 2005123873 | 12/2005 | |
| WO | WO 2006009024 | 1/2006 | |
| WO | WO 2005019373 | 3/2006 | |
| WO | WO 2006072002 | 7/2006 | |
| WO | WO 2006056418 | 8/2006 | |
| WO | WO 2006082742 | 8/2006 | |
| WO | WO 2006098120 | 9/2006 | |
| WO | WO 2006100298 | 9/2006 | |
| WO | WO 2006103874 | 10/2006 | |
| WO | WO 2006114966 | 11/2006 | |
| WO | WO 2006132173 | 12/2006 | |
| WO | WO 2007002683 | 1/2007 | |
| WO | WO 2007004380 | 1/2007 | |
| WO | WO 2007063754 | 6/2007 | |
| WO | WO 2007063796 | 6/2007 | |
| WO | WO 2008101842 | 8/2008 | |
| WO | WO 2008132085 | 11/2008 | |
| WO | WO 2008/145976 A1 * | 12/2008 | .............. C07C 51/12 |
| WO | WO 2009000673 | 12/2008 | |
| WO | WO 2009003898 | 1/2009 | |
| WO | WO 2009008311 | 1/2009 | |
| WO | WO 2009018009 | 2/2009 | |
| WO | WO 2009050290 | 4/2009 | |
| WO | WO 2008056746 | 5/2009 | |
| WO | WO 2009021126 | 5/2009 | |
| WO | WO 2009062578 | 5/2009 | |
| WO | WO 2009063833 | 5/2009 | |
| WO | WO 2009066778 | 5/2009 | |
| WO | WO 2009066779 | 5/2009 | |
| WO | WO 2009086028 | 7/2009 | |
| WO | WO 2009100991 | 8/2009 | |
| WO | WO 2009/111299 | 9/2009 | |
| WO | WO 2009/111799 | 9/2009 | |
| WO | WO 2010/013239 | 2/2010 | |

OTHER PUBLICATIONS

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 3, 4-6 (1999).

Wang et al., "Remarkable Bromination and Blue Emission of 9-Anthracenyl Pt(II) Complexes", J. Am. Chem. Soc. 2009, 131, 3150-3151.

Zhang et. al. (Chem. Commun. 2008, 46, 6170).

Develay et al. Inorganic Chemistry 47 (23) pp. 11129-11142 (2008).

Willison et al., Inorg. Chem. 47 (4) pp. 1258-1260 (2008).

Brune et al., Journal of Organometallic Chemistry, 371 (1989) 121-127, The Netherlands.

Heng et al., "Attaching Gold and Platinum to the Rim of Pyrene: A Syntheticand Spectroscopic Study" Organometallics 2007, 26, 6760-6768.

Hu et al., "Photooxidation of a Platinum-Anthracene Pincer Complex: Formation and Structures of PtII-Anthrone and -Ketal Complexes", Inorg. Chem. 2009, 48, 9684-9692.

Singh et al., "Pt and Pd 1,4-Shifts at the Edge of ibenz[a,c]anthracene" J. Am. Chem. Soc. 2006, 128, 5998-5999.

Weisemann et al., Journal of Organometallic Chemistry, 365 (1989) 403-412, The Netherlands.

U.S. Appl. No. 61/397,516, filed Jun. 11, 2010.

Kuwabara, Yoshiyuki et al., "Thermally Stable Multilayered Organic Electroluminescent Devices Using Novel Starburst Molecules, 4,4',4"-Tri(*N*-carbazolyl)triphenylamine (TCTA) and 4,4',4"-Tris(*N*-methylphenylphenyl-amino)triphenylamine (*m*-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater*, 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,*N*)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(*I*) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865- 867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2)156-158 (2001).

Wang, Y. et al., "Highly Efficient Electroluminescent Materials Based on Fluorinated Organometallic Iridium Compounds," *Appl. Phys. Lett.*, 79(4):449-451 (2001).

(56) References Cited

OTHER PUBLICATIONS

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing N^C^N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Indium(III) Complexes at Room Temperature," *Chem. Mater*, 18(21):5119-5129 (2006).

Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cydometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota, Yasuhiko, "5,5'-Bis(dimesitylboryl)-2,2'-bithiophene and 5,5Δ-Bis(dimesitylboryl)-2,2':5',2'-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electra-Optical Characteristics Related to Structure," *Synthetic Metals*, 87:171-177 (1997).

Hu, Nan-Xing et al., "Novel High $T_g$ Hole-Transport Molecules Based on Indolo[3,2-*b*]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

* cited by examiner when X is C or N

DELAYED FLUORESCENCE OLED

This application claims priority to U.S. Provisional Application No. 61/397,516, filed on Jun. 11, 2010, the disclosure of which is herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention pertains to luminescent materials comprising an anthracene or acridine ligand substituted at the 9 and 10 positions, and devices comprising these compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for luminescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted $Ir(ppy)_3$, which has the structure:

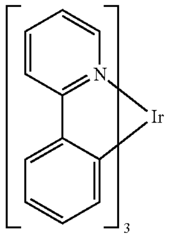

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a metal coordinated to an anthracene or acridine ligand are provided. The compounds comprise a ligand L having the formula:

Formula I

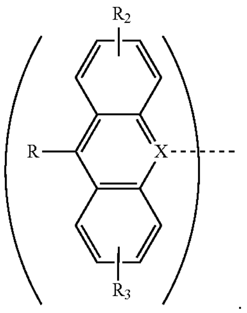

X is C or N. R is selected from alkyl, alkenyl, alkynyl, amino, alkoxy, silyl, phosphino, mercaptyl, aryl or heteroaryl. $R_2$ and $R_3$ may represent mono, di, tri, or tetra substitutions. $R_2$ and $R_3$ are independently selected from the group consisting of hydrogen, alkyl, alkoxy, amino, alkenyl, alkynyl, aryl and heteroaryl. The ligand L is coordinated to a metal M through coordinating atom X. M is a transition metal. The ligand L is optionally linked to a second ligand, which is also coordinated to the metal M.

In one aspect, the metal M is four coordinate. Preferably, the metal M is a $3^{rd}$ row transition metal. More preferably, M is Pt.

In another aspect, $R_2$ and $R_3$ are fused cyclic or heterocyclic rings.

In one aspect, the compound has the formula:

Formula II

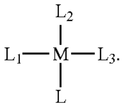

$L_1$, $L_2$, and $L_3$ are different from L and independently C, N, O, Si, P, S, or Se coordinating ligands to the metal M. In one aspect, one of $L_1$, $L_2$, and $L_3$ is anthracenyl. In another aspect, the compound has the formula:

Formula III

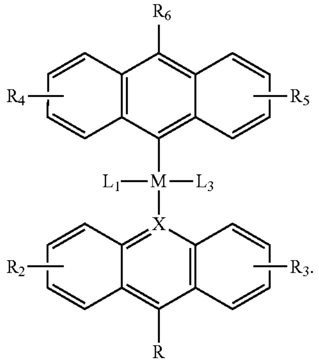

$R_6$ is selected from alkyl, alkenyl, alkynyl, amino, alkoxy, silyl, phosphino, mercaptyl, aryl or heteroaryl. $R_4$ and $R_5$ may represent mono, di, tri, or tetra substitutions. $R_4$ and $R_5$ are independently selected from the group consisting of hydrogen, alkyl, alkoxy, amino, alkenyl, alkynyl, aryl and heteroaryl.

In one aspect, the compound is neutral. In another aspect, the compound is charged.

In one aspect, R is aryl or heteroaryl. Preferably, R is selected from the group consisting of:

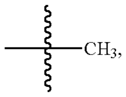,
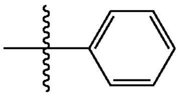,
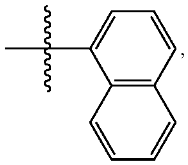,

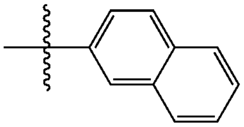,
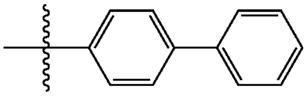,

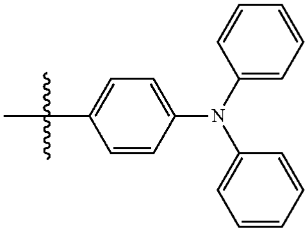,

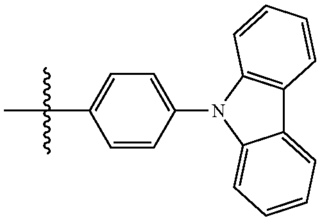

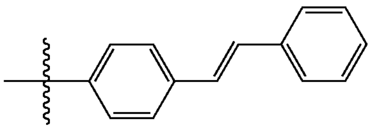,

-continued

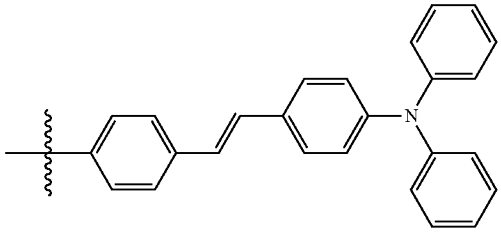

,

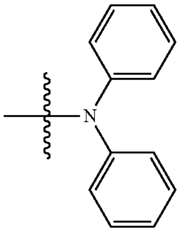

,

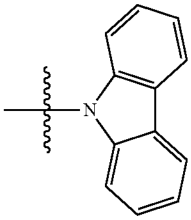

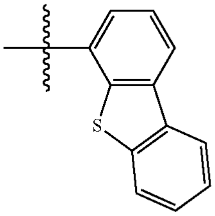

,

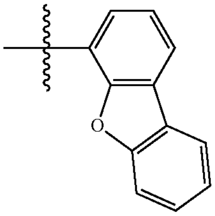

,

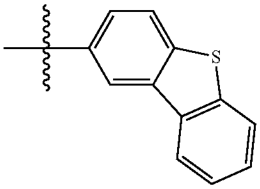

,

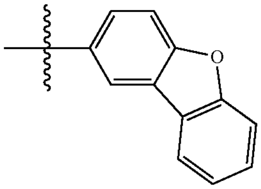

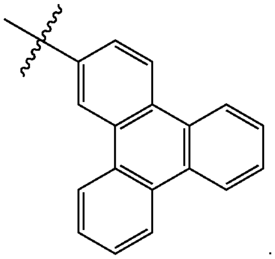

.

In one aspect, any two of L, $L_1$, $L_2$, and $L_3$ are linked together to form a bidentate ligand. In another aspect, at least one of the bidentate ligands forms a 5-member cyclometallating ring with M.

In one aspect, any three of L, $L_1$, $L_2$, and $L_3$ are linked together to form a tridentate ligand. In another aspect, the tridentate ligand forms at least one 5-member cyclometallating ring with M.

Specific examples of compounds comprising an anthracene or acridine ligand are provided. In particular, the compound is selected from the group consisting of:

Compound 1G

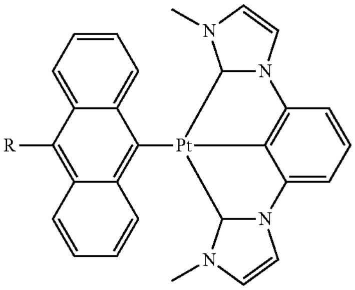

Compound 2G

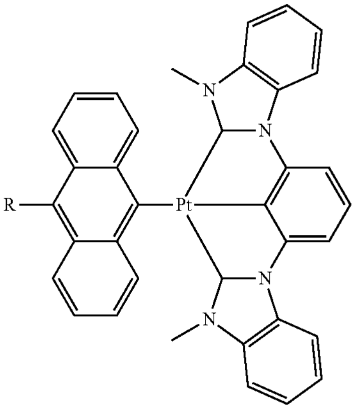

Compound 3G

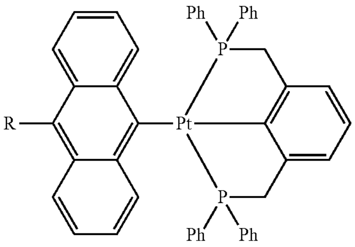

Compound 4G

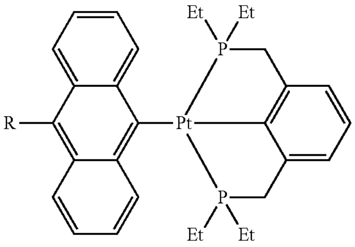

Compound 5G

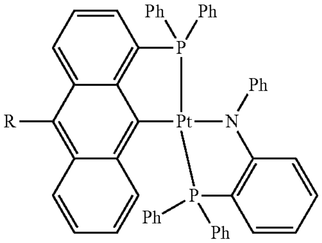

Compound 6G
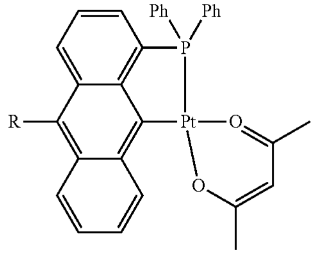
Compound 7G
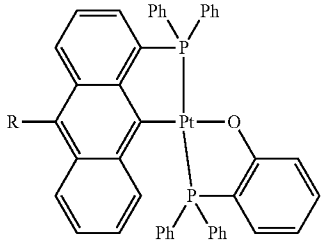
Compound 8G
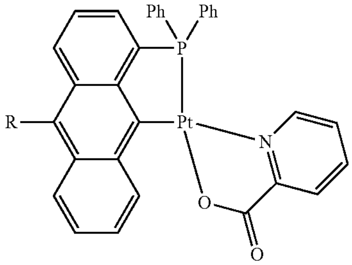
Compound 9G
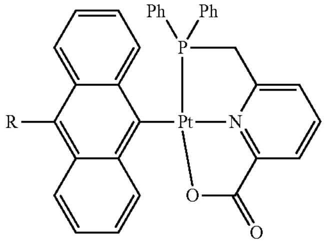
Compound 10G
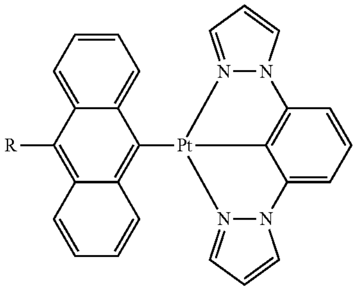
Compound 11G
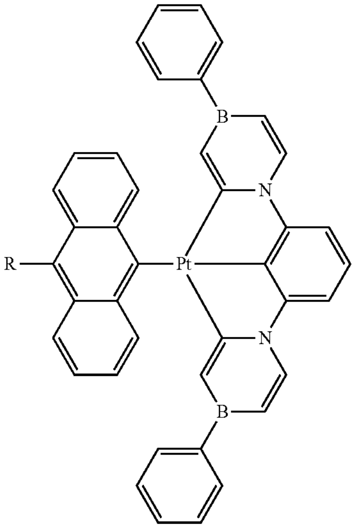
Compound 12G
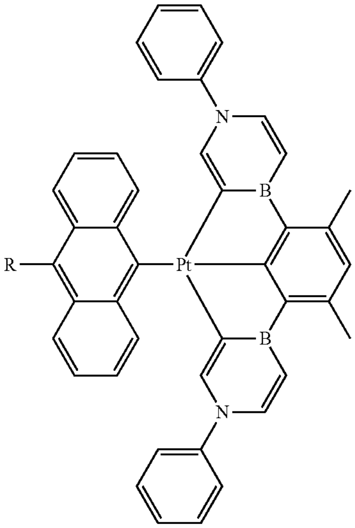
Compound 13G
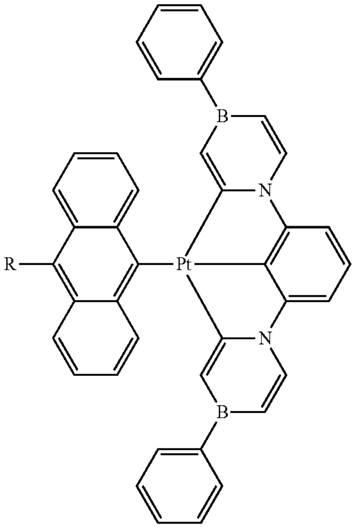

-continued
Compound 14G
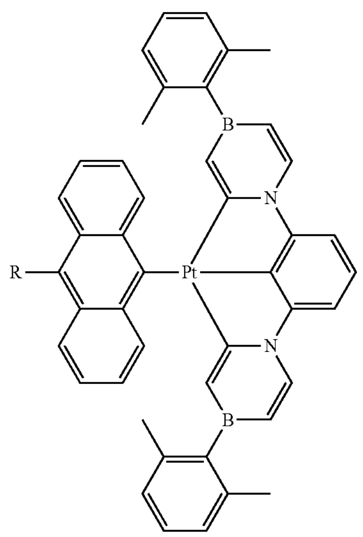
Compound 15G
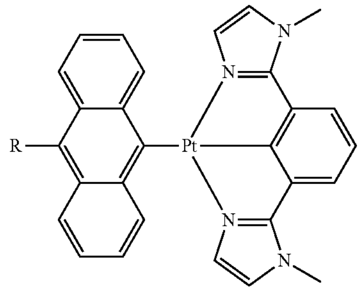
Compound 16G
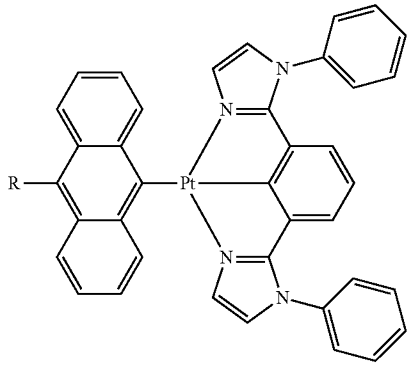
-continued
Compound 17G
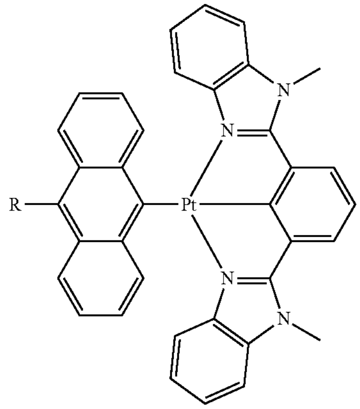
Compound 18G
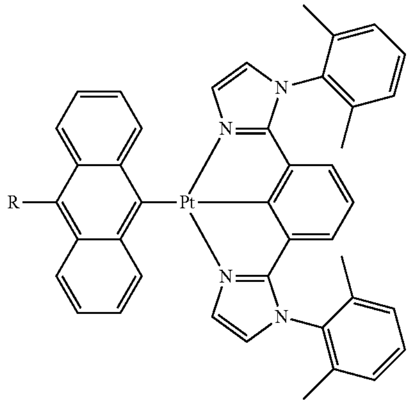
Compound 19G
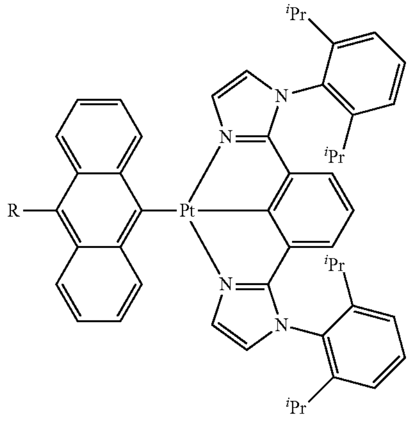

-continued
Compound 20G
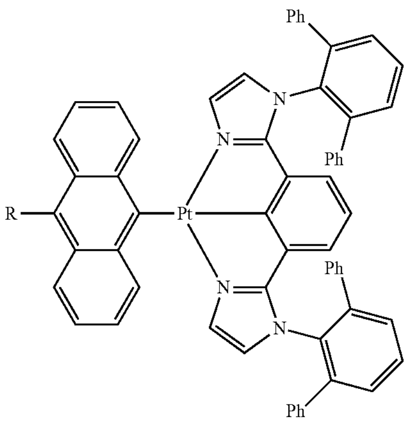
Compound 21G
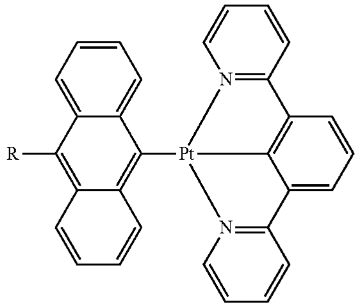
Compound 22G
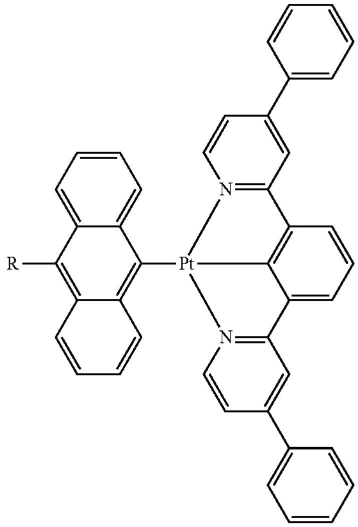
Compound 23G
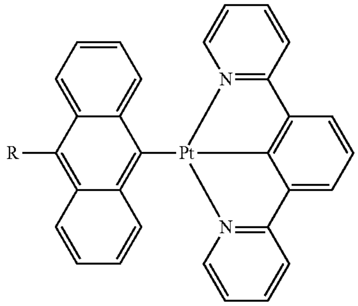
-continued
Compound 24G
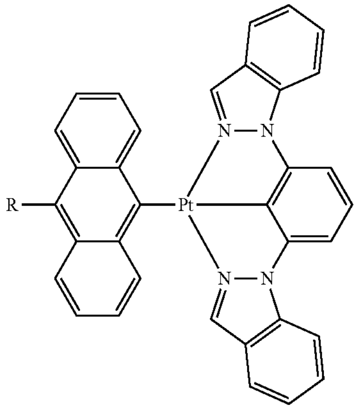
Compound 25G
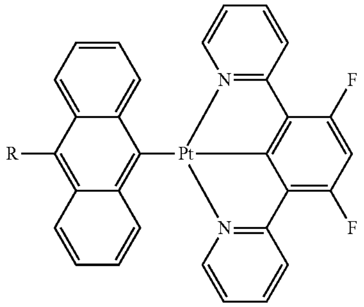
Compound 26G
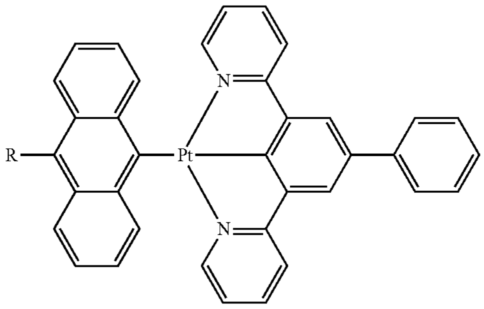
Compound 27G
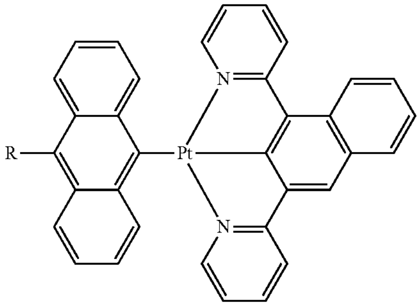

-continued
Compound 28G
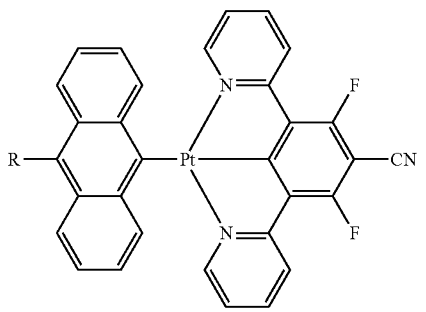
Compound 29G
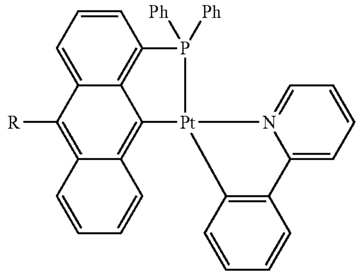
Compound 30G
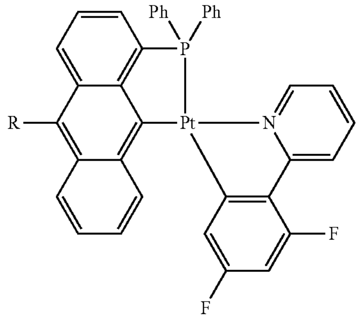
Compound 31G
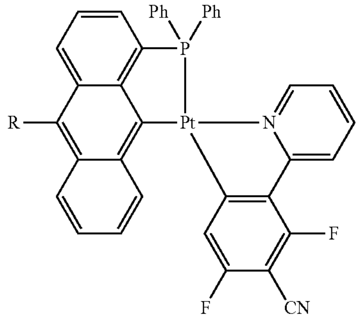
Compound 32G
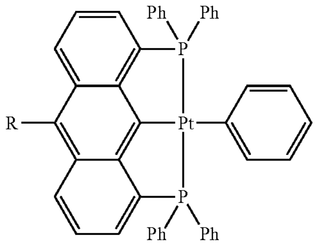
-continued
Compound 33G
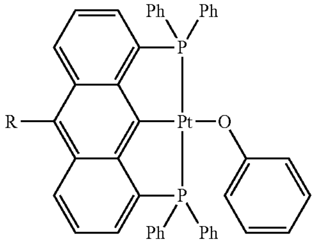
Compound 34G
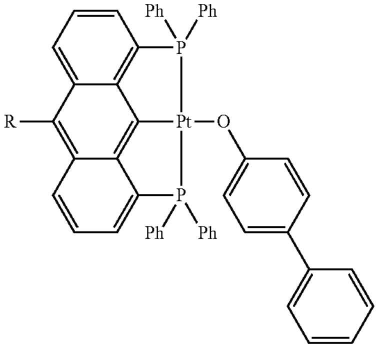
Compound 35G
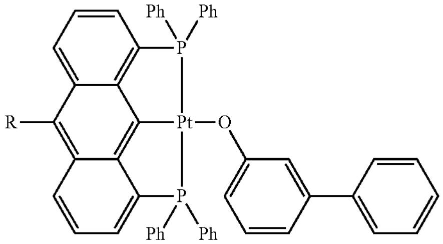
Compound 36G
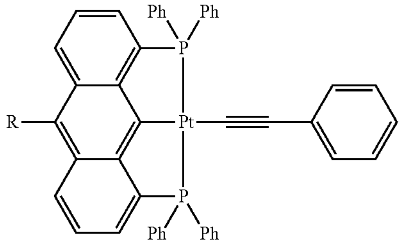
Compound 37G
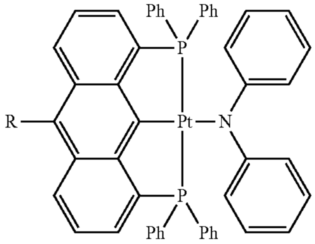

-continued
Compound 38G
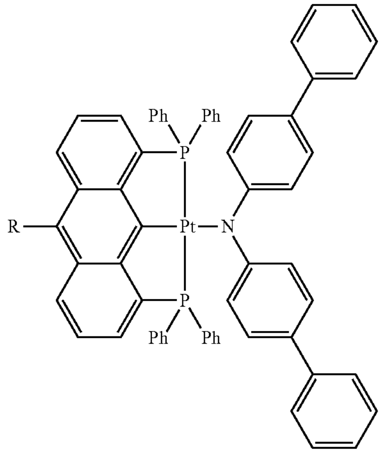
Compound 39G
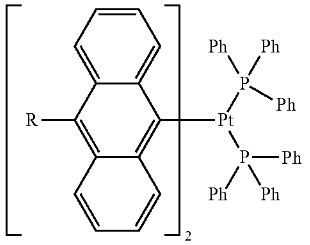
Compound 40G
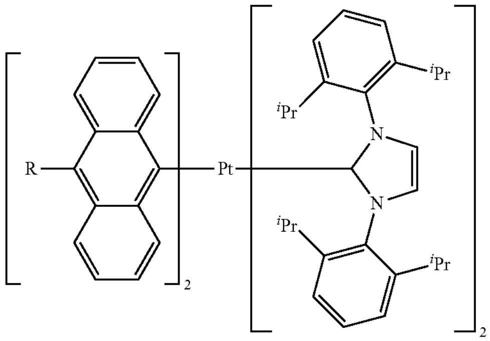
Compound 41G
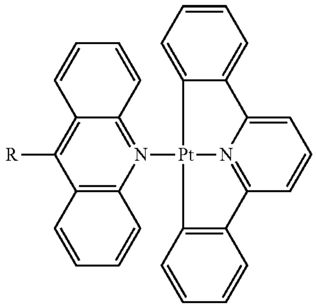
-continued
Compound 42G
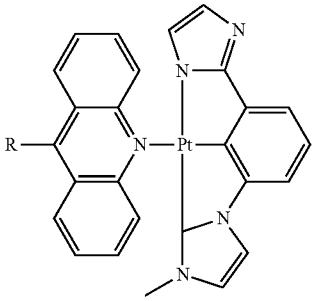
Compound 43G
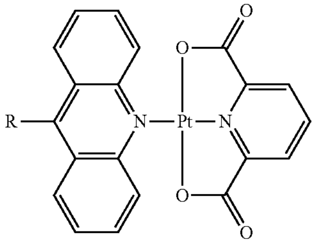
Compound 44G
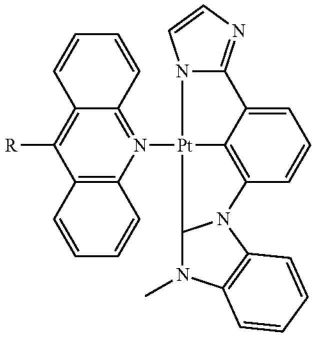
Compound 45G
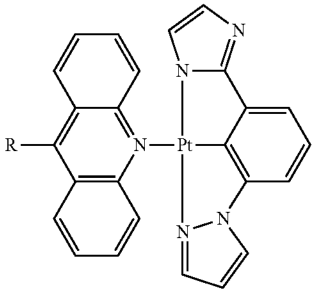
Compound 46G
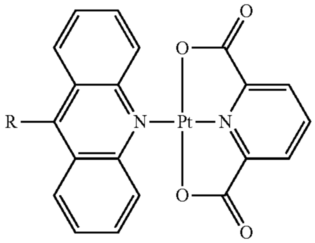

-continued

Compound 47G

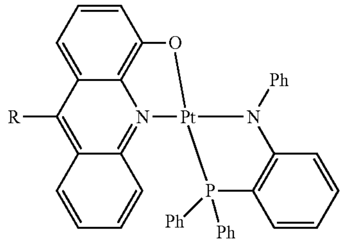

Compound 48G

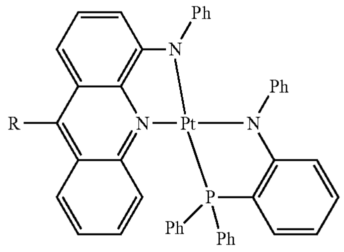

Compound 49G

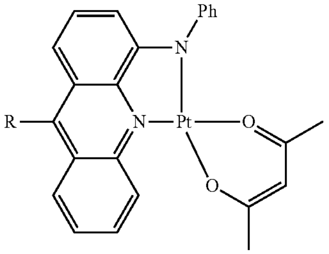

Compound 50G

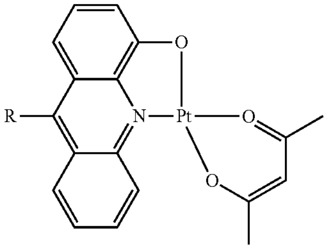

Compound 51G

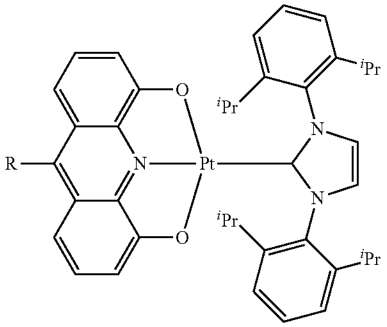

-continued

Compound 52G

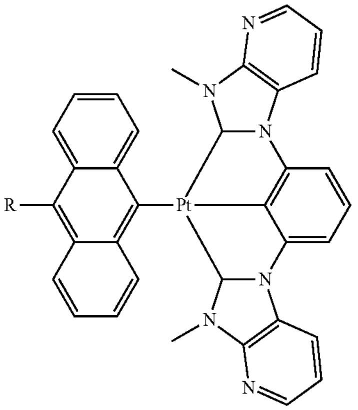

Compound 53G

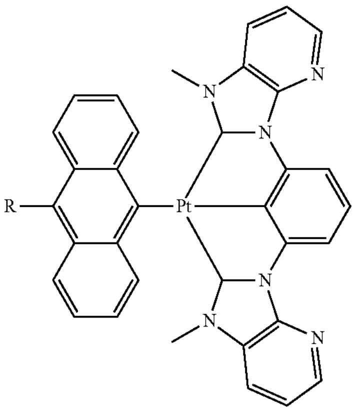

Compound 54G

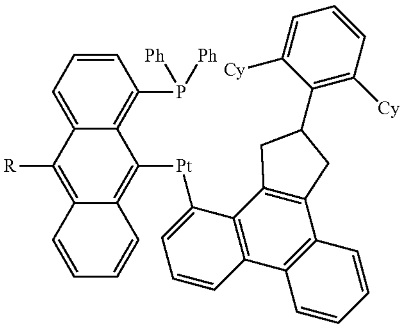

Particularly preferred compounds include compounds selected from the group consisting of Compound 1-1-Compound 54-14, as shown in Tables 1 and 2.

In one aspect, the triplet energy of the

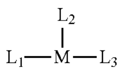

moiety is higher than 450 nm.

In another aspect, the compound has a luminescence lifetime having a long component of more than 0.1 microseconds.

A first device comprising an organic light emitting device is also provided. The first device further comprises an anode, a cathode, and an organic layer, disposed between the anode and the cathode. The organic layer comprises a compound comprising a ligand L having Formula I, as described above.

X is C or N. R is selected from alkyl, alkenyl, alkynyl, amino, alkoxy, silyl, phosphino, mercaptyl, aryl or heteroaryl. $R_2$ and $R_3$ may represent mono, di, tri, or tetra substitutions. $R_2$ and $R_3$ are independently selected from the group consisting of hydrogen, alkyl, alkoxy, amino, alkenyl, alkynyl, aryl and heteroaryl. M is a transition metal. The ligand L is coordinated to a metal M through coordinating atom X. The ligand L is optionally linked to a second ligand, which is also coordinated to the metal M.

In one aspect, the metal M is four coordinate. Preferably, the metal M is a $3^{rd}$ row transition metal. More preferably, M is Pt.

In another aspect, $R_2$ and $R_3$ are fused cyclic or heterocyclic rings.

In one aspect, the compound has Formula II, as discussed above. $L_1$, $L_2$, and $L_3$ are different from L and independently C, N, O, Si, P, S, or Se coordinating ligands to the metal M.

In another aspect, one of $L_1$, $L_2$, and $L_3$ is anthracenyl.

In one aspect, the compound has Formula III, as discussed above. $R_6$ is selected from alkyl, alkenyl, alkynyl, amino, alkoxy, silyl, phosphino, mercaptyl, aryl or heteroaryl. $R_4$ and $R_5$ may represent mono, di, tri, or tetra substitutions. $R_4$ and $R_5$ are independently selected from the group consisting of hydrogen, alkyl, alkoxy, amino, alkenyl, alkynyl, aryl and heteroaryl.

In one aspect, the compound is neutral. In another aspect, the compound is charged.

In one aspect, R is aryl or heteroaryl. In another aspect, R is selected from the group consisting of:

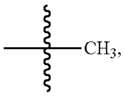 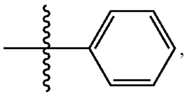, 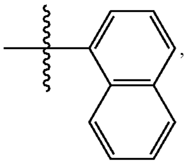,

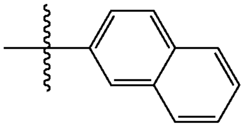, 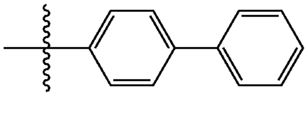,

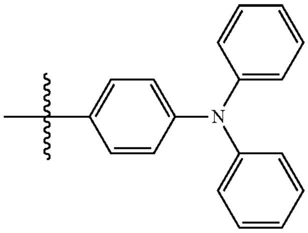,

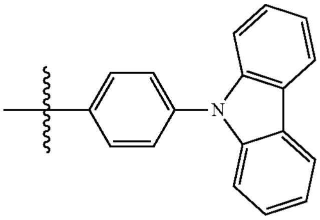

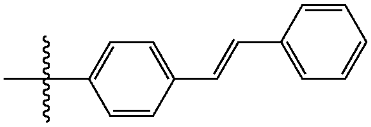,

-continued

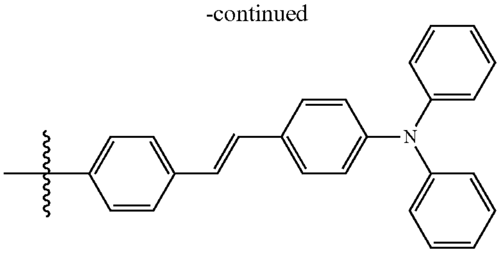,

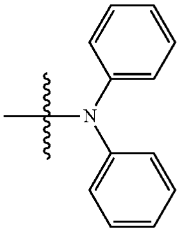, 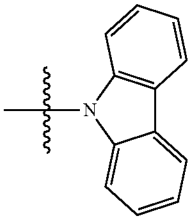

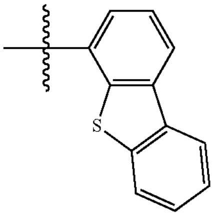, 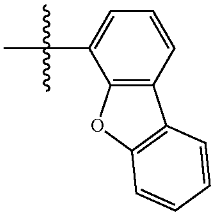,

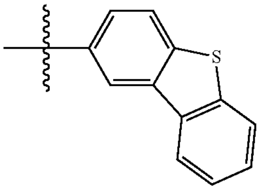, 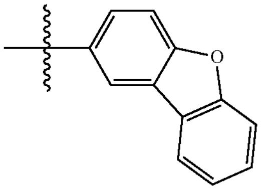

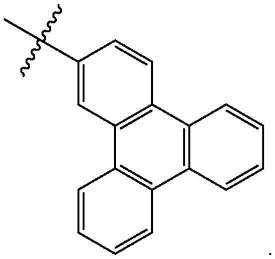.

In one aspect, any two of L, $L_1$, $L_2$, and $L_3$ are linked together to form a bidentate ligand. In another aspect, at least one of the bidentate ligands forms a 5-member cyclometallating ring with M.

In one aspect, any three of L, $L_1$, $L_2$, and $L_3$ are linked together to form a tridentate ligand. In another aspect, the tridentate ligand forms at least one 5-member cyclometallating ring with M.

Specific examples of first devices comprising these compounds, which themselves comprise an anthracene or acridine ligand, are provided. In particular, the compound is selected from the group consisting of Compound 1G-Compound 54G.

Particularly preferred compounds include compounds selected from the group consisting of Compound 1-1-Compound 54-14, as shown in Tables 1 and 2.

In one aspect, the organic layer is an emissive layer and the compound is an emissive dopant.

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
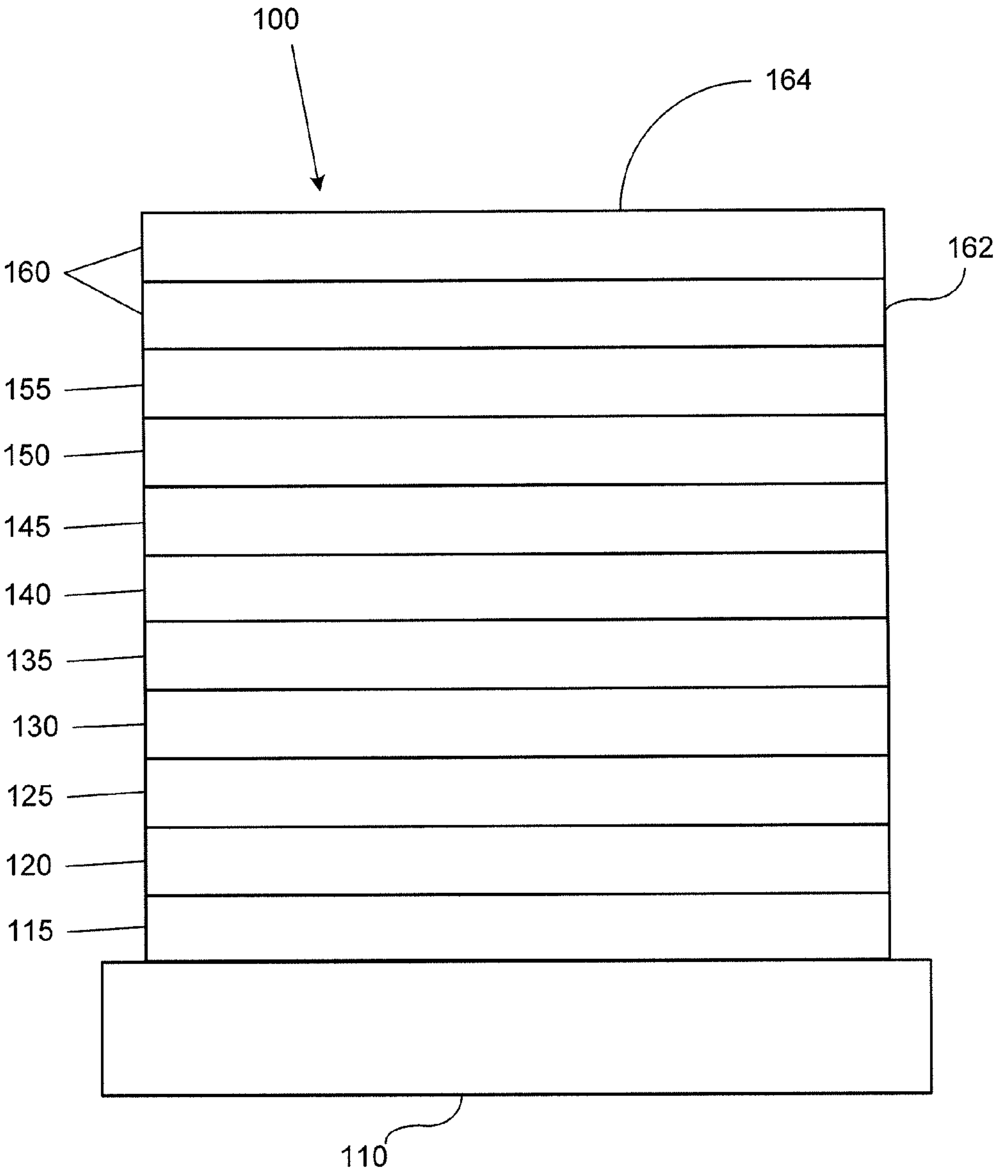
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
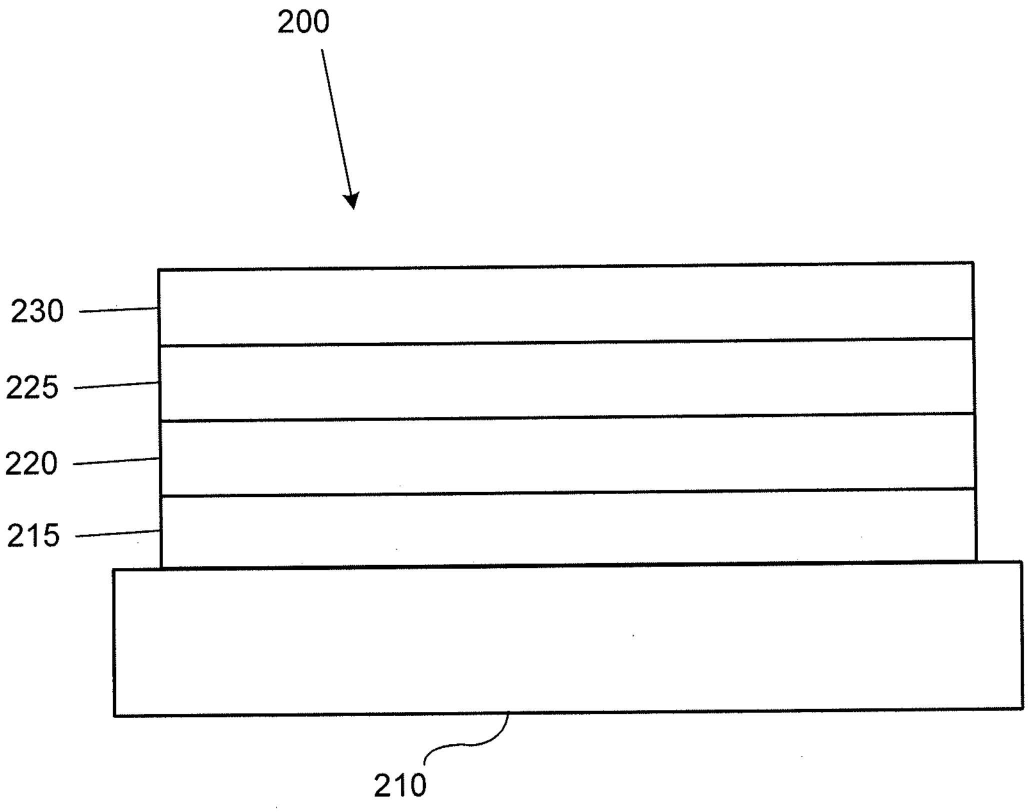
FIG. 2 shows an inverted organic light emitting device that does not have a separate electron transport layer.
Figure 3:
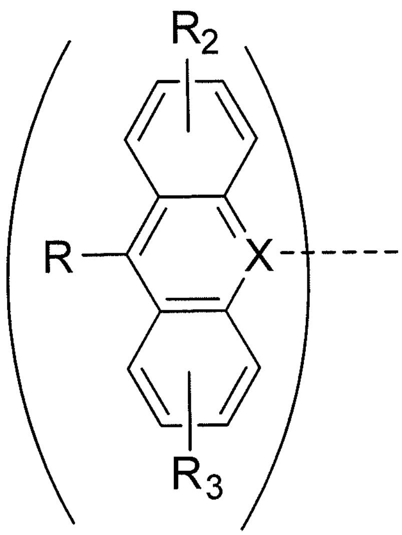
FIG. 3 shows an anthracene or acridine ligand coordinated to a metal.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the embodiments of the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Blue organic light emitting devices, particularly deeper blue ($x \leq 0.17$, $y \leq 0.30$), are a challenging topic. OLEDs using blue fluorescent emitters may be quite stable (>10000 h at $L_0$=1000 cd/$m^2$), but their efficiency is low (EQE<10%). Conversely, OLEDs using blue phosphorescent emitters may be very efficient (EQE>15%), but their stability is low (<5000 h at $L_0$=1000 cd/$m^2$). Therefore, blue OLEDs can have significant problems.

All of the excitons can be utilized in phosphorescent devices. Therefore, theoretically, phosphorescent devices are advantageous. However, in the blue emission regime, phosphorescent devices require the use of high energy phosphorescent emitting compounds and high triplet energy hosts. Consequently, the compounds used in blue emitting phosphorescent devices can only have limited π-conjugation. The limited π-conjugation may lead to the inability to stabilize charges during device operation, resulting in short device operational lifetimes. As disclosed herein, delayed fluorescence from stable fluorescence emitters, such as Pt(II)-anthracene or acridine compounds, directly addresses this problem.

During device operation, 25% of singlet excitons and 75% of triplet excitons are formed, according to spin statistics. Pt(II)-anthracene can emit directly from the singlet exciton, resulting in prompt fluorescence. Some of the singlet excitons can also undergo intersystem crossing to the triplet state. The triplet excitons, directly formed upon charge recombination or indirectly formed by intersystem crossing from the singlet state, can annihilate to generate singlet excitons that then emit. This is called delayed fluorescence and it has the same emission as the prompt fluorescence, because they come from the same singlet state. Through the delayed fluorescence process, a significant part of the triplet excitons are used to generate the emission, resulting in improved OLED device efficiency.

Overall device efficiency is still limited by the photoluminescence quantum yield (PLQY) of the emitter. It is believed that the compounds provided herein may achieve a high PLQY, because the 9 and/or 10 position of anthracene or the 9 position of acridine is substituted. In particular, the compounds provided have a substituent other than hydrogen at the 10 position on the anthracene ligand having Formula I. Without being bound by theory, it is believed that if H is at the 9 and/or 10 positions of anthracene, the PLQY is lower than if the substituent is alkyl or aryl. For example, anthracene has a solution PLQY of about 40%, but 9,10-diphenylanthracene has a solution PLQY of 100%.

Compounds comprising a metal coordinated to an anthracene or acridine ligand are provided. The compounds comprise a ligand L having the formula:

Formula I

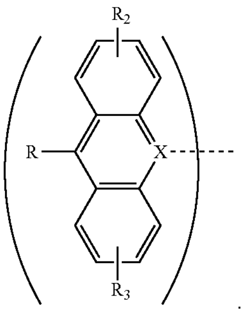

X is C or N. R is selected from alkyl, alkenyl, alkynyl, amino, alkoxy, silyl, phosphino, mercaptyl, aryl or heteroaryl. R is preferably a substituent other than halogen, because halogen containing compounds may lead to quick device degradation. Without being bound by theory it is believed that the carbon-halogen bind is prone to cleavage, which may result in faster device degradation. $R_2$ and $R_3$ may represent mono, di, tri, or tetra substitutions. $R_2$ and $R_3$ are independently selected from the group consisting of hydrogen, alkyl, alkoxy, amino, alkenyl, alkynyl, aryl and heteroaryl. The ligand L is coordinated to a metal M through coordinating atom X. M is a transition metal. The ligand L is optionally linked to a second ligand, which is also coordinated to the metal M.

In one aspect, the metal M is four coordinate. Preferably, the metal M is a 3rd row transition metal. More preferably, M is Pt.

In another aspect, $R_2$ and $R_3$ are fused cyclic or heterocyclic rings.

In one aspect, the compound has the formula:

Formula II

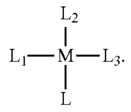

$L_1$, $L_2$, and $L_3$ are different from L and independently C, N, O, Si, P, S, or Se coordinating ligands to the metal M. In one aspect, one of $L_1$, $L_2$, and $L_3$ is anthracenyl. In another aspect, the compound has the formula:

Formula III

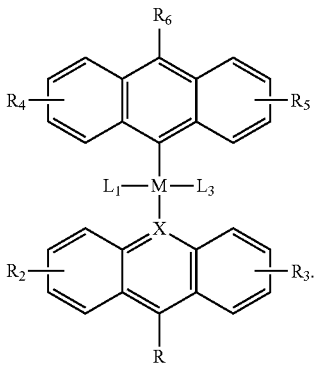

$R_6$ is selected from alkyl, alkenyl, alkynyl, amino, alkoxy, silyl, phosphino, mercaptyl, aryl or heteroaryl. $R_4$ and $R_5$ may represent mono, di, tri, or tetra substitutions. $R_4$ and $R_5$ are independently selected from the group consisting of hydrogen, alkyl, alkoxy, amino, alkenyl, alkynyl, aryl and heteroaryl.

In one aspect, the compound is neutral. In another aspect, the compound is charged.

In one aspect, R is aryl or heteroaryl. Preferably, R is selected from the group consisting of:

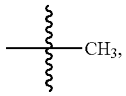,
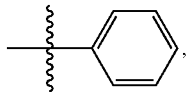,
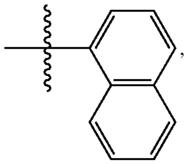,
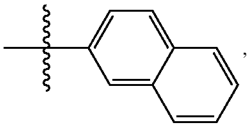,
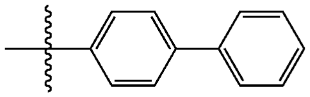,

-continued

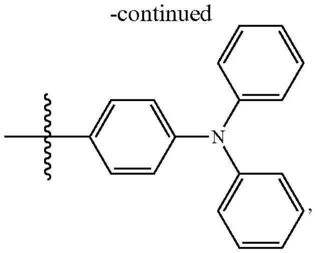,
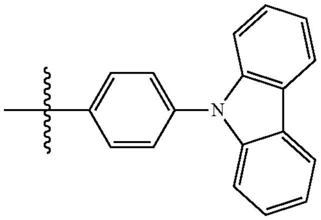
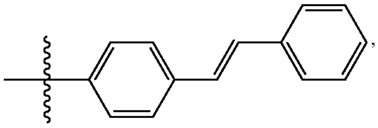,
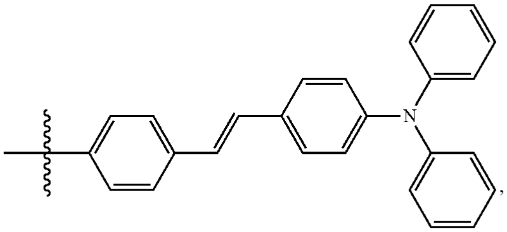,
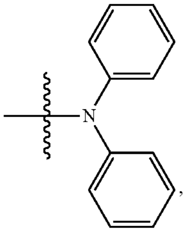
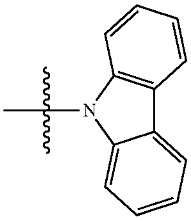
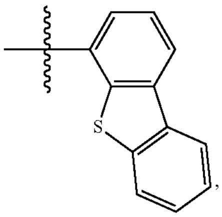,
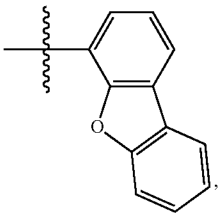,
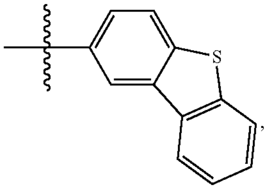,
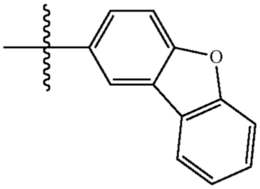
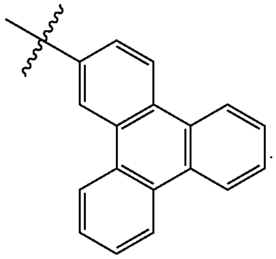.

Without being bound by theory, it is believed that multidentate ligands, i.e., bidentate and tridentate, can provide higher stability in thermal evaporation and device operation because they chelate more strongly to the metal M. The bidentate or tridentate cyclometallating mode is preferably a 5-member metallocycle because it is believed that 5-member metallocycles are much more chemically stable, resulting in high device stability.

In one aspect, any two of L, $L_1$, $L_2$, and $L_3$ are linked together to form a bidentate ligand. For example, at least one of $L_1$ and $L_2$, $L_2$ and $L_3$, $L_1$ and L, or $L_3$ and L are linked together to form a bidentate ligand. In another aspect, at least one of the bidentate ligands forms a 5-member cyclometallating ring with M.

In one aspect, any three of L, $L_1$, $L_2$, and $L_3$ are linked together to form a tridentate ligand. For example, one of $L_1$, $L_2$, and $L_3$ or $L_1$, L and $L_3$ are linked together to form a tridentate ligand. In another aspect, the tridentate ligand forms at least one 5-member cyclometallating ring with M.

Specific examples of compounds comprising a substituted anthracene or acridine ligand are provided. In particular, the compound is selected from the group consisting of:

Compound 1G

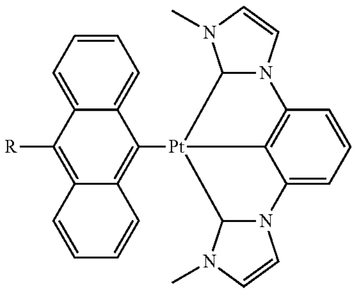

Compound 2G

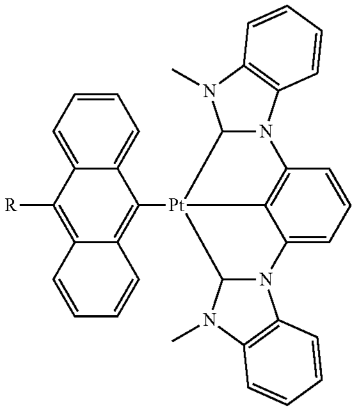

Compound 3G

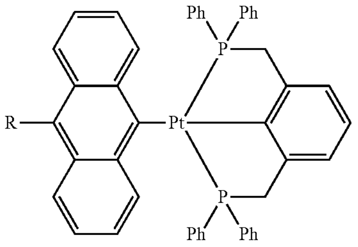

-continued

Compound 4G

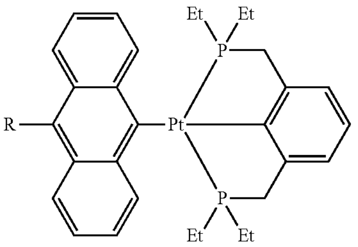

Compound 5G

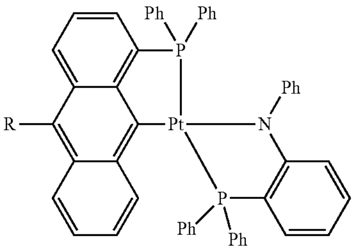

Compound 6G

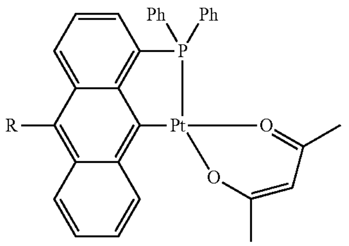

Compound 7G

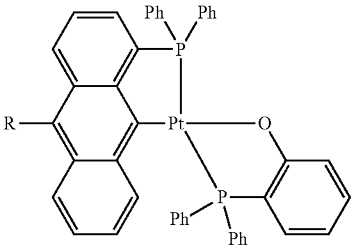

Compound 8G

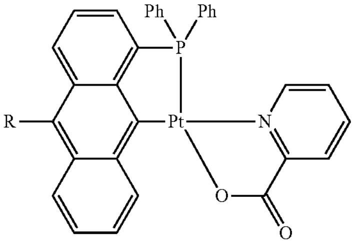

Compound 9G

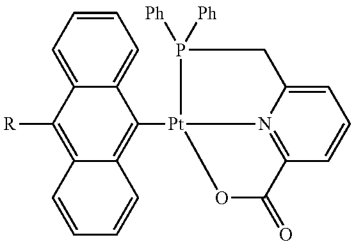

-continued
Compound 10G
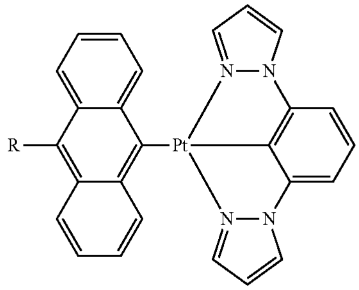
Compound 11G
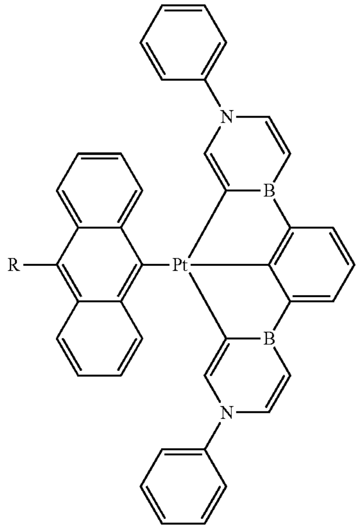
Compound 12G
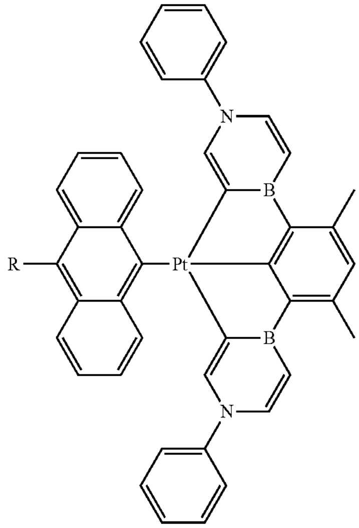
-continued
Compound 13G
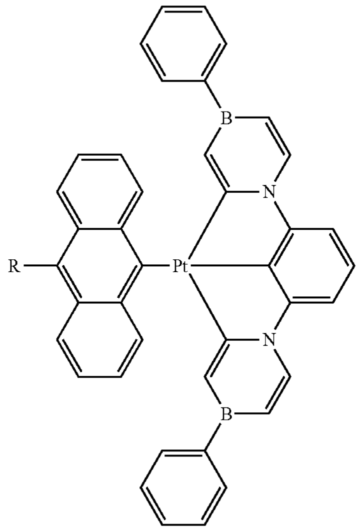
Compound 14G
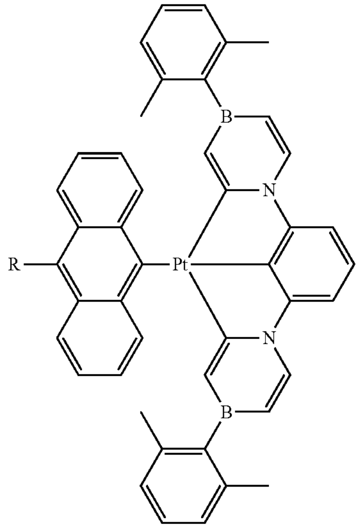
Compound 15G
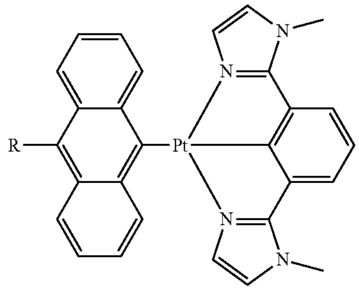

-continued
Compound 16G
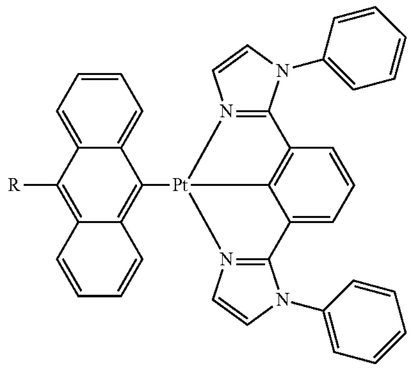
Compound 17G
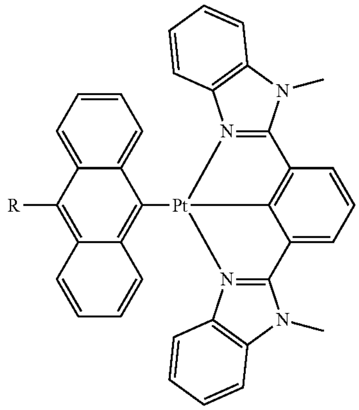
Compound 18G
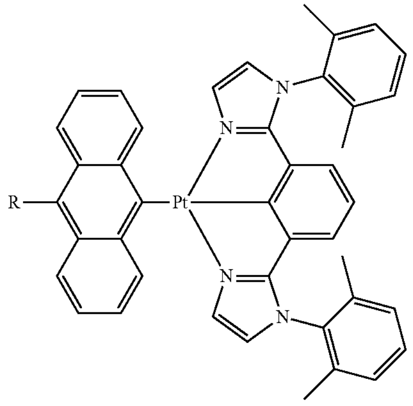
Compound 19G
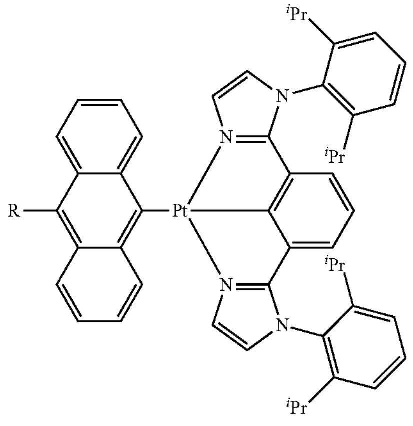
-continued
Compound 20G
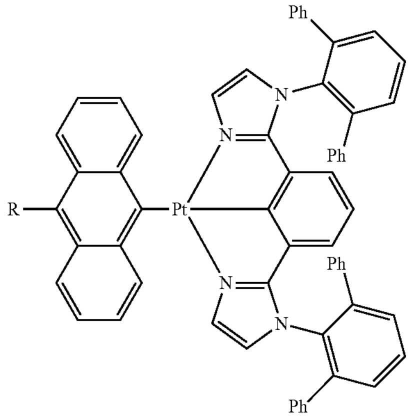
Compound 21G
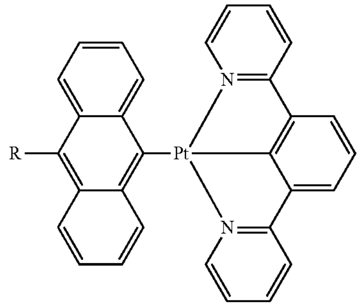
Compound 22G
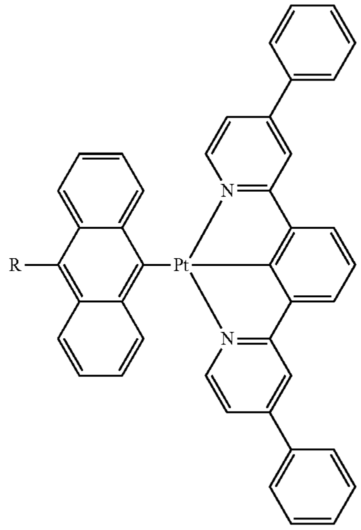
Compound 23G
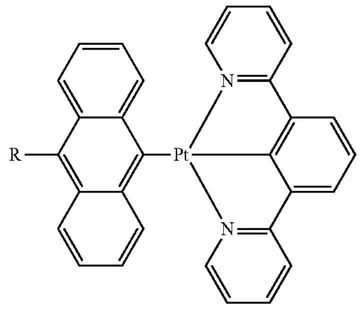

-continued
Compound 24G
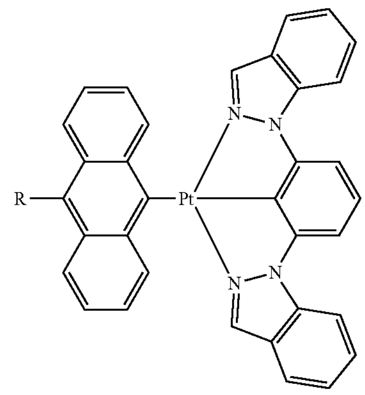
Compound 25G
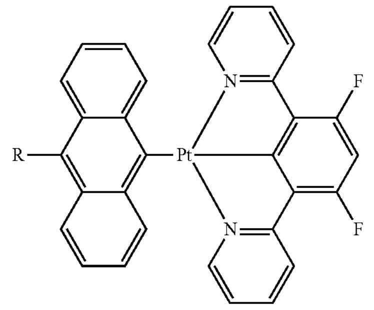
Compound 26G
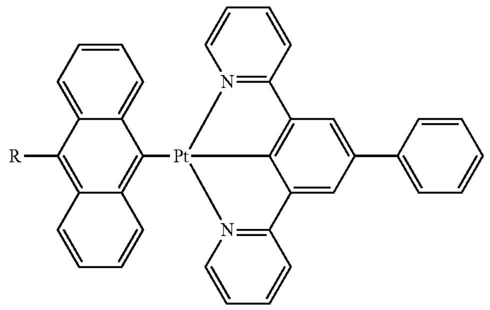
Compound 27G
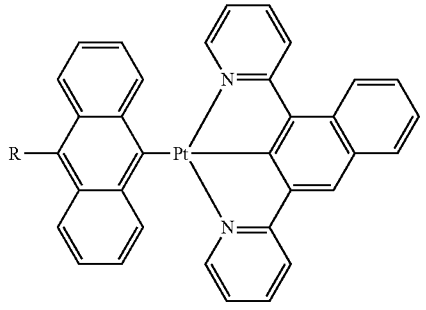
-continued
Compound 28G
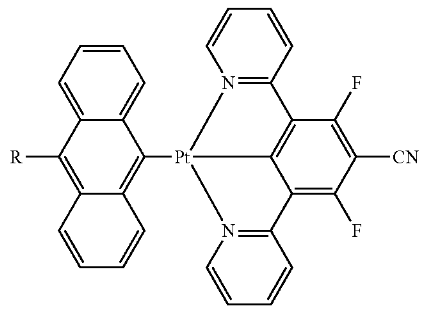
Comppund 29G
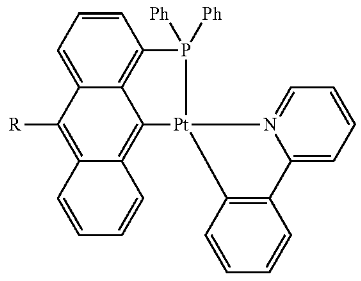
Compound 30G
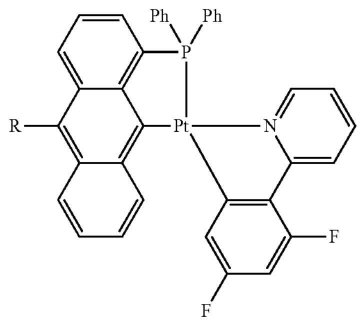
Compound 31G
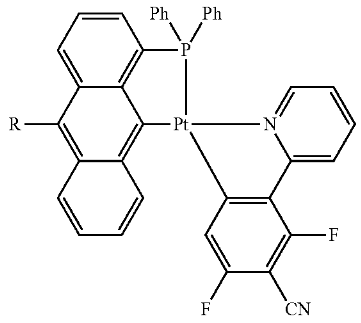
Compound 32G
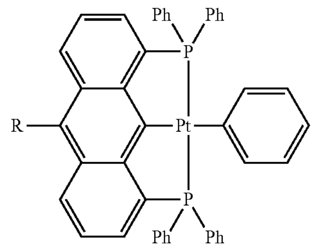

-continued
Compound 33G
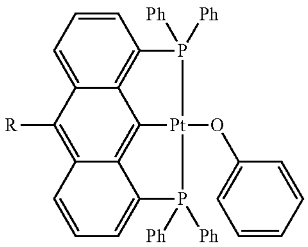
Compound 34G
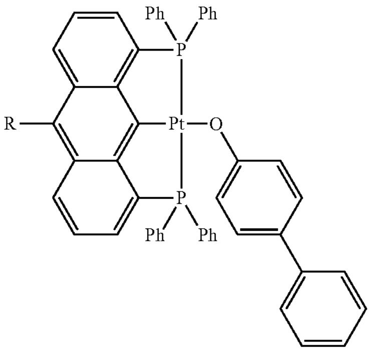
Compound 35G
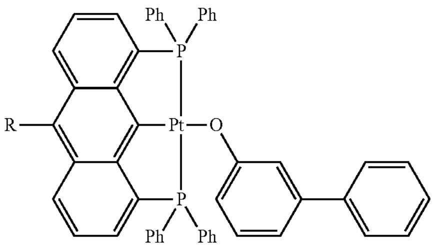
Compound 36G
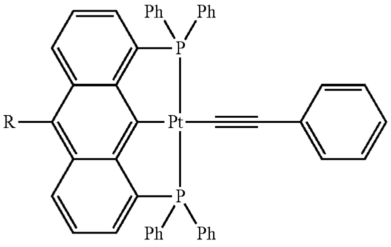
Compound 37G
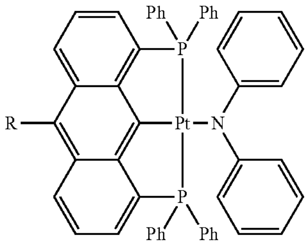
-continued
Compound 38G
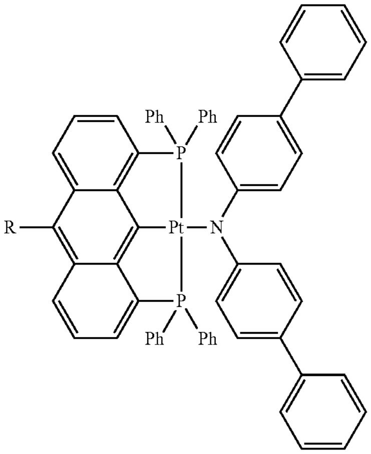
Compound 39G
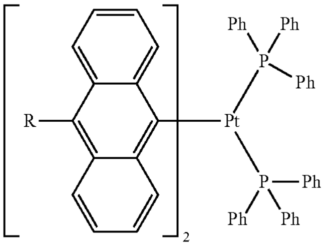
Compound 40G
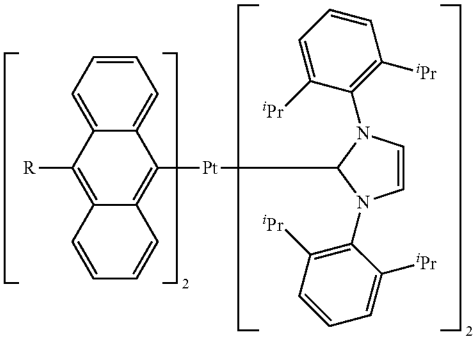
Compound 41G
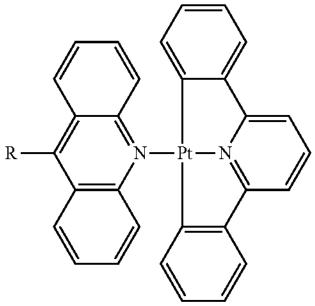

-continued
Compound 42G
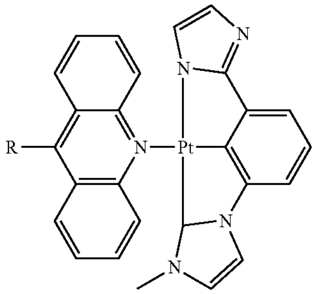
Compound 43G
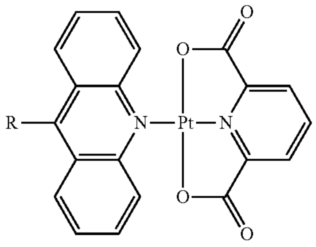
Compound 44G
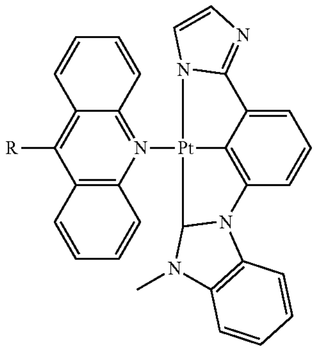
Compound 45G
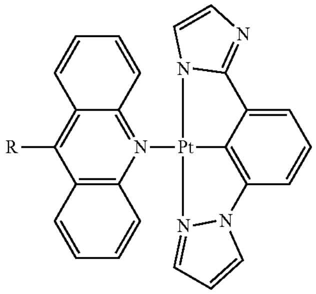
Compound 46G
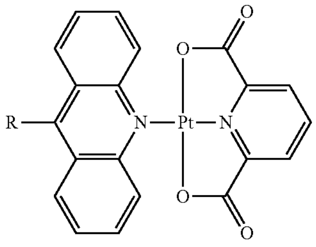
-continued
Compound 47G
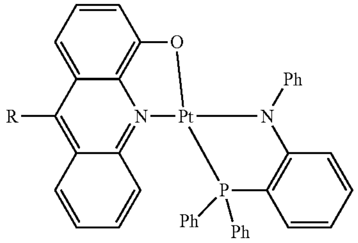
Compound 48G
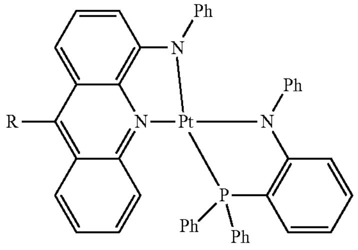
Compound 49G
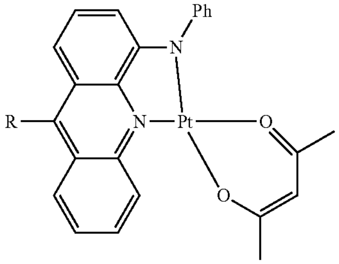
Compound 50G
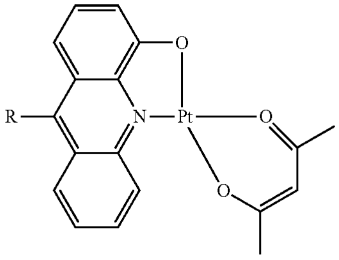
Compound 51G
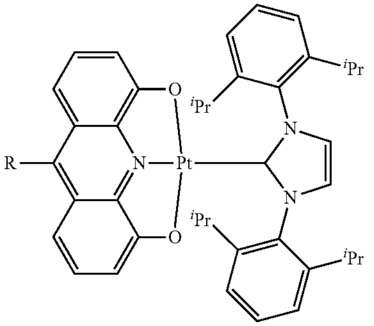

-continued
Compound 52G
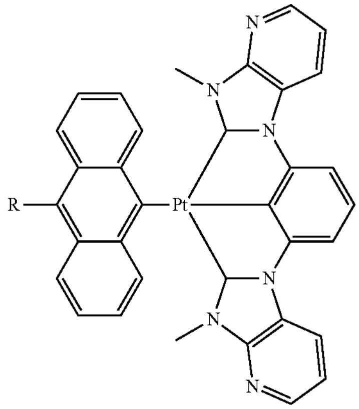
Compound 53G
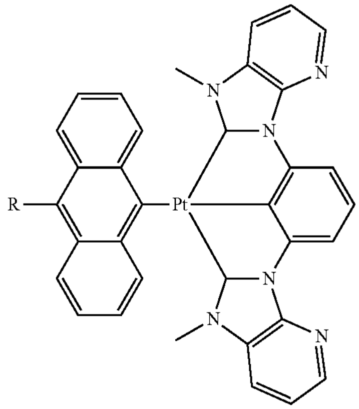
-continued
Compound 54G
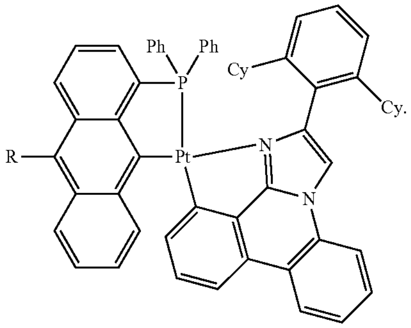
Preferred compounds include compounds having the general structures provided above that has a preferred substituent as R. In particular, preferred compounds are selected from the group consisting of:

TABLE 1
| Formula | 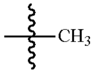 | 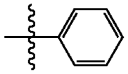 | 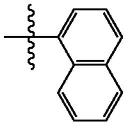 [SMILES: *c1cccc2ccccc12] | 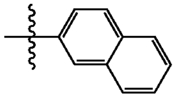 [SMILES: *c1ccc2ccccc2c1] | 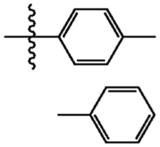 | 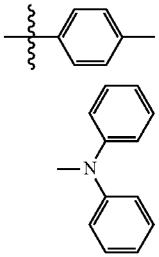 | 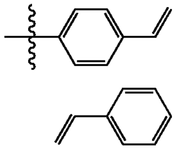 | 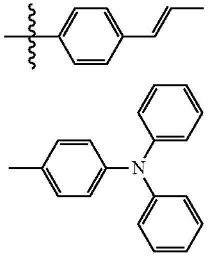 | 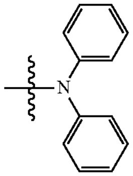 | Cmpd. |
|---|---|---|---|---|---|---|---|---|---|---|
| 1 | x | | | | | | | | | 1-1 |
| 1 | | x | | | | | | | | 1-2 |
| 1 | | | x | | | | | | | 1-3 |
| 1 | | | | x | | | | | | 1-4 |
| 1 | | | | | x | | | | | 1-5 |
| 1 | | | | | | x | | | | 1-6 |
| 1 | | | | | | | x | | | 1-7 |
| 1 | | | | | | | | x | | 1-8 |
| 1 | | | | | | | | | x | 1-9 |
| 2 | x | | | | | | | | | 2-1 |
| 2 | | x | | | | | | | | 2-2 |
| 2 | | | x | | | | | | | 2-3 |
| 2 | | | | x | | | | | | 2-4 |
| 2 | | | | | x | | | | | 2-5 |
| 2 | | | | | | x | | | | 2-6 |
| 2 | | | | | | | x | | | 2-7 |
| 2 | | | | | | | | x | | 2-8 |
| 2 | | | | | | | | | x | 2-9 |
| 3 | x | | | | | | | | | 3-1 |
| 3 | | x | | | | | | | | 3-2 |
| 3 | | | x | | | | | | | 3-3 |
| 3 | | | | x | | | | | | 3-4 |
| 3 | | | | | x | | | | | 3-5 |
| 3 | | | | | | x | | | | 3-6 |
| 3 | | | | | | | x | | | 3-7 |
| 3 | | | | | | | | x | | 3-8 |
| 3 | | | | | | | | | x | 3-9 |
| 4 | x | | | | | | | | | 4-1 |
| 4 | | x | | | | | | | | 4-2 |
| 4 | | | x | | | | | | | 4-3 |
| 4 | | | | x | | | | | | 4-4 |
| 4 | | | | | x | | | | | 4-5 |
| 4 | | | | | | x | | | | 4-6 |
| 4 | | | | | | | x | | | 4-7 |
| 4 | | | | | | | | x | | 4-8 |
| 4 | | | | | | | | | x | 4-9 |
| 5 | x | | | | | | | | | 5-1 |
| 5 | | x | | | | | | | | 5-2 |

TABLE 1-continued
| Formula | 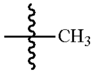 | 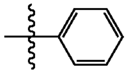 | 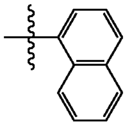 | 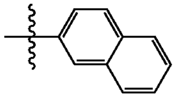 | 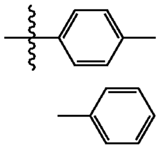 | 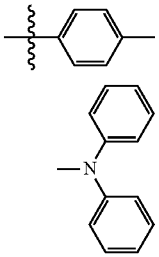 | 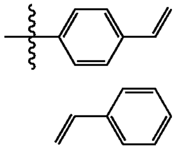 | 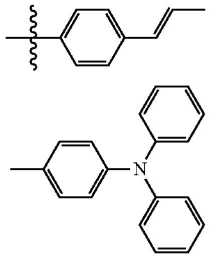 | 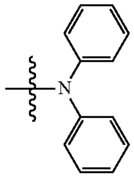 [SMILES: *N(c1ccccc1)c1ccccc1] | Cmpd. |
|---|---|---|---|---|---|---|---|---|---|---|
| 5 | | | x | | | | | | | 5-3 |
| 5 | | | | x | | | | | | 5-4 |
| 5 | | | | | x | | | | | 5-5 |
| 5 | | | | | | x | | | | 5-6 |
| 5 | | | | | | | x | | | 5-7 |
| 5 | | | | | | | | x | | 5-8 |
| 5 | | | | | | | | | x | 5-9 |
| 6 | x | | | | | | | | | 6-1 |
| 6 | | x | | | | | | | | 6-2 |
| 6 | | | x | | | | | | | 6-3 |
| 6 | | | | x | | | | | | 6-4 |
| 6 | | | | | x | | | | | 6-5 |
| 6 | | | | | | x | | | | 6-6 |
| 6 | | | | | | | x | | | 6-7 |
| 6 | | | | | | | | x | | 6-8 |
| 6 | | | | | | | | | x | 6-9 |
| 7 | x | | | | | | | | | 7-1 |
| 7 | | x | | | | | | | | 7-2 |
| 7 | | | x | | | | | | | 7-3 |
| 7 | | | | x | | | | | | 7-4 |
| 7 | | | | | x | | | | | 7-5 |
| 7 | | | | | | x | | | | 7-6 |
| 7 | | | | | | | x | | | 7-7 |
| 7 | | | | | | | | x | | 7-8 |
| 7 | | | | | | | | | x | 7-9 |
| 8 | x | | | | | | | | | 8-1 |
| 8 | | x | | | | | | | | 8-2 |
| 8 | | | x | | | | | | | 8-3 |
| 8 | | | | x | | | | | | 8-4 |
| 8 | | | | | x | | | | | 8-5 |
| 8 | | | | | | x | | | | 8-6 |
| 8 | | | | | | | x | | | 8-7 |
| 8 | | | | | | | | x | | 8-8 |
| 8 | | | | | | | | | x | 8-9 |
| 9 | x | | | | | | | | | 9-1 |
| 9 | | x | | | | | | | | 9-2 |
| 9 | | | x | | | | | | | 9-3 |
| 9 | | | | x | | | | | | 9-4 |
| 9 | | | | | x | | | | | 9-5 |
| 9 | | | | | | x | | | | 9-6 |

TABLE 1-continued
| Formula | 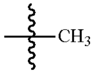 | 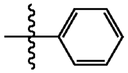 | 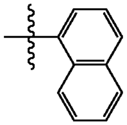 | 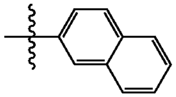 | 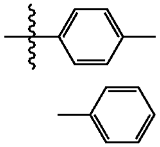 | 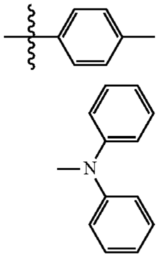 | 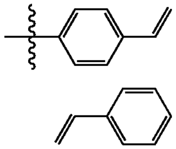 | 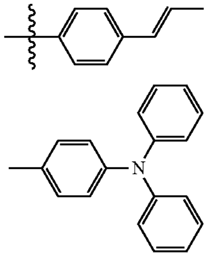 | 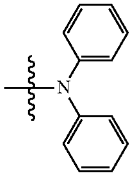 | Cmpd. |
|---|---|---|---|---|---|---|---|---|---|---|
| 9 | | | | | | | x | | | 9-7 |
| 9 | | | | | | | | x | | 9-8 |
| 9 | | | | | | | | | x | 9-9 |
| 10 | x | | | | | | | | | 10-1 |
| 10 | | x | | | | | | | | 10-2 |
| 10 | | | x | | | | | | | 10-3 |
| 10 | | | | x | | | | | | 10-4 |
| 10 | | | | | x | | | | | 10-5 |
| 10 | | | | | | x | | | | 10-6 |
| 10 | | | | | | | x | | | 10-7 |
| 10 | | | | | | | | x | | 10-8 |
| 10 | | | | | | | | | x | 10-9 |
| 11 | x | | | | | | | | | 11-1 |
| 11 | | x | | | | | | | | 11-2 |
| 11 | | | x | | | | | | | 11-3 |
| 11 | | | | x | | | | | | 11-4 |
| 11 | | | | | x | | | | | 11-5 |
| 11 | | | | | | x | | | | 11-6 |
| 11 | | | | | | | x | | | 11-7 |
| 11 | | | | | | | | x | | 11-8 |
| 11 | | | | | | | | | x | 11-9 |
| 12 | x | | | | | | | | | 12-1 |
| 12 | | x | | | | | | | | 12-2 |
| 12 | | | x | | | | | | | 12-3 |
| 12 | | | | x | | | | | | 12-4 |
| 12 | | | | | x | | | | | 12-5 |
| 12 | | | | | | x | | | | 12-6 |
| 12 | | | | | | | x | | | 12-7 |
| 12 | | | | | | | | x | | 12-8 |
| 12 | | | | | | | | | x | 12-9 |
| 13 | x | | | | | | | | | 13-1 |
| 13 | | x | | | | | | | | 13-2 |
| 13 | | | x | | | | | | | 13-3 |
| 13 | | | | x | | | | | | 13-4 |
| 13 | | | | | x | | | | | 13-5 |
| 13 | | | | | | x | | | | 13-6 |
| 13 | | | | | | | x | | | 13-7 |
| 13 | | | | | | | | x | | 13-8 |
| 13 | | | | | | | | | x | 13-9 |
| 14 | x | | | | | | | | | 14-1 |

TABLE 1-continued
| Formula | 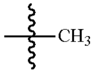 | 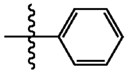 | 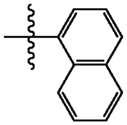 | 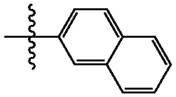 | 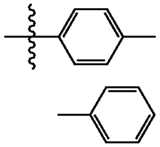 | 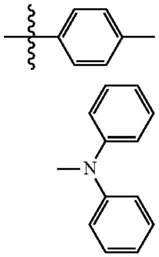 | 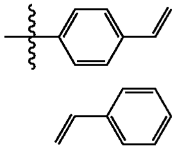 | 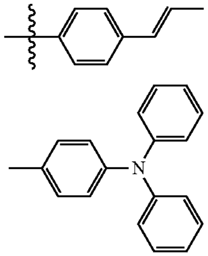 | 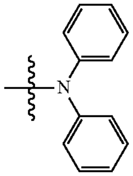 | Cmpd. |
|---|---|---|---|---|---|---|---|---|---|---|
| 14 | | x | | | | | | | | 14-2 |
| 14 | | | x | | | | | | | 14-3 |
| 14 | | | | x | | | | | | 14-4 |
| 14 | | | | | x | | | | | 14-5 |
| 14 | | | | | | x | | | | 14-6 |
| 14 | | | | | | | x | | | 14-7 |
| 14 | | | | | | | | x | | 14-8 |
| 14 | | | | | | | | | x | 14-9 |
| 15 | x | | | | | | | | | 15-1 |
| 15 | | x | | | | | | | | 15-2 |
| 15 | | | x | | | | | | | 15-3 |
| 15 | | | | x | | | | | | 15-4 |
| 15 | | | | | x | | | | | 15-5 |
| 15 | | | | | | x | | | | 15-6 |
| 15 | | | | | | | x | | | 15-7 |
| 15 | | | | | | | | x | | 15-8 |
| 15 | | | | | | | | | x | 15-9 |
| 16 | x | | | | | | | | | 16-1 |
| 16 | | x | | | | | | | | 16-2 |
| 16 | | | x | | | | | | | 16-3 |
| 16 | | | | x | | | | | | 16-4 |
| 16 | | | | | x | | | | | 16-5 |
| 16 | | | | | | x | | | | 16-6 |
| 16 | | | | | | | x | | | 16-7 |
| 16 | | | | | | | | x | | 16-8 |
| 16 | | | | | | | | | x | 16-9 |
| 17 | x | | | | | | | | | 17-1 |
| 17 | | x | | | | | | | | 17-2 |
| 17 | | | x | | | | | | | 17-3 |
| 17 | | | | x | | | | | | 17-4 |
| 17 | | | | | x | | | | | 17-5 |
| 17 | | | | | | x | | | | 17-6 |
| 17 | | | | | | | x | | | 17-7 |
| 17 | | | | | | | | x | | 17-8 |
| 17 | | | | | | | | | x | 17-9 |
| 18 | x | | | | | | | | | 18-1 |
| 18 | | x | | | | | | | | 18-2 |
| 18 | | | x | | | | | | | 18-3 |
| 18 | | | | x | | | | | | 18-4 |
| 18 | | | | | x | | | | | 18-5 |

TABLE 1-continued
| Formula | 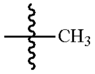 | 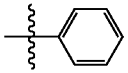 | 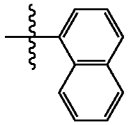 | 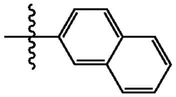 | 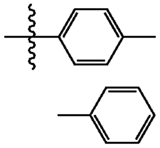 | 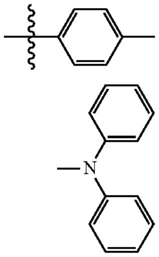 | 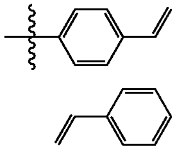 | 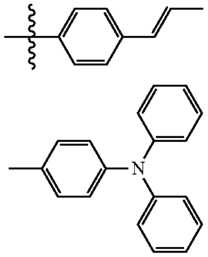 | 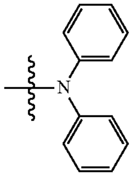 | Cmpd. |
|---|---|---|---|---|---|---|---|---|---|---|
| 18 | | | | | | x | | | | 18-6 |
| 18 | | | | | | | x | | | 18-7 |
| 18 | | | | | | | | x | | 18-8 |
| 18 | | | | | | | | | x | 18-9 |
| 19 | x | | | | | | | | | 19-1 |
| 19 | | x | | | | | | | | 19-2 |
| 19 | | | x | | | | | | | 19-3 |
| 19 | | | | x | | | | | | 19-4 |
| 19 | | | | | x | | | | | 19-5 |
| 19 | | | | | | x | | | | 19-6 |
| 19 | | | | | | | x | | | 19-7 |
| 19 | | | | | | | | x | | 19-8 |
| 19 | | | | | | | | | x | 19-9 |
| 20 | x | | | | | | | | | 20-1 |
| 20 | | x | | | | | | | | 20-2 |
| 20 | | | x | | | | | | | 20-3 |
| 20 | | | | x | | | | | | 20-4 |
| 20 | | | | | x | | | | | 20-5 |
| 20 | | | | | | x | | | | 20-6 |
| 20 | | | | | | | x | | | 20-7 |
| 20 | | | | | | | | x | | 20-8 |
| 20 | | | | | | | | | x | 20-9 |
| 21 | x | | | | | | | | | 21-1 |
| 21 | | x | | | | | | | | 21-2 |
| 21 | | | x | | | | | | | 21-3 |
| 21 | | | | x | | | | | | 21-4 |
| 21 | | | | | x | | | | | 21-5 |
| 21 | | | | | | x | | | | 21-6 |
| 21 | | | | | | | x | | | 21-7 |
| 21 | | | | | | | | x | | 21-8 |
| 21 | | | | | | | | | x | 21-9 |
| 22 | x | | | | | | | | | 22-1 |
| 22 | | x | | | | | | | | 22-2 |
| 22 | | | x | | | | | | | 22-3 |
| 22 | | | | x | | | | | | 22-4 |
| 22 | | | | | x | | | | | 22-5 |
| 22 | | | | | | x | | | | 22-6 |
| 22 | | | | | | | x | | | 22-7 |
| 22 | | | | | | | | x | | 22-8 |
| 22 | | | | | | | | | x | 22-9 |

TABLE 1-continued
| Formula | 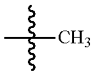 | 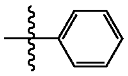 | 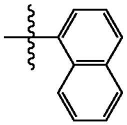 | 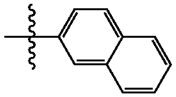 | 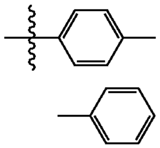 | 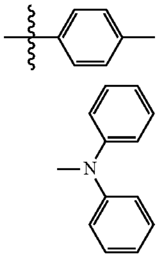 | 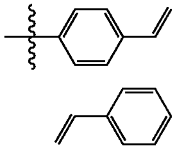 | 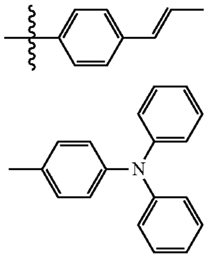 | 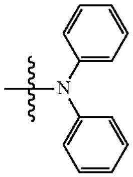 | Cmpd. |
|---|---|---|---|---|---|---|---|---|---|---|
| 23 | x | | | | | | | | | 23-1 |
| 23 | | x | | | | | | | | 23-2 |
| 23 | | | x | | | | | | | 23-3 |
| 23 | | | | x | | | | | | 23-4 |
| 23 | | | | | x | | | | | 23-5 |
| 23 | | | | | | x | | | | 23-6 |
| 23 | | | | | | | x | | | 23-7 |
| 23 | | | | | | | | x | | 23-8 |
| 23 | | | | | | | | | x | 23-9 |
| 24 | x | | | | | | | | | 24-1 |
| 24 | | x | | | | | | | | 24-2 |
| 24 | | | x | | | | | | | 24-3 |
| 24 | | | | x | | | | | | 24-4 |
| 24 | | | | | x | | | | | 24-5 |
| 24 | | | | | | x | | | | 24-6 |
| 24 | | | | | | | x | | | 24-7 |
| 24 | | | | | | | | x | | 24-8 |
| 24 | | | | | | | | | x | 24-9 |
| 25 | x | | | | | | | | | 25-1 |
| 25 | | x | | | | | | | | 25-2 |
| 25 | | | x | | | | | | | 25-3 |
| 25 | | | | x | | | | | | 25-4 |
| 25 | | | | | x | | | | | 25-5 |
| 25 | | | | | | x | | | | 25-6 |
| 25 | | | | | | | x | | | 25-7 |
| 25 | | | | | | | | x | | 25-8 |
| 25 | | | | | | | | | x | 25-9 |
| 26 | x | | | | | | | | | 26-1 |
| 26 | | x | | | | | | | | 26-2 |
| 26 | | | x | | | | | | | 26-3 |
| 26 | | | | x | | | | | | 26-4 |
| 26 | | | | | x | | | | | 26-5 |
| 26 | | | | | | x | | | | 26-6 |
| 26 | | | | | | | x | | | 26-7 |
| 26 | | | | | | | | x | | 26-8 |
| 26 | | | | | | | | | x | 26-9 |
| 27 | x | | | | | | | | | 27-1 |
| 27 | | x | | | | | | | | 27-2 |
| 27 | | | x | | | | | | | 27-3 |
| 27 | | | | x | | | | | | 27-4 |

TABLE 1-continued
| Form-ula | 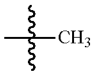 | 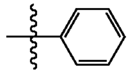 | 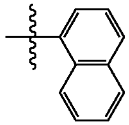 | 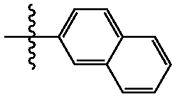 | 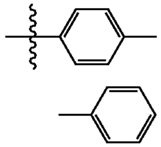 | 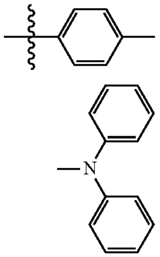 | 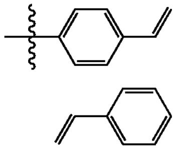 | 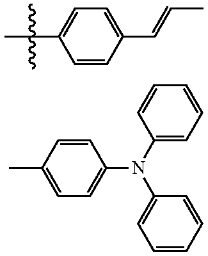 | 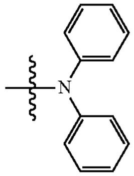 | Cmpd. |
|---|---|---|---|---|---|---|---|---|---|---|
| 27 | | | | | x | | | | | 27-5 |
| 27 | | | | | | x | | | | 27-6 |
| 27 | | | | | | | x | | | 27-7 |
| 27 | | | | | | | | x | | 27-8 |
| 27 | | | | | | | | | x | 27-9 |
| 28 | x | | | | | | | | | 28-1 |
| 28 | | x | | | | | | | | 28-2 |
| 28 | | | x | | | | | | | 28-3 |
| 28 | | | | x | | | | | | 28-4 |
| 28 | | | | | x | | | | | 28-5 |
| 28 | | | | | | x | | | | 28-6 |
| 28 | | | | | | | x | | | 28-7 |
| 28 | | | | | | | | x | | 28-8 |
| 28 | | | | | | | | | x | 28-9 |
| 29 | x | | | | | | | | | 29-1 |
| 29 | | x | | | | | | | | 29-2 |
| 29 | | | x | | | | | | | 29-3 |
| 29 | | | | x | | | | | | 29-4 |
| 29 | | | | | x | | | | | 29-5 |
| 29 | | | | | | x | | | | 29-6 |
| 29 | | | | | | | x | | | 29-7 |
| 29 | | | | | | | | x | | 29-8 |
| 29 | | | | | | | | | x | 29-9 |
| 30 | x | | | | | | | | | 30-1 |
| 30 | | x | | | | | | | | 30-2 |
| 30 | | | x | | | | | | | 30-3 |
| 30 | | | | x | | | | | | 30-4 |
| 30 | | | | | x | | | | | 30-5 |
| 30 | | | | | | x | | | | 30-6 |
| 30 | | | | | | | x | | | 30-7 |
| 30 | | | | | | | | x | | 30-8 |
| 30 | | | | | | | | | x | 30-9 |
| 31 | x | | | | | | | | | 31-1 |
| 31 | | x | | | | | | | | 31-2 |
| 31 | | | x | | | | | | | 31-3 |
| 31 | | | | x | | | | | | 31-4 |
| 31 | | | | | x | | | | | 31-5 |
| 31 | | | | | | x | | | | 31-6 |
| 31 | | | | | | | x | | | 31-7 |
| 31 | | | | | | | | x | | 31-8 |

TABLE 1-continued
| Formula | 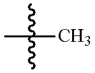 | 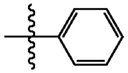 | 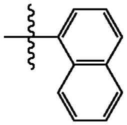 | 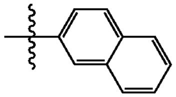 | 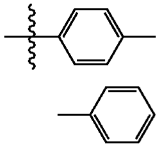 | 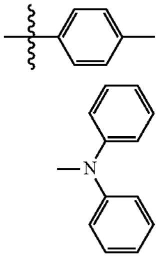 | 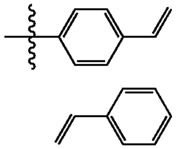 | 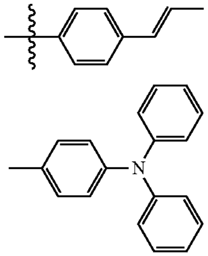 | 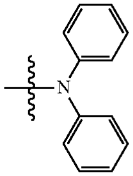 | Cmpd. |
|---|---|---|---|---|---|---|---|---|---|---|
| 31 | | | | | | | | | x | 31-9 |
| 32 | x | | | | | | | | | 32-1 |
| 32 | | x | | | | | | | | 32-2 |
| 32 | | | x | | | | | | | 32-3 |
| 32 | | | | x | | | | | | 32-4 |
| 32 | | | | | x | | | | | 32-5 |
| 32 | | | | | | x | | | | 32-6 |
| 32 | | | | | | | x | | | 32-7 |
| 32 | | | | | | | | x | | 32-8 |
| 32 | | | | | | | | | x | 32-9 |
| 33 | x | | | | | | | | | 33-1 |
| 33 | | x | | | | | | | | 33-2 |
| 33 | | | x | | | | | | | 33-3 |
| 33 | | | | x | | | | | | 33-4 |
| 33 | | | | | x | | | | | 33-5 |
| 33 | | | | | | x | | | | 33-6 |
| 33 | | | | | | | x | | | 33-7 |
| 33 | | | | | | | | x | | 33-8 |
| 33 | | | | | | | | | x | 33-9 |
| 34 | x | | | | | | | | | 34-1 |
| 34 | | x | | | | | | | | 34-2 |
| 34 | | | x | | | | | | | 34-3 |
| 34 | | | | x | | | | | | 34-4 |
| 34 | | | | | x | | | | | 34-5 |
| 34 | | | | | | x | | | | 34-6 |
| 34 | | | | | | | x | | | 34-7 |
| 34 | | | | | | | | x | | 34-8 |
| 34 | | | | | | | | | x | 34-9 |
| 35 | x | | | | | | | | | 35-1 |
| 35 | | x | | | | | | | | 35-2 |
| 35 | | | x | | | | | | | 35-3 |
| 35 | | | | x | | | | | | 35-4 |
| 35 | | | | | x | | | | | 35-5 |
| 35 | | | | | | x | | | | 35-6 |
| 35 | | | | | | | x | | | 35-7 |
| 35 | | | | | | | | x | | 35-8 |
| 35 | | | | | | | | | x | 35-9 |
| 36 | x | | | | | | | | | 36-1 |
| 36 | | x | | | | | | | | 36-2 |
| 36 | | | x | | | | | | | 36-3 |

TABLE 1-continued
| Formula | 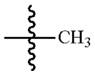 | 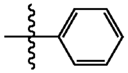 | 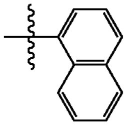 | 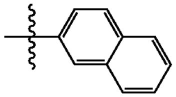 | 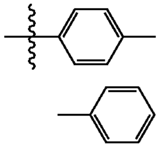 | 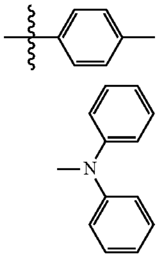 | 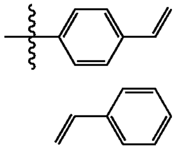 | 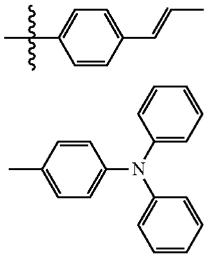 | 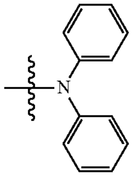 | Cmpd. |
|---|---|---|---|---|---|---|---|---|---|---|
| 36 | | | | x | | | | | | 36-4 |
| 36 | | | | | x | | | | | 36-5 |
| 36 | | | | | | x | | | | 36-6 |
| 36 | | | | | | | x | | | 36-7 |
| 36 | | | | | | | | x | | 36-8 |
| 36 | | | | | | | | | x | 36-9 |
| 37 | x | | | | | | | | | 37-1 |
| 37 | | x | | | | | | | | 37-2 |
| 37 | | | x | | | | | | | 37-3 |
| 37 | | | | x | | | | | | 37-4 |
| 37 | | | | | x | | | | | 37-5 |
| 37 | | | | | | x | | | | 37-6 |
| 37 | | | | | | | x | | | 37-7 |
| 37 | | | | | | | | x | | 37-8 |
| 37 | | | | | | | | | x | 37-9 |
| 38 | x | | | | | | | | | 38-1 |
| 38 | | x | | | | | | | | 38-2 |
| 38 | | | x | | | | | | | 38-3 |
| 38 | | | | x | | | | | | 38-4 |
| 38 | | | | | x | | | | | 38-5 |
| 38 | | | | | | x | | | | 38-6 |
| 38 | | | | | | | x | | | 38-7 |
| 38 | | | | | | | | x | | 38-8 |
| 38 | | | | | | | | | x | 38-9 |
| 39 | x | | | | | | | | | 39-1 |
| 39 | | x | | | | | | | | 39-2 |
| 39 | | | x | | | | | | | 39-3 |
| 39 | | | | x | | | | | | 39-4 |
| 39 | | | | | x | | | | | 39-5 |
| 39 | | | | | | x | | | | 39-6 |
| 39 | | | | | | | x | | | 39-7 |
| 39 | | | | | | | | x | | 39-8 |
| 39 | | | | | | | | | x | 39-9 |
| 40 | x | | | | | | | | | 40-1 |
| 40 | | x | | | | | | | | 40-2 |
| 40 | | | x | | | | | | | 40-3 |
| 40 | | | | x | | | | | | 40-4 |
| 40 | | | | | x | | | | | 40-5 |
| 40 | | | | | | x | | | | 40-6 |
| 40 | | | | | | | x | | | 40-7 |

TABLE 1-continued
| Formula | 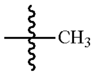 | 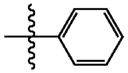 | 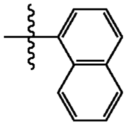 | 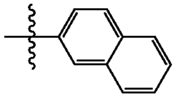 | 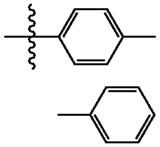 | 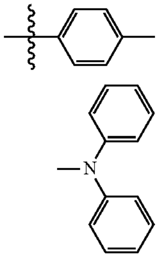 | 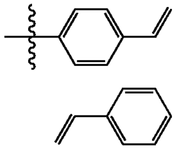 | 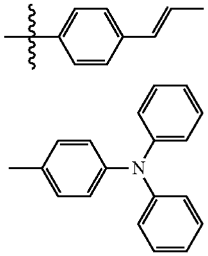 | 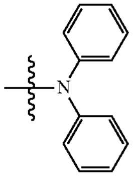 | Cmpd. |
|---|---|---|---|---|---|---|---|---|---|---|
| 40 | | | | | | | | x | | 40-8 |
| 40 | | | | | | | | | x | 40-9 |
| 41 | x | | | | | | | | | 41-1 |
| 41 | | x | | | | | | | | 41-2 |
| 41 | | | x | | | | | | | 41-3 |
| 41 | | | | x | | | | | | 41-4 |
| 41 | | | | | x | | | | | 41-5 |
| 41 | | | | | | x | | | | 41-6 |
| 41 | | | | | | | x | | | 41-7 |
| 41 | | | | | | | | x | | 41-8 |
| 41 | | | | | | | | | x | 41-9 |
| 42 | x | | | | | | | | | 42-1 |
| 42 | | x | | | | | | | | 42-2 |
| 42 | | | x | | | | | | | 42-3 |
| 42 | | | | x | | | | | | 42-4 |
| 42 | | | | | x | | | | | 42-5 |
| 42 | | | | | | x | | | | 42-6 |
| 42 | | | | | | | x | | | 42-7 |
| 42 | | | | | | | | x | | 42-8 |
| 42 | | | | | | | | | x | 42-9 |
| 43 | x | | | | | | | | | 43-1 |
| 43 | | x | | | | | | | | 43-2 |
| 43 | | | x | | | | | | | 43-3 |
| 43 | | | | x | | | | | | 43-4 |
| 43 | | | | | x | | | | | 43-5 |
| 43 | | | | | | x | | | | 43-6 |
| 43 | | | | | | | x | | | 43-7 |
| 43 | | | | | | | | x | | 43-8 |
| 43 | | | | | | | | | x | 43-9 |
| 44 | x | | | | | | | | | 44-1 |
| 44 | | x | | | | | | | | 44-2 |
| 44 | | | x | | | | | | | 44-3 |
| 44 | | | | x | | | | | | 44-4 |
| 44 | | | | | x | | | | | 44-5 |
| 44 | | | | | | x | | | | 44-6 |
| 44 | | | | | | | x | | | 44-7 |
| 44 | | | | | | | | x | | 44-8 |
| 44 | | | | | | | | | x | 44-9 |
| 45 | x | | | | | | | | | 45-1 |
| 45 | | x | | | | | | | | 45-2 |

TABLE 1-continued
| Formula | 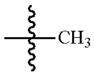 | 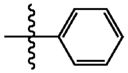 | 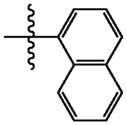 | 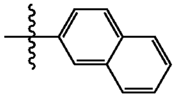 | 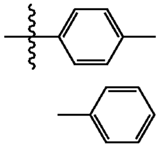 | 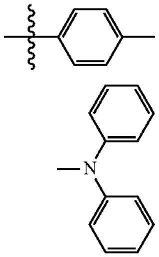 | 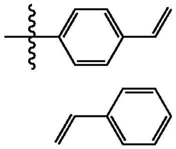 | 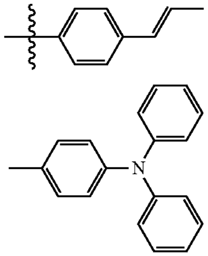 | 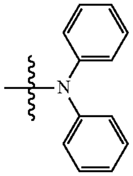 | Cmpd. |
|---|---|---|---|---|---|---|---|---|---|---|
| 45 | | | x | | | | | | | 45-3 |
| 45 | | | | x | | | | | | 45-4 |
| 45 | | | | | x | | | | | 45-5 |
| 45 | | | | | | x | | | | 45-6 |
| 45 | | | | | | | x | | | 45-7 |
| 45 | | | | | | | | x | | 45-8 |
| 45 | | | | | | | | | x | 45-9 |
| 46 | x | | | | | | | | | 46-1 |
| 46 | | x | | | | | | | | 46-2 |
| 46 | | | x | | | | | | | 46-3 |
| 46 | | | | x | | | | | | 46-4 |
| 46 | | | | | x | | | | | 46-5 |
| 46 | | | | | | x | | | | 46-6 |
| 46 | | | | | | | x | | | 46-7 |
| 46 | | | | | | | | x | | 46-8 |
| 46 | | | | | | | | | x | 46-9 |
| 47 | x | | | | | | | | | 47-1 |
| 47 | | x | | | | | | | | 47-2 |
| 47 | | | x | | | | | | | 47-3 |
| 47 | | | | x | | | | | | 47-4 |
| 47 | | | | | x | | | | | 47-5 |
| 47 | | | | | | x | | | | 47-6 |
| 47 | | | | | | | x | | | 47-7 |
| 47 | | | | | | | | x | | 47-8 |
| 47 | | | | | | | | | x | 47-9 |
| 48 | x | | | | | | | | | 48-1 |
| 48 | | x | | | | | | | | 48-2 |
| 48 | | | x | | | | | | | 48-3 |
| 48 | | | | x | | | | | | 48-4 |
| 48 | | | | | x | | | | | 48-5 |
| 48 | | | | | | x | | | | 48-6 |
| 48 | | | | | | | x | | | 48-7 |
| 48 | | | | | | | | x | | 48-8 |
| 48 | | | | | | | | | x | 48-9 |
| 49 | x | | | | | | | | | 49-1 |
| 49 | | x | | | | | | | | 49-2 |
| 49 | | | x | | | | | | | 49-3 |
| 49 | | | | x | | | | | | 49-4 |
| 49 | | | | | x | | | | | 49-5 |
| 49 | | | | | | x | | | | 49-6 |

TABLE 1-continued
| Formula | 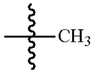 | 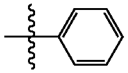 | 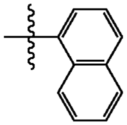 | 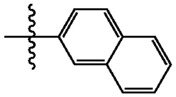 | 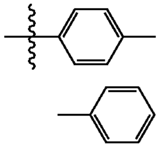 | 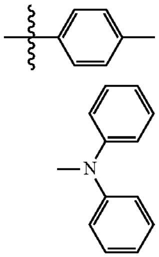 | 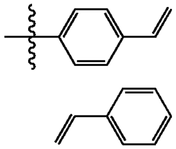 | 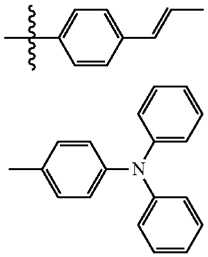 | 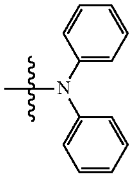 | Cmpd. |
|---|---|---|---|---|---|---|---|---|---|---|
| 49 | | | | | | | x | | | 49-7 |
| 49 | | | | | | | | x | | 49-8 |
| 49 | | | | | | | | | x | 49-9 |
| 50 | x | | | | | | | | | 50-1 |
| 50 | | x | | | | | | | | 50-2 |
| 50 | | | x | | | | | | | 50-3 |
| 50 | | | | x | | | | | | 50-4 |
| 50 | | | | | x | | | | | 50-5 |
| 50 | | | | | | x | | | | 50-6 |
| 50 | | | | | | | x | | | 50-7 |
| 50 | | | | | | | | x | | 50-8 |
| 50 | | | | | | | | | x | 50-9 |
| 51 | x | | | | | | | | | 51-1 |
| 51 | | x | | | | | | | | 51-2 |
| 51 | | | x | | | | | | | 51-3 |
| 51 | | | | x | | | | | | 51-4 |
| 51 | | | | | x | | | | | 51-5 |
| 51 | | | | | | x | | | | 51-6 |
| 51 | | | | | | | x | | | 51-7 |
| 51 | | | | | | | | x | | 51-8 |
| 51 | | | | | | | | | x | 51-9 |
| 52 | x | | | | | | | | | 52-1 |
| 52 | | x | | | | | | | | 52-2 |
| 52 | | | x | | | | | | | 52-3 |
| 52 | | | | x | | | | | | 52-4 |
| 52 | | | | | x | | | | | 52-5 |
| 52 | | | | | | x | | | | 52-6 |
| 52 | | | | | | | x | | | 52-7 |
| 52 | | | | | | | | x | | 52-8 |
| 52 | | | | | | | | | x | 52-9 |
| 53 | x | | | | | | | | | 53-1 |
| 53 | | x | | | | | | | | 53-2 |
| 53 | | | x | | | | | | | 53-3 |
| 53 | | | | x | | | | | | 53-4 |
| 53 | | | | | x | | | | | 53-5 |
| 53 | | | | | | x | | | | 53-6 |
| 53 | | | | | | | x | | | 53-7 |
| 53 | | | | | | | | x | | 53-8 |
| 53 | | | | | | | | | x | 53-9 |
| 54 | x | | | | | | | | | 54-1 |

TABLE 1-continued
| Formula | 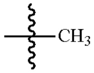 | 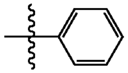 | 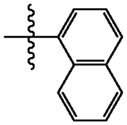 | 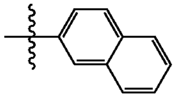 | 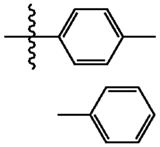 | 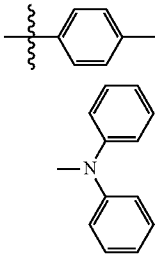 | 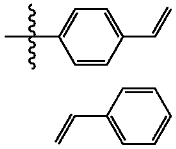 | 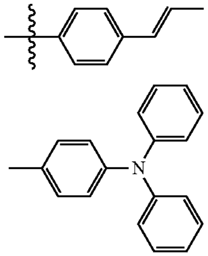 | 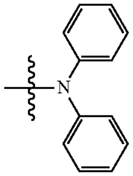 | Cmpd. |
|---|---|---|---|---|---|---|---|---|---|---|
| 54 | | x | | | | | | | | 54-2 |
| 54 | | | x | | | | | | | 54-3 |
| 54 | | | | x | | | | | | 54-4 |
| 54 | | | | | x | | | | | 54-5 |
| 54 | | | | | | x | | | | 54-6 |
| 54 | | | | | | | x | | | 54-7 |
| 54 | | | | | | | | x | | 54-8 |
| 54 | | | | | | | | | x | 54-9 |

TABLE 2
| Formula | 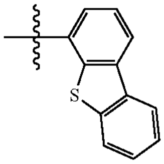 [SMILES: *c1cccc2c1sc1ccccc12] | 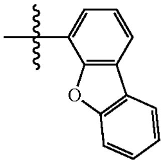 [SMILES: *c1cccc2c1oc1ccccc12] | 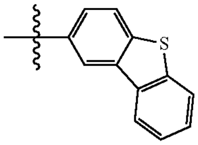 [SMILES: *c1ccc2sc3ccccc3c2c1] | 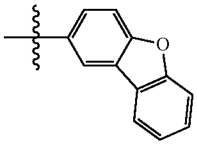 [SMILES: *c1ccc2oc3ccccc3c2c1] | 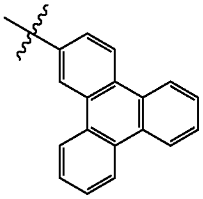 [SMILES: *c1ccc2c3ccccc3c3ccccc3c2c1] | Com-pound |
|---|---|---|---|---|---|---|
| 1 | x | | | | | 1-10 |
| 1 | | x | | | | 1-11 |
| 1 | | | x | | | 1-12 |
| 1 | | | | x | | 1-13 |
| 1 | | | | | x | 1-14 |
| 2 | x | | | | | 2-10 |
| 2 | | x | | | | 2-11 |
| 2 | | | x | | | 2-12 |
| 2 | | | | x | | 2-13 |
| 2 | | | | | x | 2-14 |
| 3 | x | | | | | 3-10 |
| 3 | | x | | | | 3-11 |
| 3 | | | x | | | 3-12 |
| 3 | | | | x | | 3-13 |
| 3 | | | | | x | 3-14 |
| 4 | x | | | | | 4-10 |
| 4 | | x | | | | 4-11 |
| 4 | | | x | | | 4-12 |
| 4 | | | | x | | 4-13 |
| 4 | | | | | x | 4-14 |
| 5 | x | | | | | 5-10 |
| 5 | | x | | | | 5-11 |
| 5 | | | x | | | 5-12 |
| 5 | | | | x | | 5-13 |
| 5 | | | | | x | 5-14 |
| 6 | x | | | | | 6-10 |
| 6 | | x | | | | 6-11 |
| 6 | | | x | | | 6-12 |
| 6 | | | | x | | 6-13 |
| 6 | | | | | x | 6-14 |
| 7 | x | | | | | 7-10 |
| 7 | | x | | | | 7-11 |
| 7 | | | x | | | 7-12 |
| 7 | | | | x | | 7-13 |
| 7 | | | | | x | 7-14 |
| 8 | x | | | | | 8-10 |
| 8 | | x | | | | 8-11 |
| 8 | | | x | | | 8-12 |
| 8 | | | | x | | 8-13 |
| 8 | | | | | x | 8-14 |
| 9 | x | | | | | 9-10 |
| 9 | | x | | | | 9-11 |
| 9 | | | x | | | 9-12 |
| 9 | | | | x | | 9-13 |
| 9 | | | | | x | 9-14 |
| 10 | x | | | | | 10-10 |
| 10 | | x | | | | 10-11 |
| 10 | | | x | | | 10-12 |
| 10 | | | | x | | 10-13 |
| 10 | | | | | x | 10-14 |
| 11 | x | | | | | 11-10 |
| 11 | | x | | | | 11-11 |
| 11 | | | x | | | 11-12 |
| 11 | | | | x | | 11-13 |
| 11 | | | | | x | 11-14 |
| 12 | x | | | | | 12-10 |
| 12 | | x | | | | 12-11 |
| 12 | | | x | | | 12-12 |
| 12 | | | | x | | 12-13 |
| 12 | | | | | x | 12-14 |
| 13 | x | | | | | 13-10 |
| 13 | | x | | | | 13-11 |
| 13 | | | x | | | 13-12 |
| 13 | | | | x | | 13-13 |
| 13 | | | | | x | 13-14 |
| 14 | x | | | | | 14-10 |
| 14 | | x | | | | 14-11 |
| 14 | | | x | | | 14-12 |
| 14 | | | | x | | 14-13 |

TABLE 2-continued
| Formula | 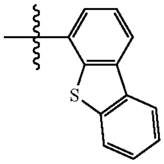 | 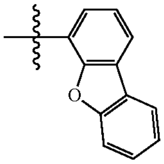 | 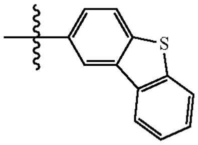 | 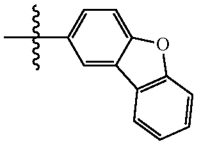 | 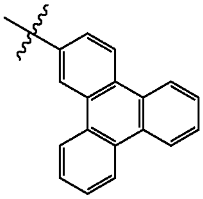 | Com-pound |
|---|---|---|---|---|---|---|
| 14 | | | | | x | 14-14 |
| 15 | x | | | | | 15-10 |
| 15 | | x | | | | 15-11 |
| 15 | | | x | | | 15-12 |
| 15 | | | | x | | 15-13 |
| 15 | | | | | x | 15-14 |
| 16 | x | | | | | 16-10 |
| 16 | | x | | | | 16-11 |
| 16 | | | x | | | 16-12 |
| 16 | | | | x | | 16-13 |
| 16 | | | | | x | 16-14 |
| 17 | x | | | | | 17-10 |
| 17 | | x | | | | 17-11 |
| 17 | | | x | | | 17-12 |
| 17 | | | | x | | 17-13 |
| 17 | | | | | x | 17-14 |
| 18 | x | | | | | 18-10 |
| 18 | | x | | | | 18-11 |
| 18 | | | x | | | 18-12 |
| 18 | | | | x | | 18-13 |
| 18 | | | | | x | 18-14 |
| 19 | x | | | | | 19-10 |
| 19 | | x | | | | 19-11 |
| 19 | | | x | | | 19-12 |
| 19 | | | | x | | 19-13 |
| 19 | | | | | x | 19-14 |
| 20 | x | | | | | 20-10 |
| 20 | | x | | | | 20-11 |
| 20 | | | x | | | 20-12 |
| 20 | | | | x | | 20-13 |
| 20 | | | | | x | 20-14 |
| 21 | x | | | | | 21-10 |
| 21 | | x | | | | 21-11 |
| 21 | | | x | | | 21-12 |
| 21 | | | | x | | 21-13 |
| 21 | | | | | x | 21-14 |
| 22 | x | | | | | 22-10 |
| 22 | | x | | | | 22-11 |
| 22 | | | x | | | 22-12 |
| 22 | | | | x | | 22-13 |
| 22 | | | | | x | 22-14 |
| 23 | x | | | | | 23-10 |
| 23 | | x | | | | 23-11 |
| 23 | | | x | | | 23-12 |
| 23 | | | | x | | 23-13 |
| 23 | | | | | x | 23-14 |
| 24 | x | | | | | 24-10 |
| 24 | | x | | | | 24-11 |
| 24 | | | x | | | 24-12 |
| 24 | | | | x | | 24-13 |
| 24 | | | | | x | 24-14 |
| 25 | x | | | | | 25-10 |
| 25 | | x | | | | 25-11 |
| 25 | | | x | | | 25-12 |
| 25 | | | | x | | 25-13 |
| 25 | | | | | x | 25-14 |
| 26 | x | | | | | 26-10 |
| 26 | | x | | | | 26-11 |
| 26 | | | x | | | 26-12 |
| 26 | | | | x | | 26-13 |
| 26 | | | | | x | 26-14 |
| 27 | x | | | | | 27-10 |
| 27 | | x | | | | 27-11 |
| 27 | | | x | | | 27-12 |
| 27 | | | | x | | 27-13 |
| 27 | | | | | x | 27-14 |
| 28 | x | | | | | 28-10 |
| 28 | | x | | | | 28-11 |
| 28 | | | x | | | 28-12 |

TABLE 2-continued
| Formula | 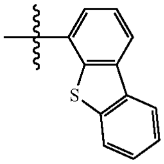 | 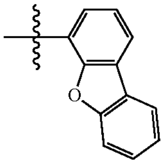 | 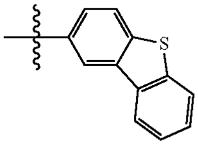 | 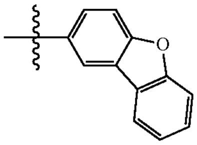 | 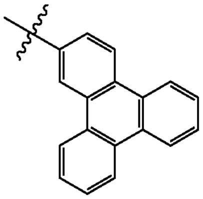 | Com-pound |
|---|---|---|---|---|---|---|
| 28 | | | | x | | 28-13 |
| 28 | | | | | x | 28-14 |
| 29 | x | | | | | 29-10 |
| 29 | | x | | | | 29-11 |
| 29 | | | x | | | 29-12 |
| 29 | | | | x | | 29-13 |
| 29 | | | | | x | 29-14 |
| 30 | x | | | | | 30-10 |
| 30 | | x | | | | 30-11 |
| 30 | | | x | | | 30-12 |
| 30 | | | | x | | 30-13 |
| 30 | | | | | x | 30-14 |
| 31 | x | | | | | 31-10 |
| 31 | | x | | | | 31-11 |
| 31 | | | x | | | 31-12 |
| 31 | | | | x | | 31-13 |
| 31 | | | | | x | 31-14 |
| 32 | x | | | | | 32-10 |
| 32 | | x | | | | 32-11 |
| 32 | | | x | | | 32-12 |
| 32 | | | | x | | 32-13 |
| 32 | | | | | x | 32-14 |
| 33 | x | | | | | 33-10 |
| 33 | | x | | | | 33-11 |
| 33 | | | x | | | 33-12 |
| 33 | | | | x | | 33-13 |
| 33 | | | | | x | 33-14 |
| 34 | x | | | | | 34-10 |
| 34 | | x | | | | 34-11 |
| 34 | | | x | | | 34-12 |
| 34 | | | | x | | 34-13 |
| 34 | | | | | x | 34-14 |
| 35 | x | | | | | 35-10 |
| 35 | | x | | | | 35-11 |
| 35 | | | x | | | 35-12 |
| 35 | | | | x | | 35-13 |
| 35 | | | | | x | 35-14 |
| 36 | x | | | | | 36-10 |
| 36 | | x | | | | 36-11 |
| 36 | | | x | | | 36-12 |
| 36 | | | | x | | 36-13 |
| 36 | | | | | x | 36-14 |
| 37 | x | | | | | 37-10 |
| 37 | | x | | | | 37-11 |
| 37 | | | x | | | 37-12 |
| 37 | | | | x | | 37-13 |
| 37 | | | | | x | 37-14 |
| 38 | x | | | | | 38-10 |
| 38 | | x | | | | 38-11 |
| 38 | | | x | | | 38-12 |
| 38 | | | | x | | 38-13 |
| 38 | | | | | x | 38-14 |
| 39 | x | | | | | 39-10 |
| 39 | | x | | | | 39-11 |
| 39 | | | x | | | 39-12 |
| 39 | | | | x | | 39-13 |
| 39 | | | | | x | 39-14 |
| 40 | x | | | | | 40-10 |
| 40 | | x | | | | 40-11 |
| 40 | | | x | | | 40-12 |
| 40 | | | | x | | 40-13 |
| 40 | | | | | x | 40-14 |
| 41 | x | | | | | 41-10 |
| 41 | | x | | | | 41-11 |
| 41 | | | x | | | 41-12 |
| 41 | | | | x | | 41-13 |
| 41 | | | | | x | 41-14 |
| 42 | x | | | | | 42-10 |
| 42 | | x | | | | 42-11 |

TABLE 2-continued
| Formula | 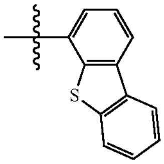 | 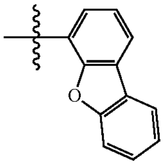 | 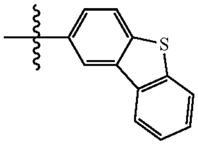 | 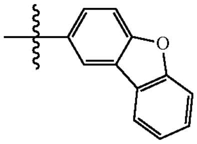 | 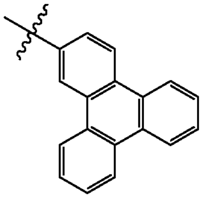 | Com-pound |
|---|---|---|---|---|---|---|
| 42 | | | x | | | 42-12 |
| 42 | | | | x | | 42-13 |
| 42 | | | | | x | 42-14 |
| 43 | x | | | | | 43-10 |
| 43 | | x | | | | 43-11 |
| 43 | | | x | | | 43-12 |
| 43 | | | | x | | 43-13 |
| 43 | | | | | x | 43-14 |
| 44 | x | | | | | 44-10 |
| 44 | | x | | | | 44-11 |
| 44 | | | x | | | 44-12 |
| 44 | | | | x | | 44-13 |
| 44 | | | | | x | 44-14 |
| 45 | x | | | | | 45-10 |
| 45 | | x | | | | 45-11 |
| 45 | | | x | | | 45-12 |
| 45 | | | | x | | 45-13 |
| 45 | | | | | x | 45-14 |
| 46 | x | | | | | 46-10 |
| 46 | | x | | | | 46-11 |
| 46 | | | x | | | 46-12 |
| 46 | | | | x | | 46-13 |
| 46 | | | | | x | 46-14 |
| 47 | x | | | | | 47-10 |
| 47 | | x | | | | 47-11 |
| 47 | | | x | | | 47-12 |
| 47 | | | | x | | 47-13 |
| 47 | | | | | x | 47-14 |
| 48 | x | | | | | 48-10 |
| 48 | | x | | | | 48-11 |
| 48 | | | x | | | 48-12 |
| 48 | | | | x | | 48-13 |
| 48 | | | | | x | 48-14 |
| 49 | x | | | | | 49-10 |
| 49 | | x | | | | 49-11 |
| 49 | | | x | | | 49-12 |
| 49 | | | | x | | 49-13 |
| 49 | | | | | x | 49-14 |
| 50 | x | | | | | 50-10 |
| 50 | | x | | | | 50-11 |
| 50 | | | x | | | 50-12 |
| 50 | | | | x | | 50-13 |
| 50 | | | | | x | 50-14 |
| 51 | x | | | | | 51-10 |
| 51 | | x | | | | 51-11 |
| 51 | | | x | | | 51-12 |
| 51 | | | | x | | 51-13 |
| 51 | | | | | x | 51-14 |
| 52 | x | | | | | 52-10 |
| 52 | | x | | | | 52-11 |
| 52 | | | x | | | 52-12 |
| 52 | | | | x | | 52-13 |
| 52 | | | | | x | 52-14 |
| 53 | x | | | | | 53-10 |
| 53 | | x | | | | 53-11 |
| 53 | | | x | | | 53-12 |
| 53 | | | | x | | 53-13 |
| 53 | | | | | x | 53-14 |
| 54 | x | | | | | 54-10 |
| 54 | | x | | | | 54-11 |
| 54 | | | x | | | 54-12 |
| 54 | | | | x | | 54-13 |
| 54 | | | | | x | 54-14 |

In one aspect, the triplet energy of the

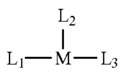

moiety is higher than 450 nm.

In another aspect, the compound has a luminescence lifetime having a long component of more than 0.1 microseconds.

A first device comprising an organic light emitting device is also provided. The first device further comprises an anode, a cathode, and an organic layer, disposed between the anode and the cathode. The organic layer comprises a compound comprising a ligand L having Formula I, as described above.

X is C or N. R is selected from alkyl, alkenyl, alkynyl, amino, alkoxy, silyl, phosphino, mercaptyl, aryl or heteroaryl. $R_2$ and $R_3$ may represent mono, di, tri, or tetra substitutions. $R_2$ and $R_3$ are independently selected from the group consisting of hydrogen, alkyl, alkoxy, amino, alkenyl, alkynyl, aryl and heteroaryl. The ligand L is coordinated to a metal M through coordinating atom X. M is a transition metal. The ligand L is optionally linked to a second ligand, which is also coordinated to the metal M.

In one aspect, the metal M is four coordinate. Preferably, the metal M is a $3^{rd}$ row transition metal. More preferably, M is Pt.

In another aspect, $R_2$ and $R_3$ are fused cyclic or heterocyclic rings.

In one aspect, the compound has the formula:

Formula II

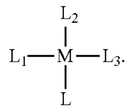

$L_1$, $L_2$, and $L_3$ are independently C, N, O, Si, P, S, or Se coordinating ligands to the metal M.

In another aspect, one of $L_1$, $L_2$, and $L_3$ is anthracenyl.

In one aspect, the compound has the formula:

Formula III

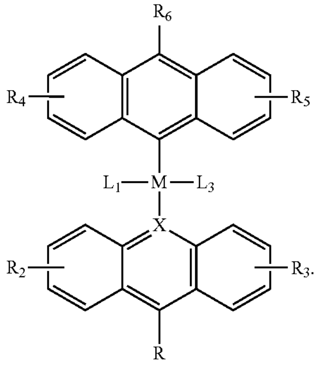

$R_6$ is selected from alkyl, alkenyl, alkynyl, amino, alkoxy, silyl, phosphino, mercaptyl, aryl or heteroaryl. $R_4$ and $R_5$ may represent mono, di, tri, or tetra substitutions. $R_4$ and $R_5$ are independently selected from the group consisting of hydrogen, alkyl, alkoxy, amino, alkenyl, alkynyl, aryl and heteroaryl.

In one aspect, the compound is neutral. The compound is preferably neutral so that vacuum thermal evaporation can be used as a method of device fabrication. Without being bound by theory, it is believed that devices with neutral compounds may also be more stable. In another aspect, the compound is charged.

In one aspect, R is aryl or heteroaryl. In another aspect, R is selected from the group consisting of:

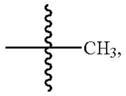
,
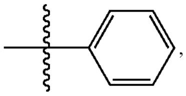
,
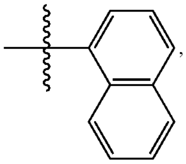
,
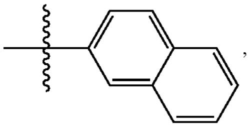
,
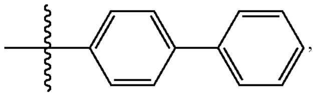
,
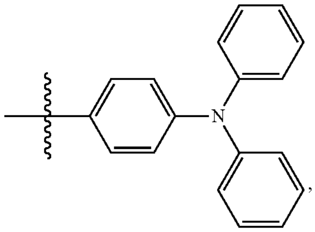
,
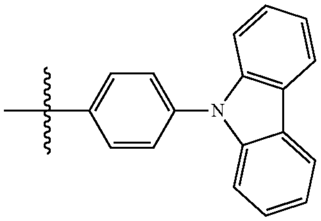

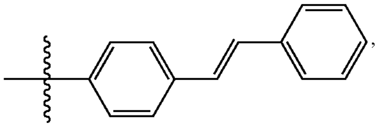
,
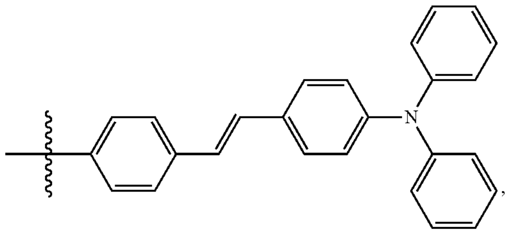
,
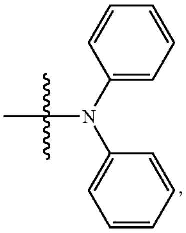
,
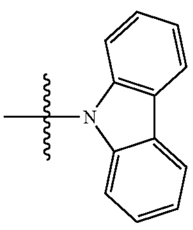

-continued

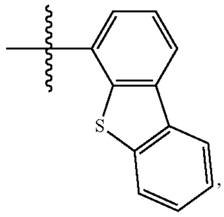
,
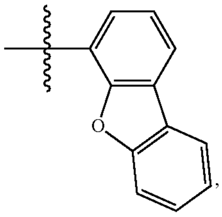
,
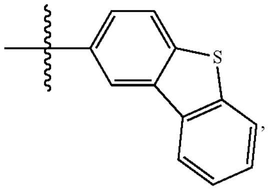
,
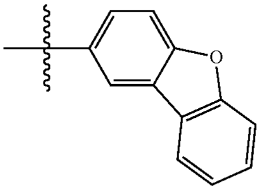
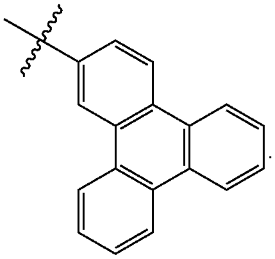
.

In one aspect, any two of L, $L_1$, $L_2$, and $L_3$ are linked together to form a bidentate ligand. For example, at least one of $L_1$ and $L_2$, $L_2$ and $L_3$, $L_1$ and L, or $L_3$ and L are linked together to form a bidentate ligand. In another aspect, at least one of the bidentate ligands forms a 5-member cyclometallating ring with M.

In one aspect, any three of L, $L_1$, $L_2$, and $L_3$ are linked together to form a tridentate ligand. For example, one of $L_1$, $L_2$, and $L_3$ or $L_1$, L and $L_3$ are linked together to form a tridentate ligand. In another aspect, the tridentate ligand forms at least one 5-member cyclometallating ring with M.

Specific examples of first device comprising these compounds, which themselves comprise an anthracene or acridine ligand, are provided. In particular, the compound is selected from the group consisting of:

Compound 1G

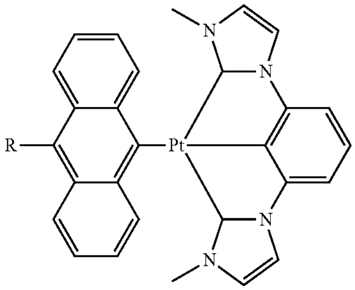

-continued

Compound 2G

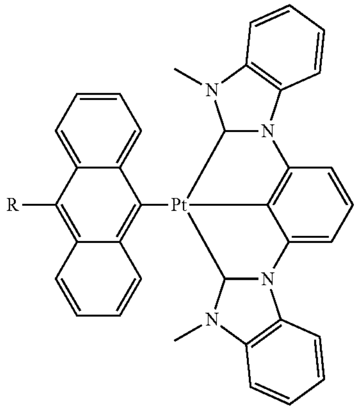

Compound 3G

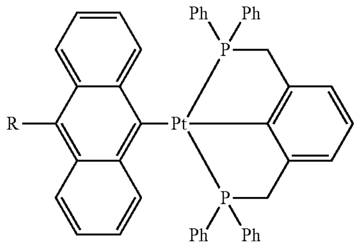

Compound 4G

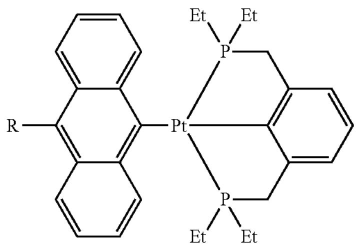

Compound 5G

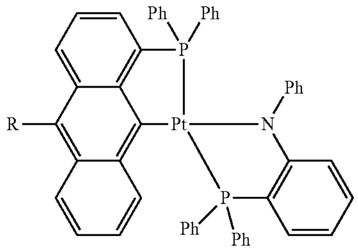

Compound 6G

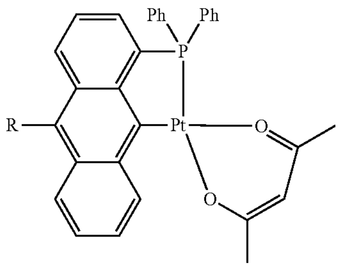

-continued
Compound 7G
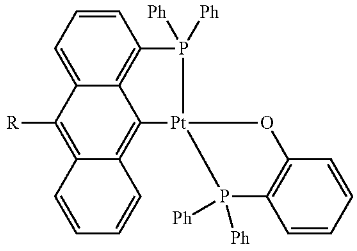
Compound 8G
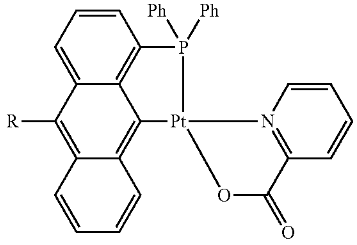
Compound 9G
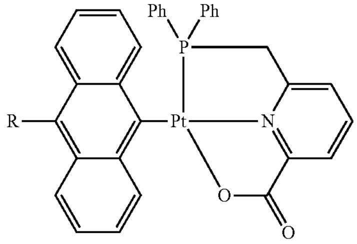
Compound 10G
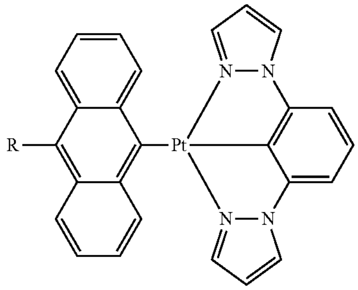
Compound 11G
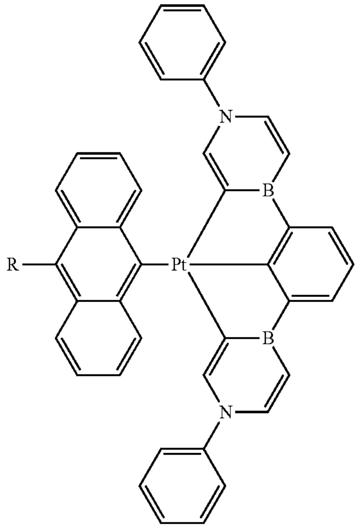
-continued
Compound 12G
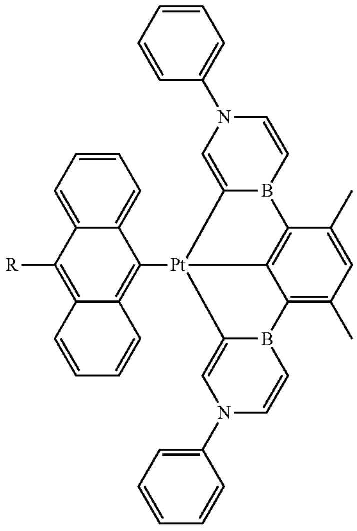
Compound 13G
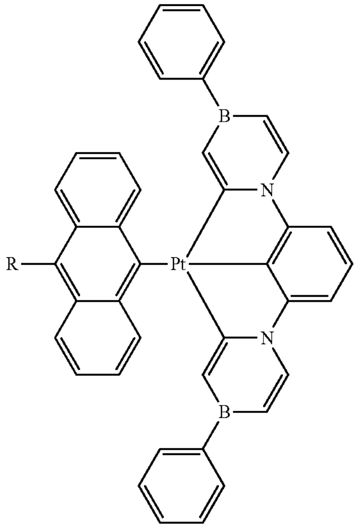
Compound 14G
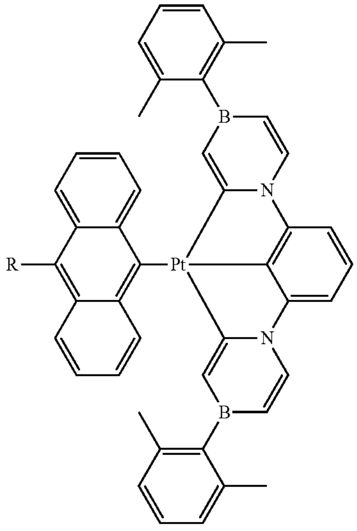

-continued
Compound 15G
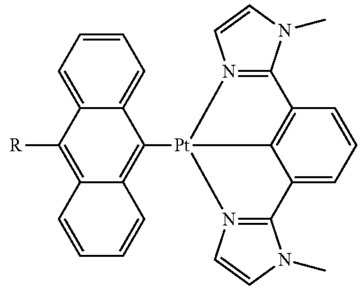
Compound 16G
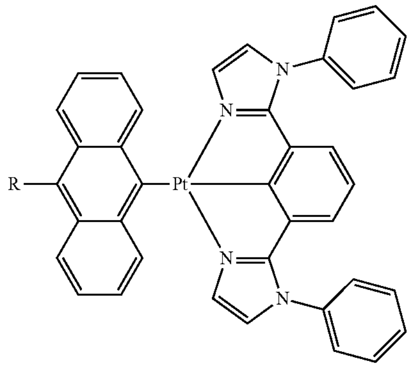
Compound 17G
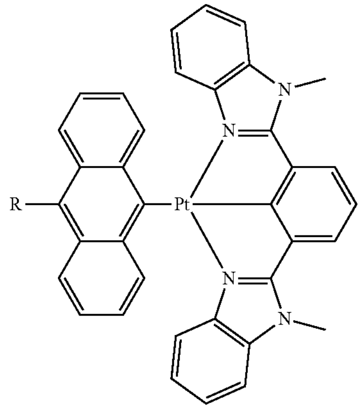
Compound 18G
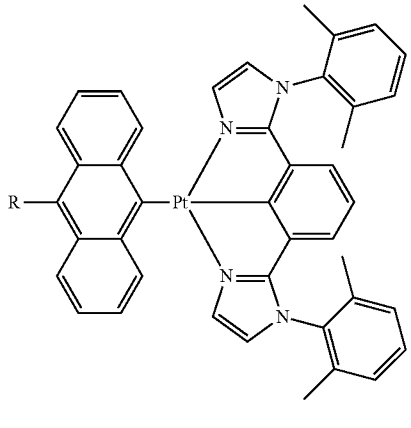
-continued
Compound 19G
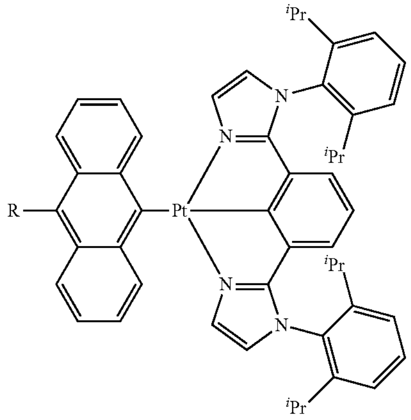
Compound 20G
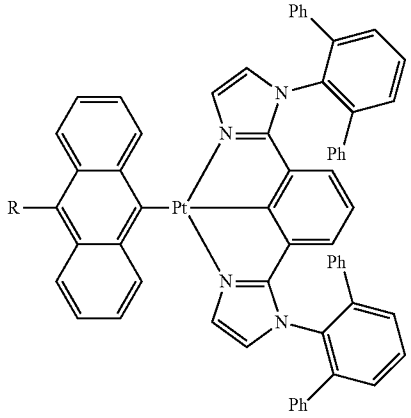
Compound 21G
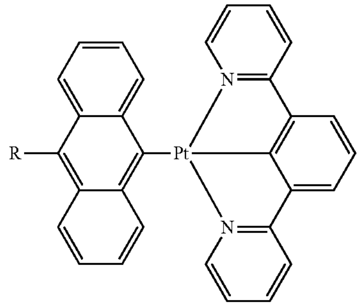
Compound 22G
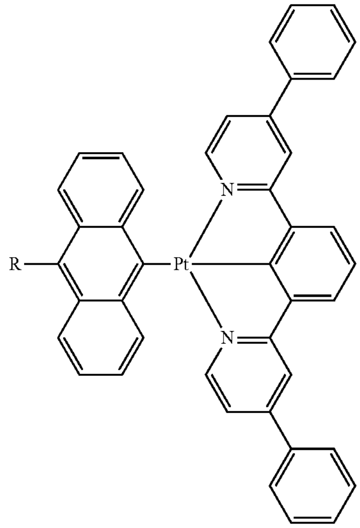

-continued
Compound 23G
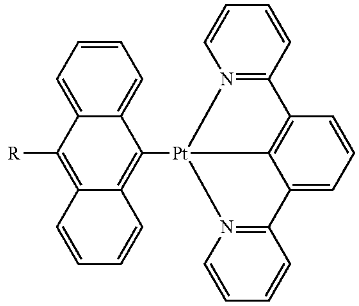
Compound 24G
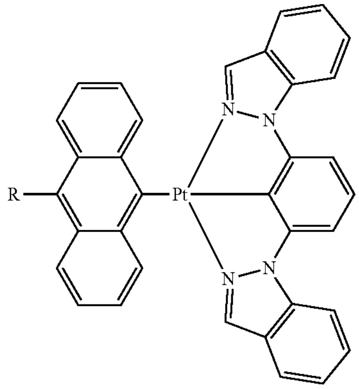
Compound 25G
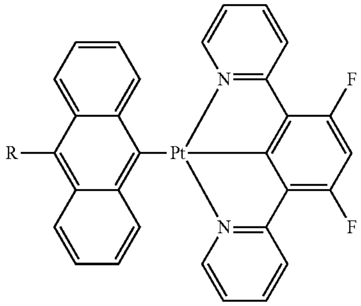
Compound 26G
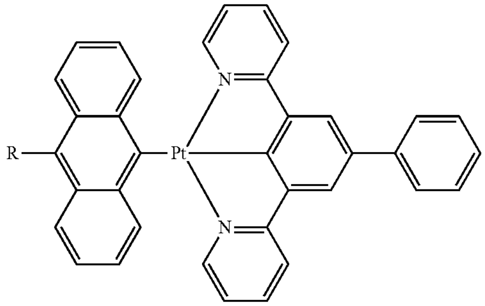
-continued
Compound 27G
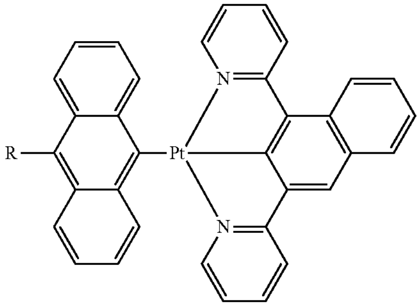
Compound 28G
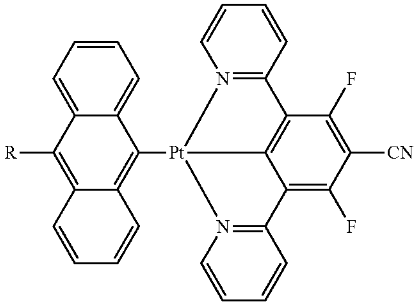
Comppund 29G
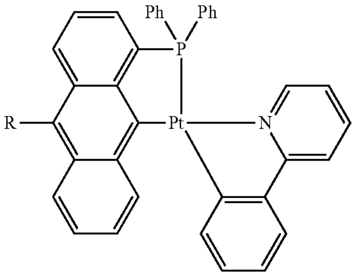
Compound 30G
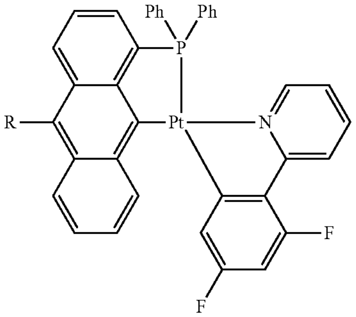
Compound 31G
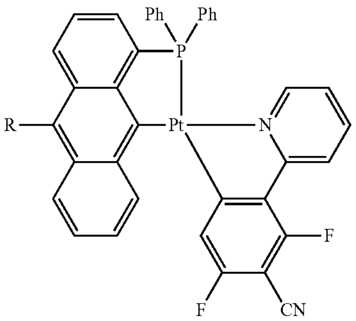

-continued
Compound 32G
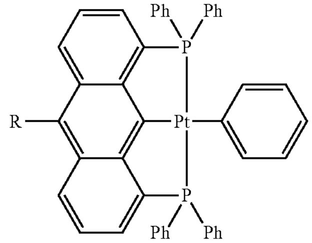
Compound 33G
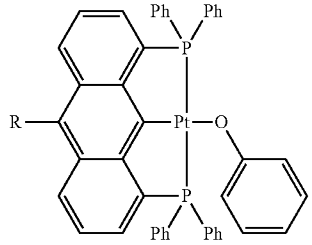
Compound 34G
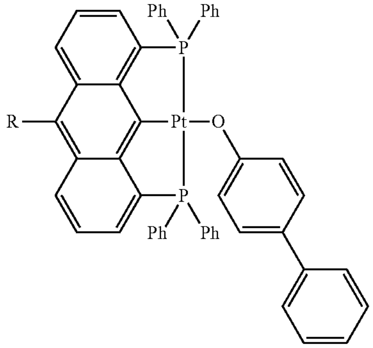
Compound 35G
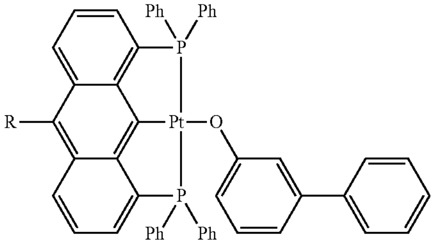
Compound 36G
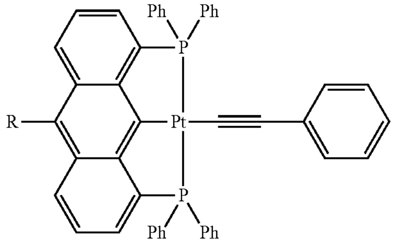
Compound 37G
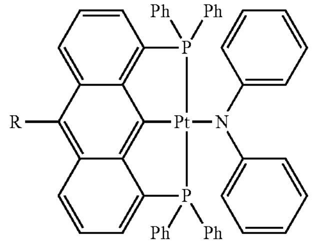
-continued
Compound 38G
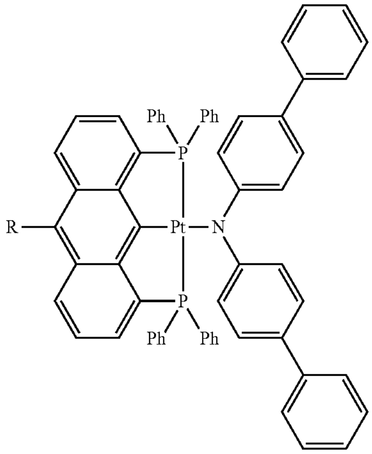
Compound 39G
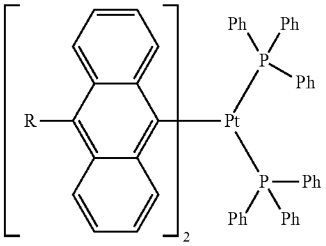
Compound 40G
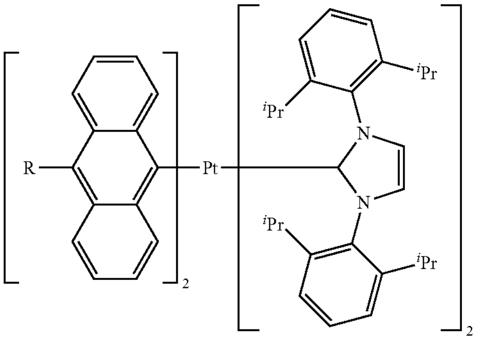
Compound 41G
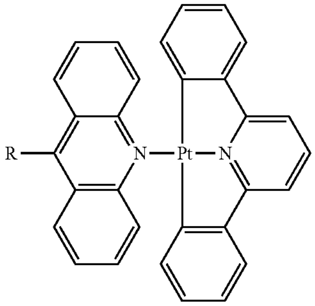

-continued
Compound 42G
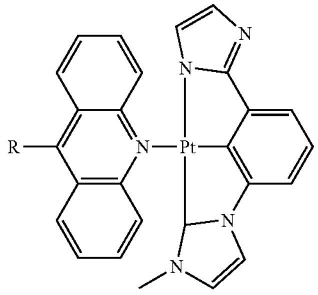
Compound 43G
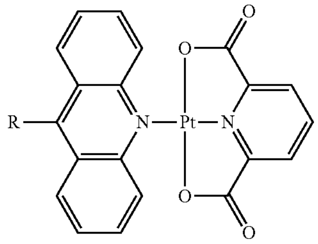
Compound 44G
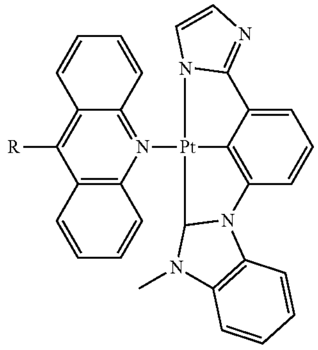
Compound 45G
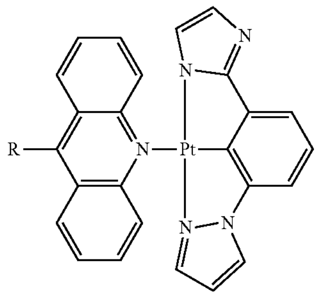
Compound 46G
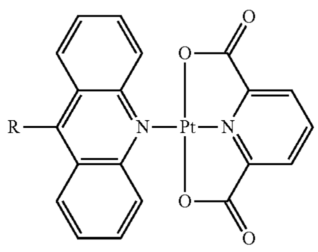
-continued
Compound 47G
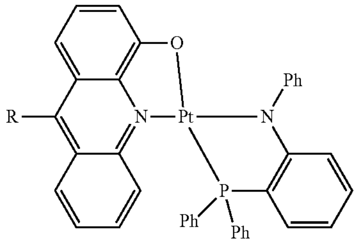
Compound 48G
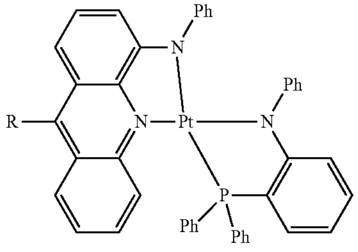
Compound 49G
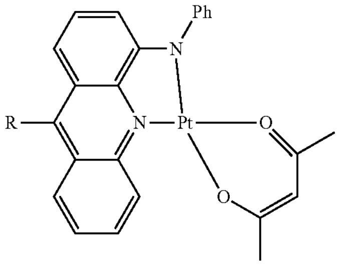
Compound 50G
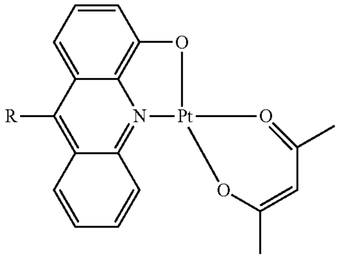
Compound 51G
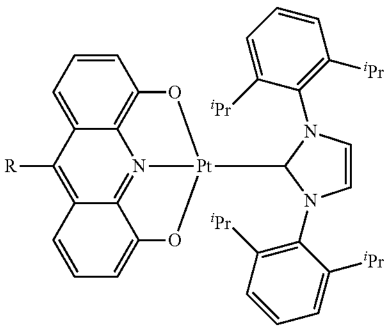

-continued

Compound 52G

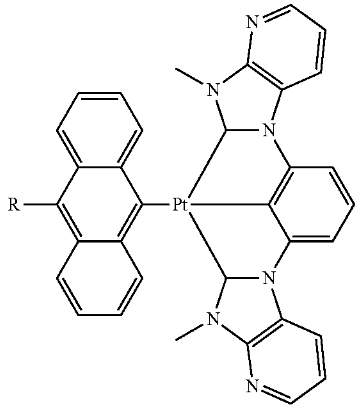

Compound 53G

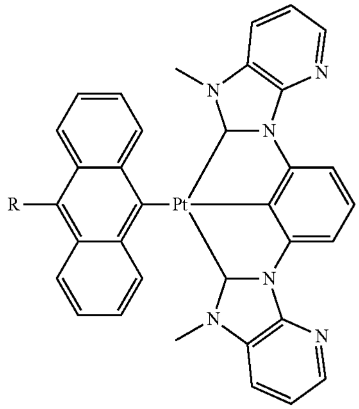

Compound 54G

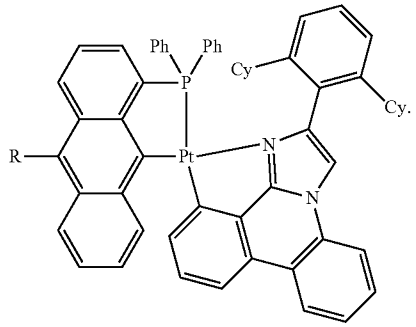

Particularly preferred compounds include compounds selected from the group consisting of Compound 1-1-Compound 54-14, as shown in Tables 1 and 2.

In one aspect, the organic layer is an emissive layer and the compound is an emissive dopant.

In one aspect, the first device is a consumer product. In another aspect, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in embodiments of the present invention is not particularly limited, and any compound may be used as long as the compound is typically used as a hole injecting/transporting material. Examples of the material include, but are not limited to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

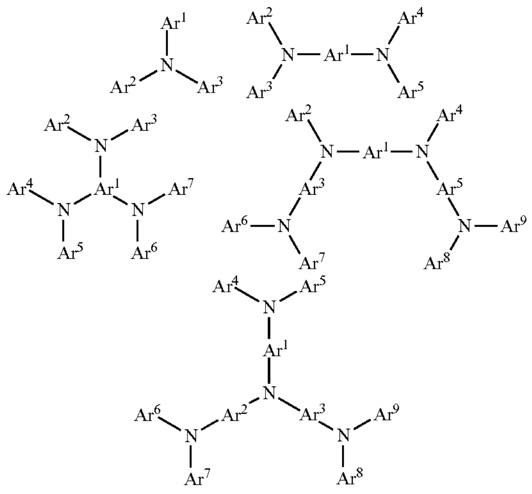

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

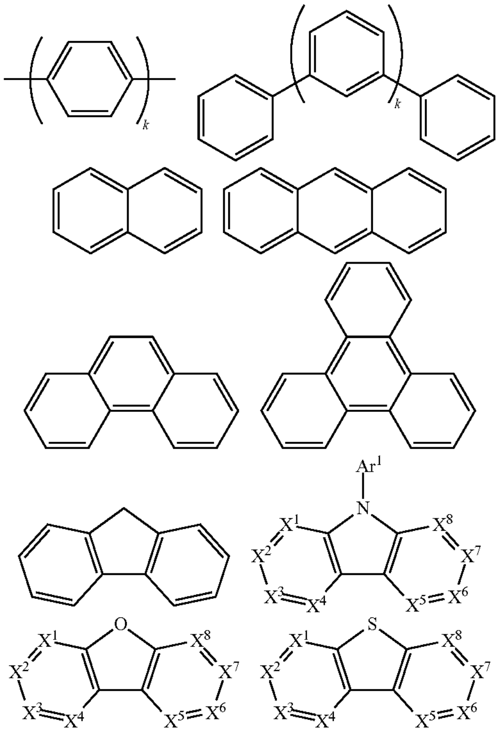

k is an integer from 1 to 20; $X^1$ to $X^8$ is CH or N; $Ar^1$ has the same group defined above.

Examples of metal complexes used in HIL or HTL include, but are not limited to the following general formula:

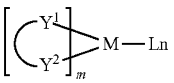

M is a metal, having an atomic weight greater than 40; $(Y^1-Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device in embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

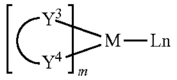

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

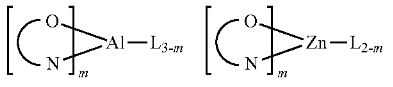

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

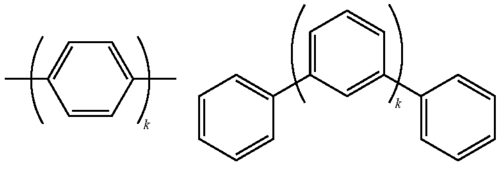

-continued

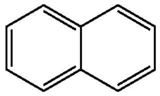
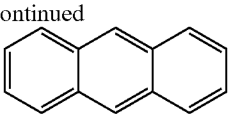
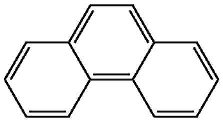
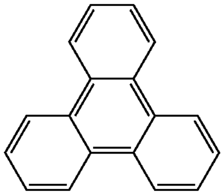
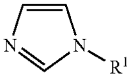
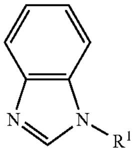
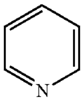
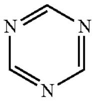
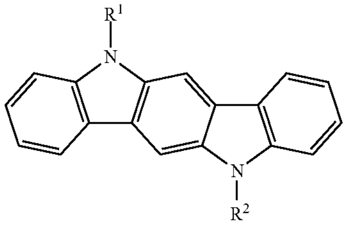
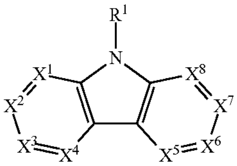
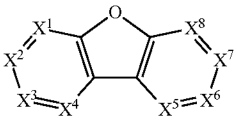
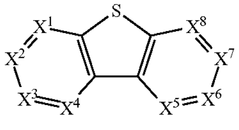
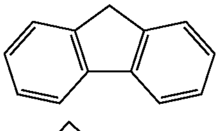
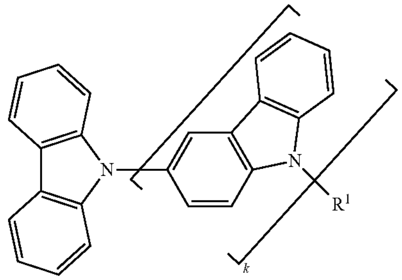
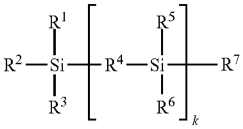
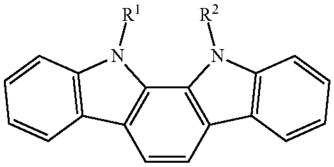

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

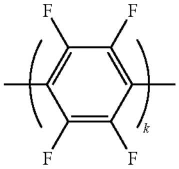
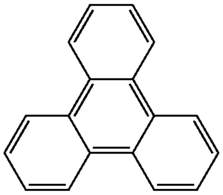
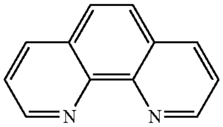
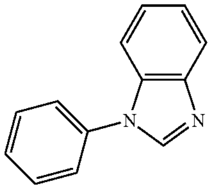
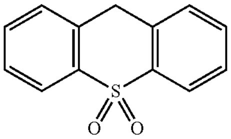
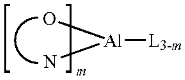

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

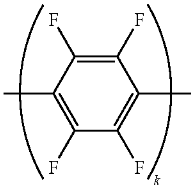
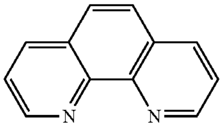
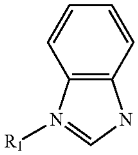
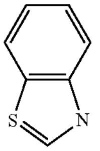
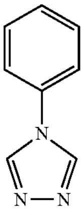
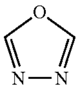
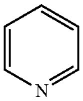

-continued

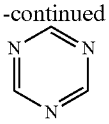

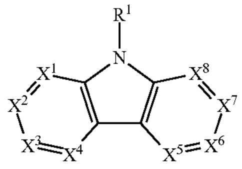

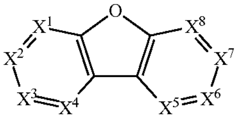

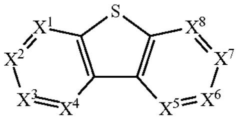

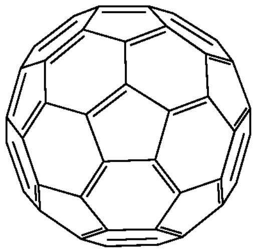

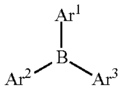

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in ETL contains, but are not limited to the following general formula:

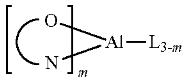

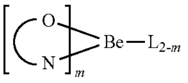

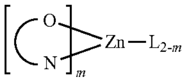

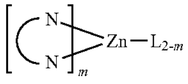

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
|---|---|---|
| | Hole injection materials | |
| Phthalocyanine and porphryin compounds | 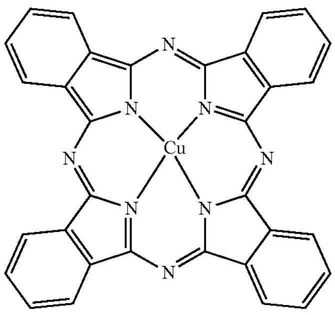 | Appl. Phys. Lett. 69, 2160 (1996) |

TABLE 3-continued
| MATERIAL | EXAMPLES OF MATERIAL | PUBLICATIONS |
| --- | --- | --- |
| Starburst triarylamines | 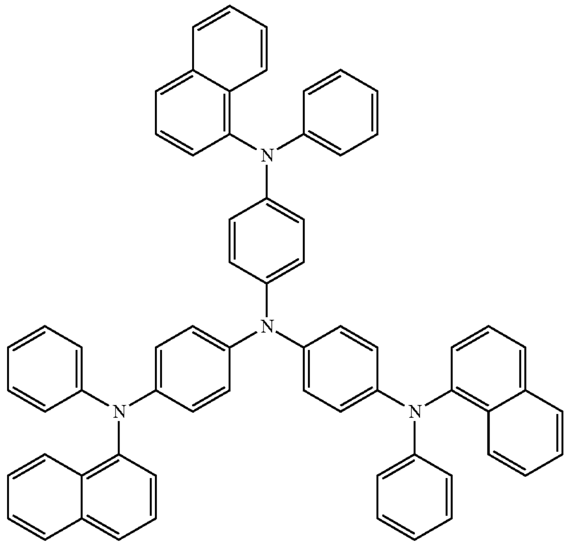 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[-CH_xF_y-]-_n$ | Appl. Phys. Lett. 78, 673 (2001) |
| Conducting polymers (e.g., PEDOT:PSS, polyaniline, polypthiophene) | 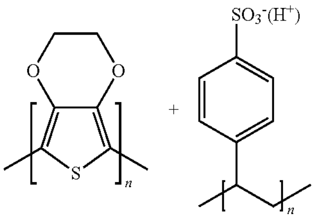 | Synth. Met. 87, 171 (1997) WO2007002683 |
| Phosphonic acid and sliane SAMs | 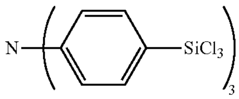 | US20030162053 |
| Triarylamine or polythiophene polymers with conductivity dopants | 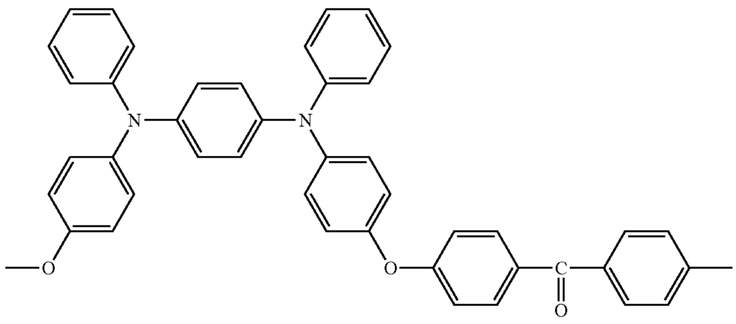 and | EA01725079A1 |

TABLE 3-continued
| MATERIAL | EXAMPLES OF MATERIAL | PUBLICATIONS |
| --- | --- | --- |
| | 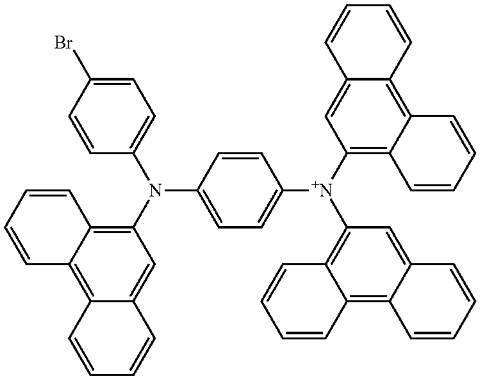 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 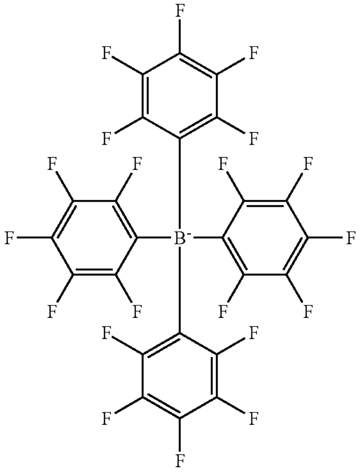 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 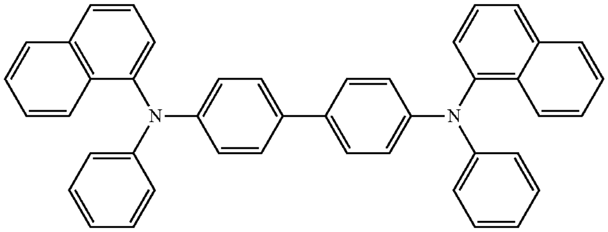 + $MoO_x$ | SID Symposium Digest, 37, 923 (2006) WO2009018009 |
| p-type semiconducting organic complexes | 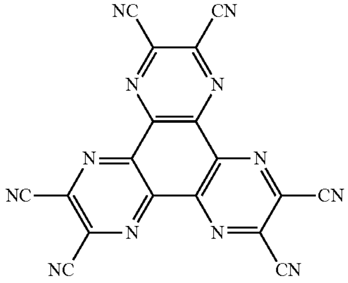 [SMILES: N#Cc1nc2c3nc(C#N)c(C#N)nc3c3nc(C#N)c(C#N)nc3c2nc1C#N] | US20020158242 |

TABLE 3-continued
| MATERIAL | EXAMPLES OF MATERIAL | PUBLICATIONS |
|---|---|---|
| Metal organometallic complexes | 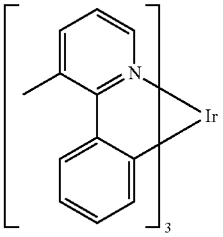 | US20060240279 |
| Cross-linkable compounds | 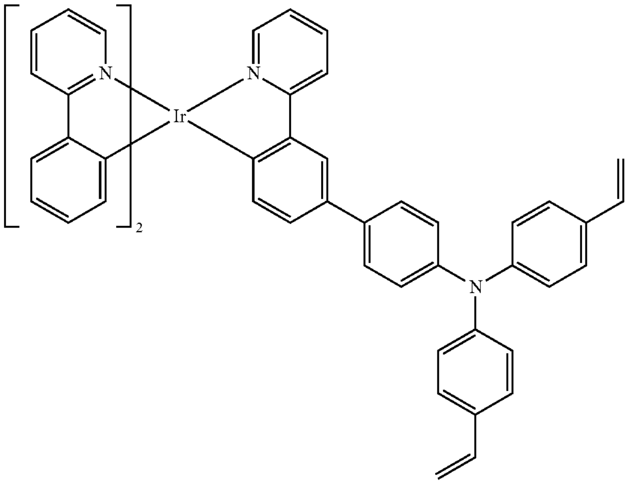 | US20080220265 |
| | Hole transporting materials | |
| Triarylamines (e.g., TPD, α-NPD) | 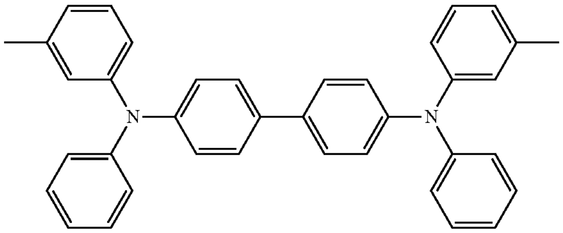 | Appl. Phys. Lett. 51, 913 (1987) |
| | 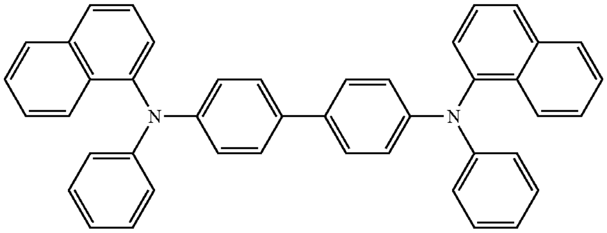 [SMILES: c1ccc(N(c2ccc(-c3ccc(N(c4ccccc4)c4cccc5ccccc45)cc3)cc2)c2cccc3ccccc23)cc1] | US5061569 |

TABLE 3-continued
| MATERIAL | EXAMPLES OF MATERIAL | PUBLICATIONS |
| --- | --- | --- |
| | 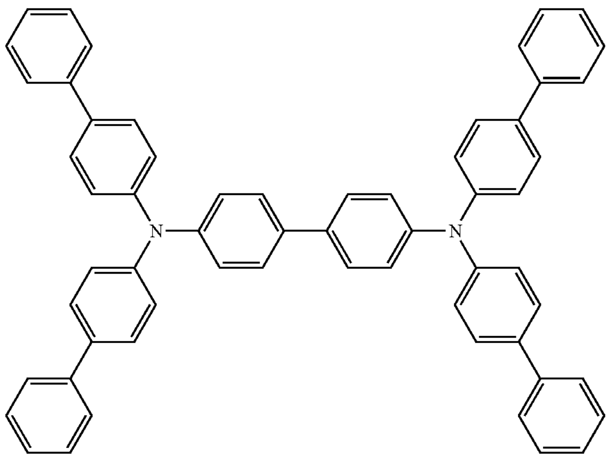 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 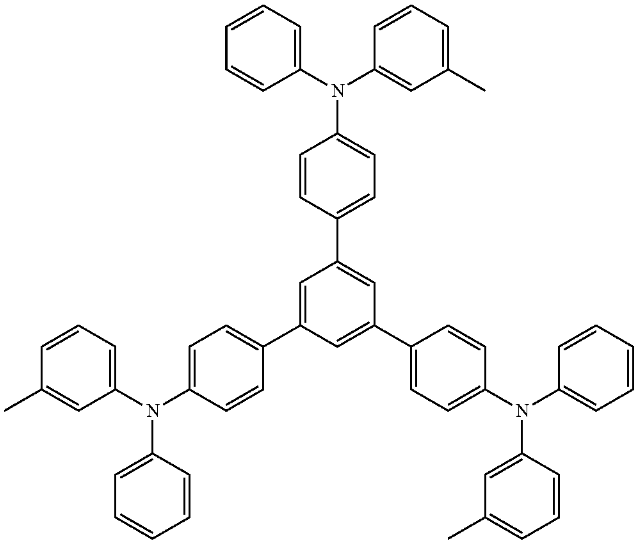 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 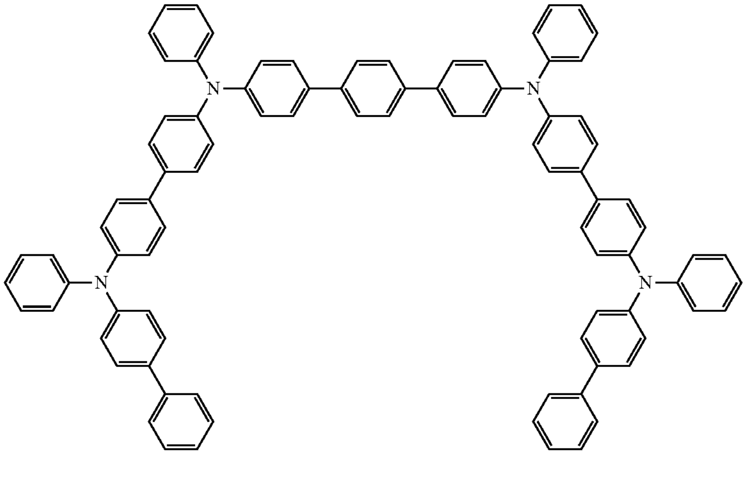 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 3-continued
| MATERIAL | EXAMPLES OF MATERIAL | PUBLICATIONS |
|---|---|---|
| | 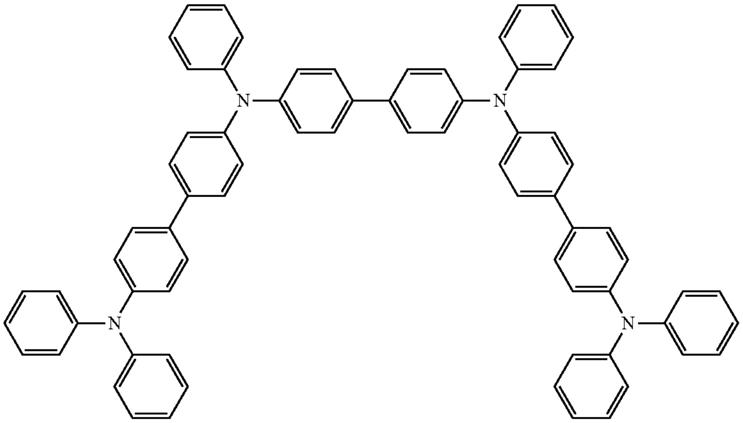 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 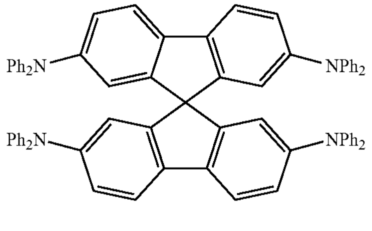 | Synth. Met. 91, 209 (1997) |
| Arylamine carbazole compounds | 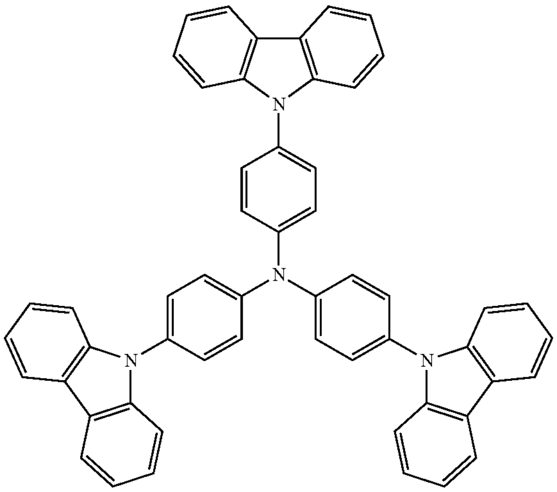 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/(di)benzofuran | 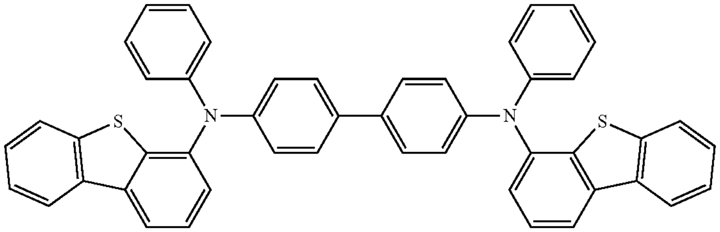 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |

TABLE 3-continued
| MATERIAL | EXAMPLES OF MATERIAL | PUBLICATIONS |
|---|---|---|
| Indolocarbazoles | 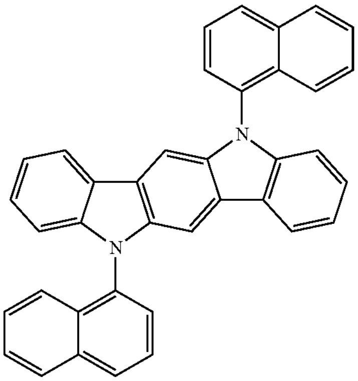 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 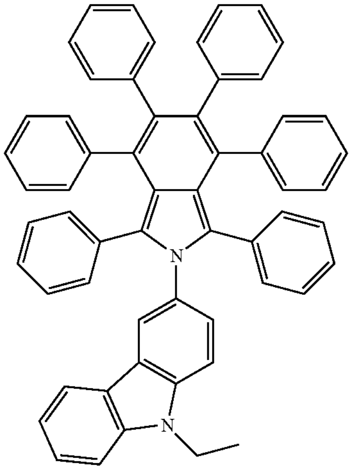 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 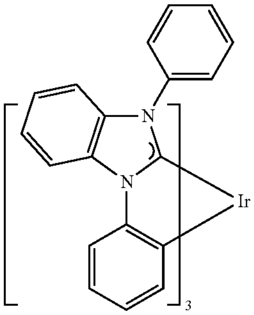 | US20080018221 |
| Phosphorescent OLED host materials<br>Red hosts | | |
| Arylcarbazoles | 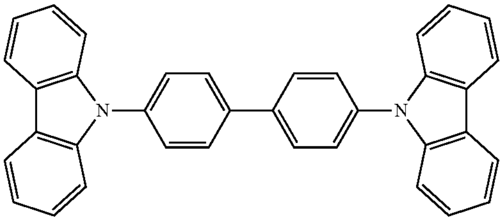 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 3-continued
| MATERIAL | EXAMPLES OF MATERIAL | PUBLICATIONS |
|---|---|---|
| Metal 8-hydroxyquinolates (e.g., $Alq_3$, BAlq) | 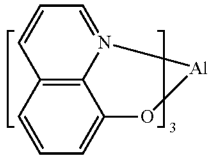 | Nature 395, 151 (1998) |
| | 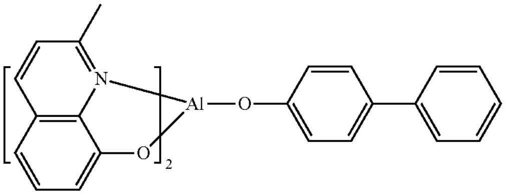 | US20060202194 |
| | 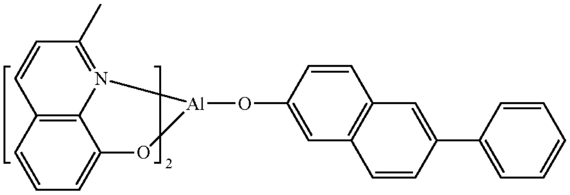 | WO2005014551 |
| | 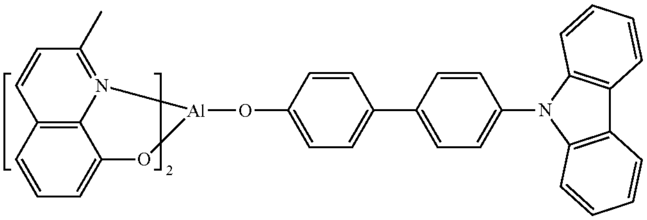 | WO2006072002 |
| Metal phenoxybenzothiazole compounds | 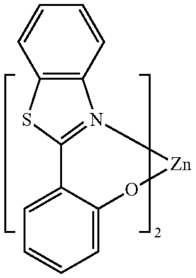 | Appl. Phys. Lett. 90, 123509 (2007) |
| Conjugated oligomers and polymers (e.g., polyfluorene) | 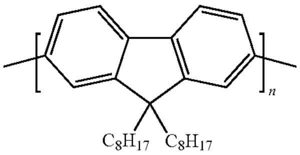 | Org. Electron. 1, 15 (2000) |
| Aromatic fused rings | 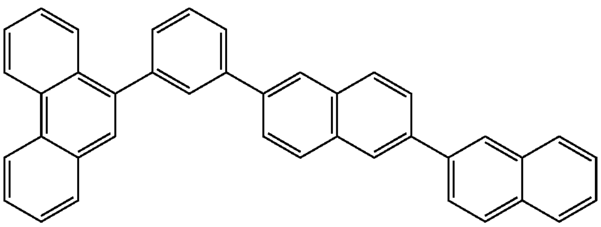 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE 3-continued
| MATERIAL | EXAMPLES OF MATERIAL | PUBLICATIONS |
|---|---|---|
| Zinc complexes | 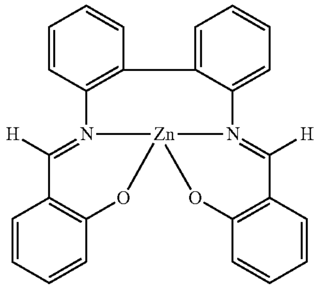 | WO2009062578 |
| | Green hosts | |
| Arylcarbazoles | 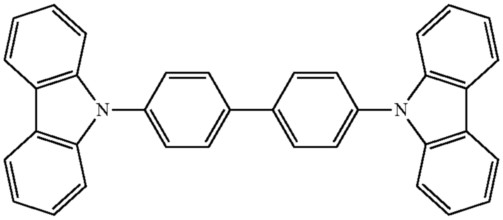 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 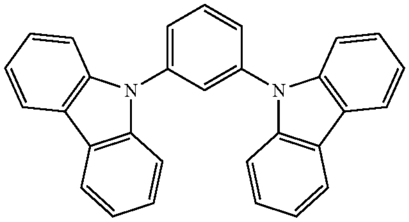 [SMILES: c1cc(-n2c3ccccc3c3ccccc32)cc(-n2c3ccccc3c3ccccc32)c1] | US20030175553 |
| | 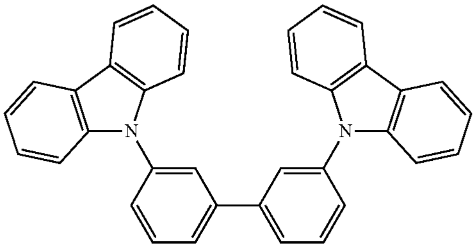 [SMILES: c1cc(-c2cccc(-n3c4ccccc4c4ccccc43)c2)cc(-n2c3ccccc3c3ccccc32)c1] | WO2001039234 |
| Aryltriphenylene compounds | 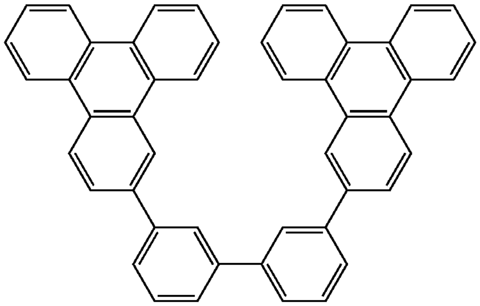 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 3-continued
| MATERIAL | EXAMPLES OF MATERIAL | PUBLICATIONS |
| --- | --- | --- |
| | 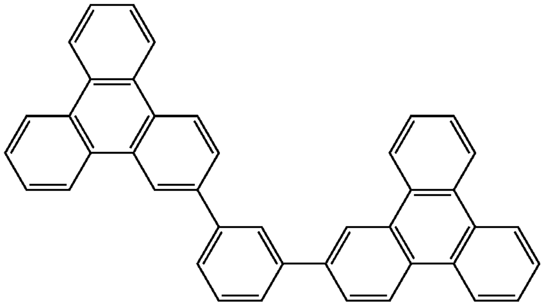 [SMILES: c1cc(-c2ccc3c4ccccc4c4ccccc4c3c2)cc(-c2ccc3c4ccccc4c4ccccc4c3c2)c1] | US20060280965 |
| | 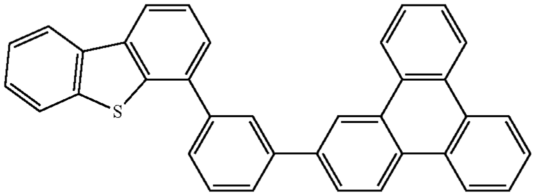 [SMILES: c1cc(-c2ccc3c4ccccc4c4ccccc4c3c2)cc(-c2cccc3c2sc2ccccc23)c1] | WO2009021126 |
| Donor acceptor type molecules | 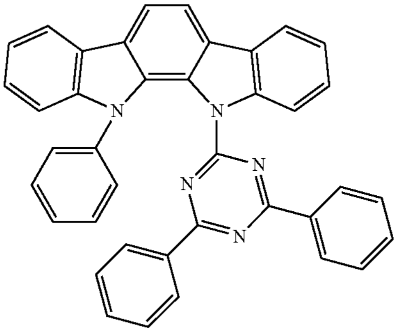 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/ DBF | 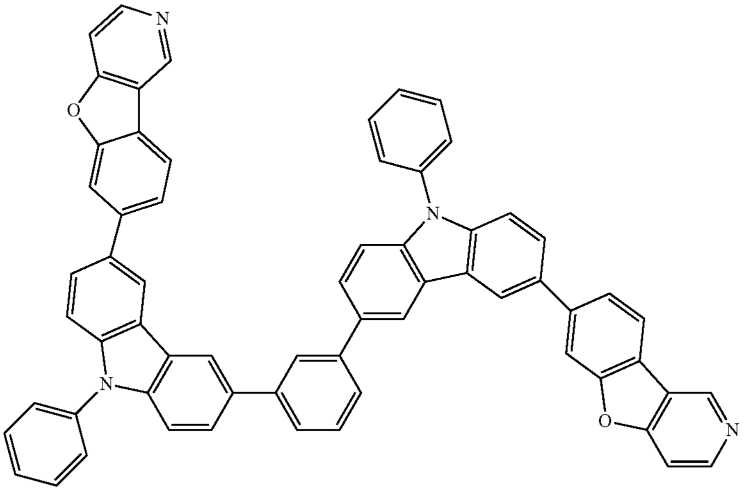 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 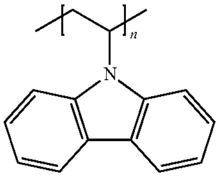 | Appl. Phys. Lett. 77, 2280 (2000) |

TABLE 3-continued
| MATERIAL | EXAMPLES OF MATERIAL | PUBLICATIONS |
|---|---|---|
| Spirofluorene compounds | 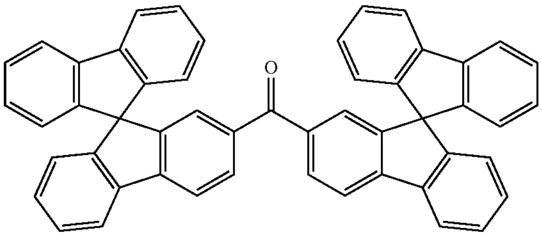 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 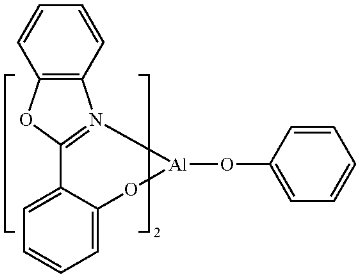 | WO2005089025 |
| | 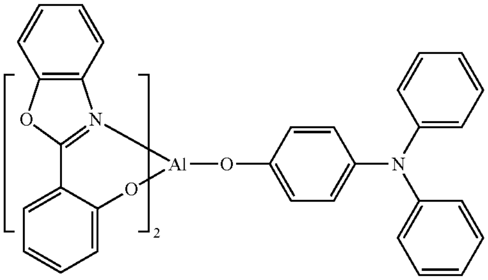 | WO2006132173 |
| | 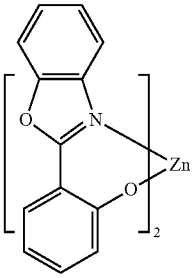 | JP200511610 |
| Spirofluorene-carbazole compounds | 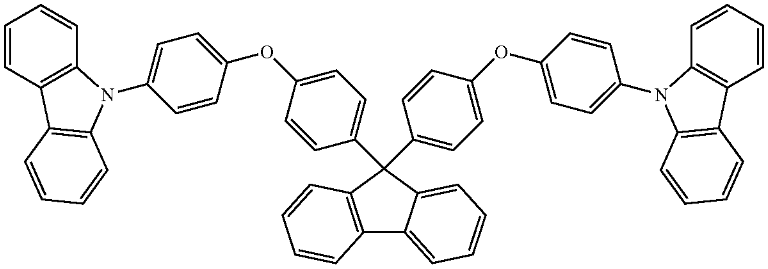 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 3-continued
| MATERIAL | EXAMPLES OF MATERIAL | PUBLICATIONS |
| --- | --- | --- |
| | 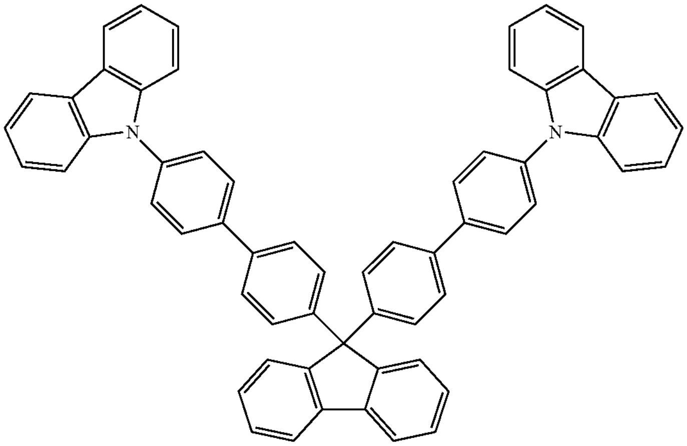 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 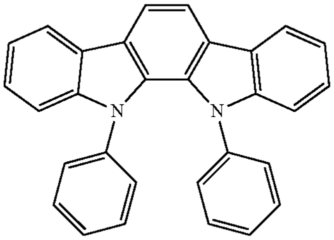 [SMILES: c1ccc(-n2c3ccccc3c3ccc4c5ccccc5n(-c5ccccc5)c4c32)cc1] | WO2007063796 |
| | 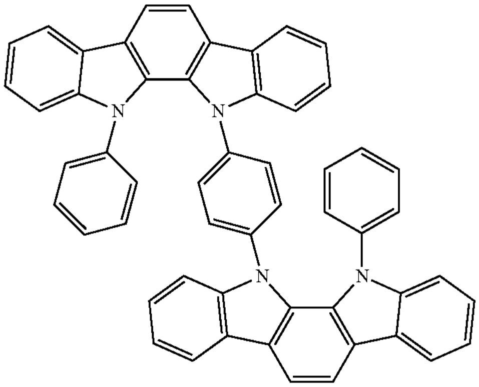 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 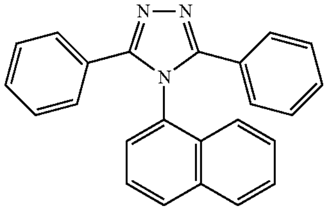 [SMILES: c1ccc(-c2nnc(-c3ccccc3)n2-c2cccc3ccccc23)cc1] | J. Appl. Phys. 90, 5048 (2001) |
| | 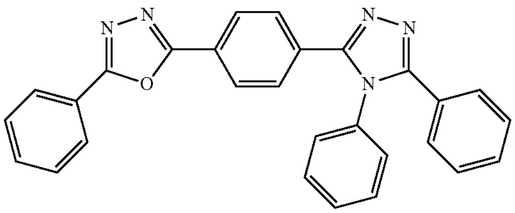 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
|---|---|---|
| Tetraphenylene complexes | 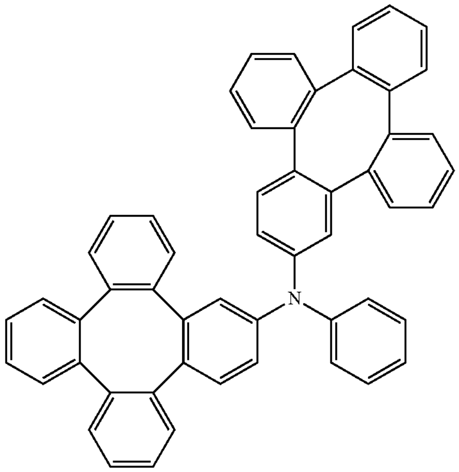 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 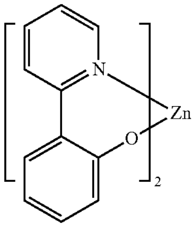 | WO2005030900 |
| Metal coordination complexes (e.g., Zn, Al with N^N ligands) | 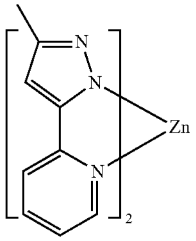 | US20040137268, US20040137267 |
| Blue hosts | | |
| Arylcarbazoles | 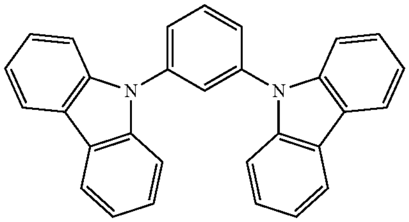 [SMILES: c1cc(-n2c3ccccc3c3ccccc32)cc(-n2c3ccccc3c3ccccc32)c1] | Appl. Phys. Lett, 82, 2422 (2003) |
| | 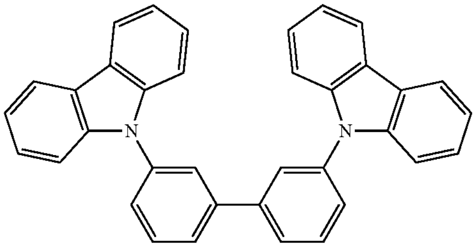 [SMILES: c1cc(-c2cccc(-n3c4ccccc4c4ccccc43)c2)cc(-n2c3ccccc3c3ccccc32)c1] | US20070190359 |

TABLE 3-continued
| MATERIAL | EXAMPLES OF MATERIAL | PUBLICATIONS |
|---|---|---|
| Dibenzothiophene/ Dibenzofuran-carbazole compounds | 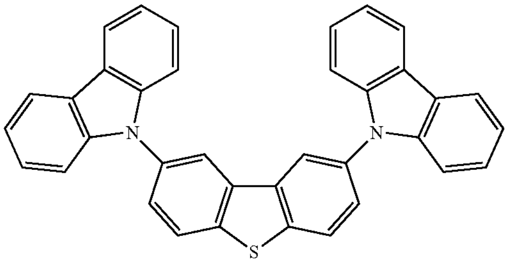 [SMILES: c1ccc2c(c1)c1ccccc1n2-c1ccc2sc3ccc(-n4c5ccccc5c5ccccc54)cc3c2c1] | WO2006114966, US20090167162 |
| | 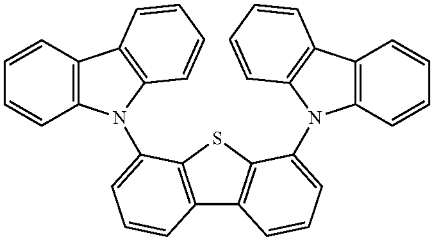 [SMILES: c1cc(-n2c3ccccc3c3ccccc32)c2sc3c(-n4c5ccccc5c5ccccc54)cccc3c2c1] | US20090167162 |
| | 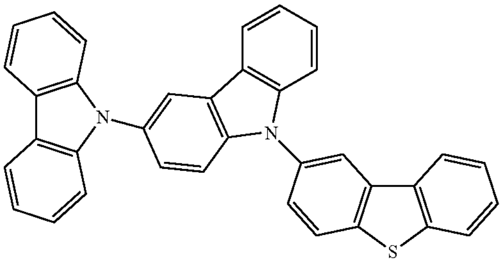 [SMILES: c1ccc2c(c1)sc1ccc(-n3c4ccccc4c4cc(-n5c6ccccc6c6ccccc65)ccc43)cc12] | WO2009086028 |
| | 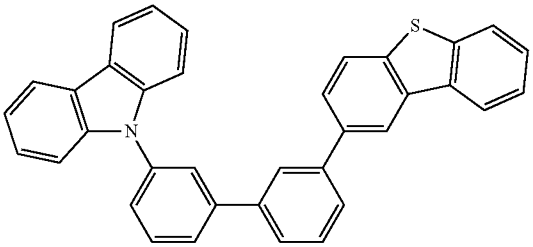 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 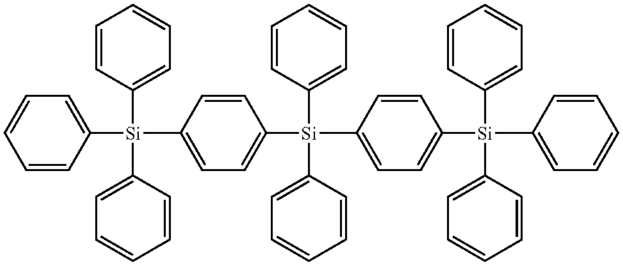 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 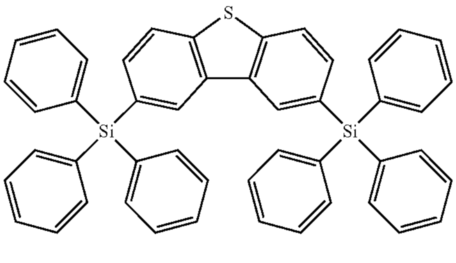 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued
| MATERIAL | EXAMPLES OF MATERIAL | PUBLICATIONS |
|---|---|---|
| Silicon/Germanium aryl compounds | 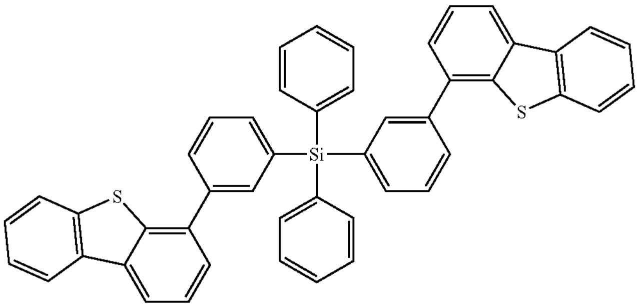 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 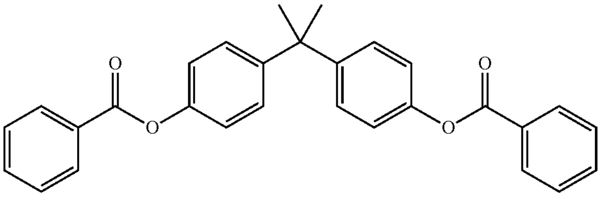 [SMILES: CC(C)(c1ccc(OC(=O)c2ccccc2)cc1)c1ccc(OC(=O)c2ccccc2)cc1] | WO2006100298 |
| High triplet metal organometallic complex | 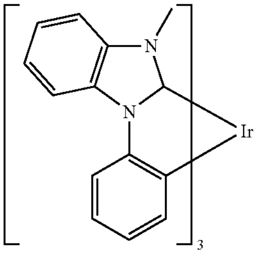 | US7154114 |
| | Phosphorescent dopants<br>Red dopants | |
| Heavy metal porphyrins (e.g., PtOEP) | 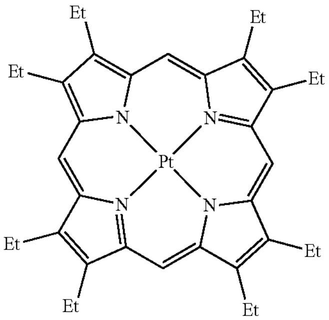 | Nature 395, 151 (1998) |
| Iridium(III) organometallic complexes | 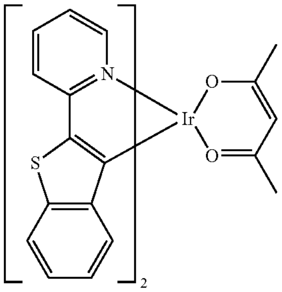 | Appl. Phys. Lett. 78, 1622 (2001) |

TABLE 3-continued
| MATERIAL | EXAMPLES OF MATERIAL | PUBLICATIONS |
|---|---|---|
| | 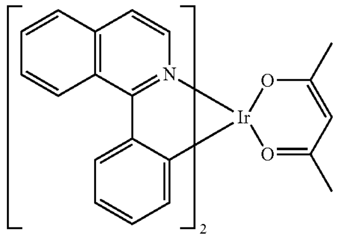 | US2006835469 |
| | 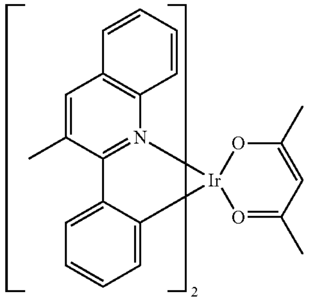 | US2006835469 |
| | 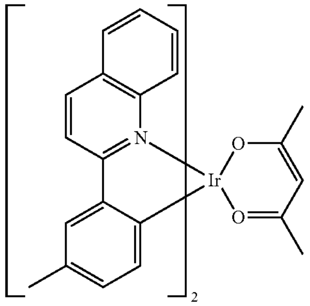 | US20060202194 |
| | 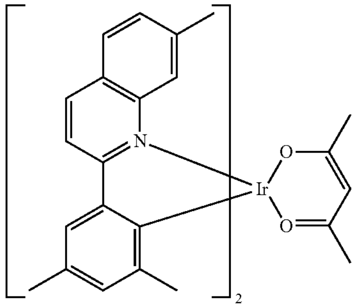 | US20060202194 |
| | 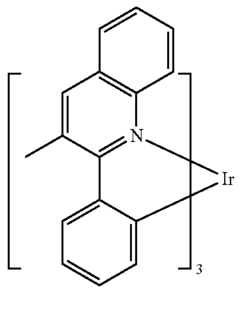 | US20070087321 |

TABLE 3-continued
| MATERIAL | EXAMPLES OF MATERIAL | PUBLICATIONS |
| --- | --- | --- |
| | 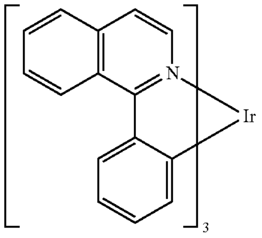 | US20070087321 |
| | 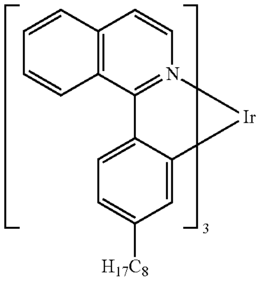 | Adv. Mater. 19, 739 (2007) |
| | 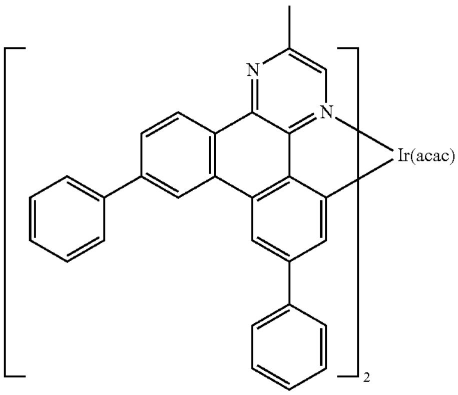 | WO2009100991 |
| | 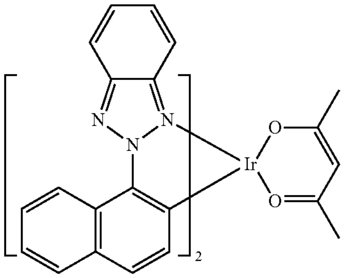 | WO2008101842 |
| Platinum(II) organometallic complexes | 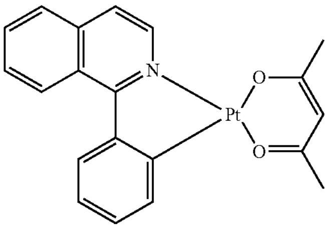 | WO2003040257 |

TABLE 3-continued
| MATERIAL | EXAMPLES OF MATERIAL | PUBLICATIONS |
|---|---|---|
| Osminum(III) complexes | 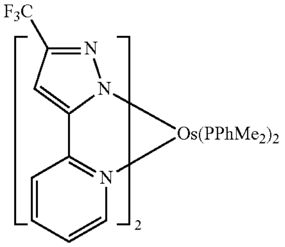 | Chem. Mater. 17, 3532 (2005) |
| Ruthenium(II) complexes | 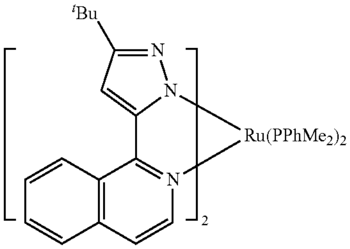 | Adv. Mater. 17, 1059 (2005) |
| Rhenium (I), (II), and (III) complexes | 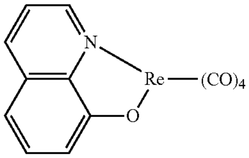 | US20050244673 |
| | Green dopants | |
| Iridium(III) organometallic complexes | 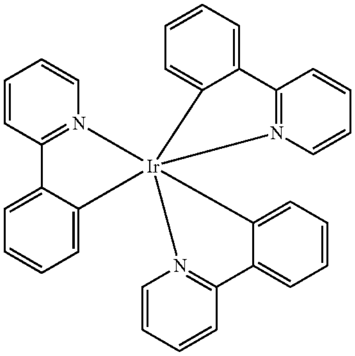 and its derivatives | Inorg. Chem. 40, 1704 (2001) |
| | 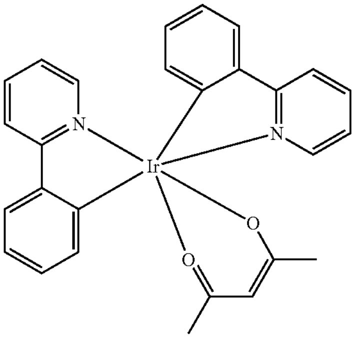 | US20020034656 |

TABLE 3-continued
| MATERIAL | EXAMPLES OF MATERIAL | PUBLICATIONS |
| --- | --- | --- |
| | 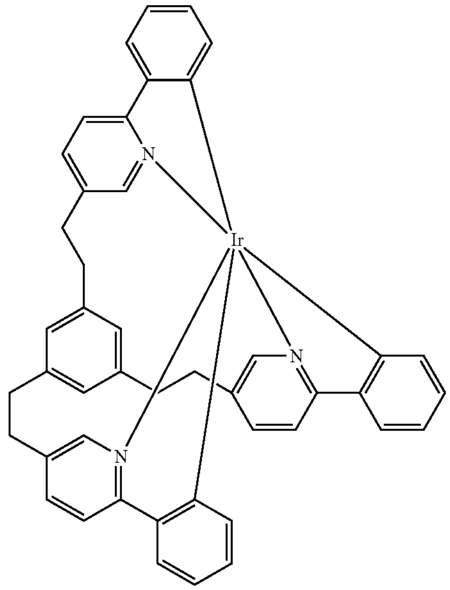 | US7332232 |
| | 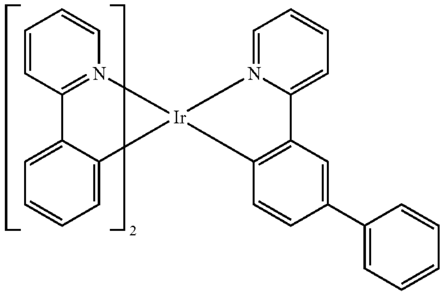 | US20090108737 |
| | 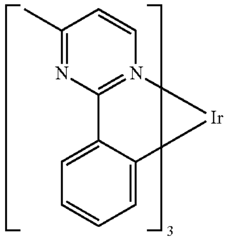 | US20090039776 |
| | 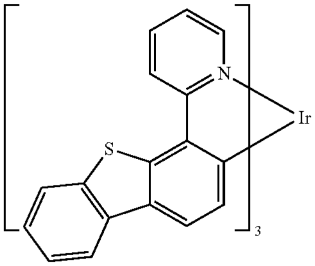 | US6921915 |

TABLE 3-continued
| MATERIAL | EXAMPLES OF MATERIAL | PUBLICATIONS |
|---|---|---|
| | 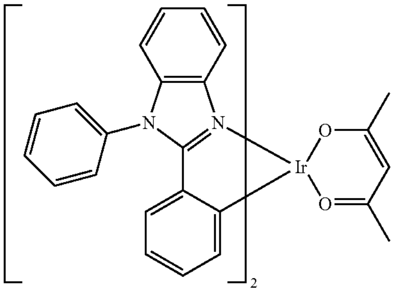 | US6687266 |
| | 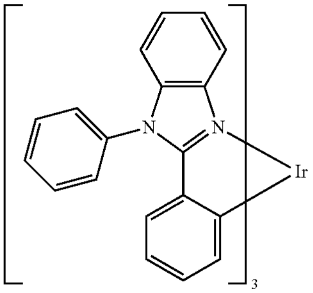 | Chem. Mater. 16, 2480 (2004) |
| | 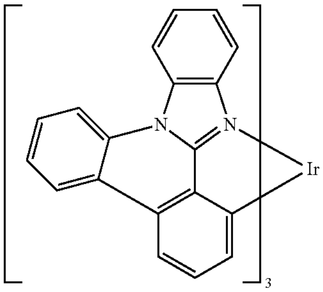 | US20070190359 |
| | 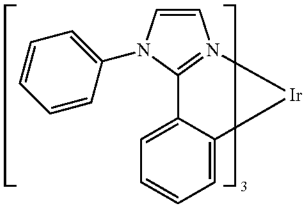 | US 20060008670<br>JP2007123392 |
| | 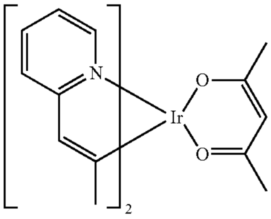 | Adv. Mater. 16, 2003 (2004) |

TABLE 3-continued
| MATERIAL | EXAMPLES OF MATERIAL | PUBLICATIONS |
| --- | --- | --- |
| | 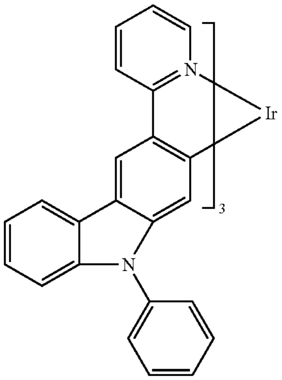 | Angew. Chem. Int. Ed. 2006, 45, 7800 |
| | 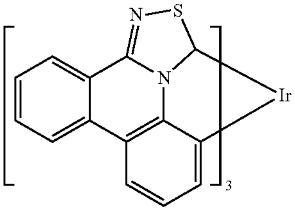 | WO2009050290 |
| | 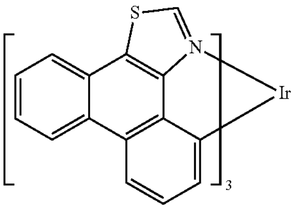 | US20090165846 |
| | 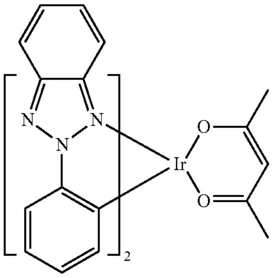 | US20080015355 |
| Monomer for polymeric metal organometallic compounds | 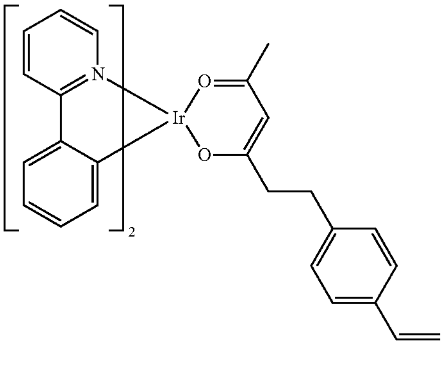 | US7250226, US7396598 |

TABLE 3-continued
| MATERIAL | EXAMPLES OF MATERIAL | PUBLICATIONS |
|---|---|---|
| Pt(II) organometallic complexes, including polydentated ligands | 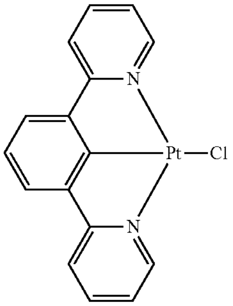 | Appl. Phys. Lett. 86, 153505 (2005) |
| | 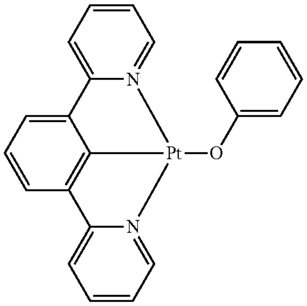 | Appl. Phys. Lett. 86, 153505 (2005) |
| | 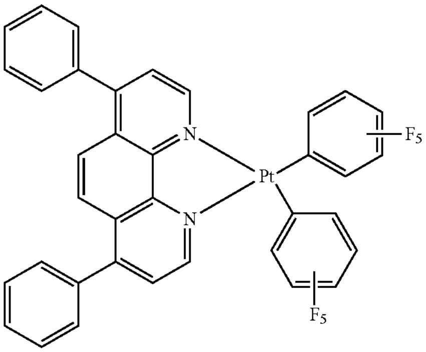 | Chem. Lett. 34, 592 (2005) |
| | 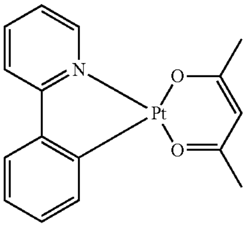 | WO2002015645 |
| | 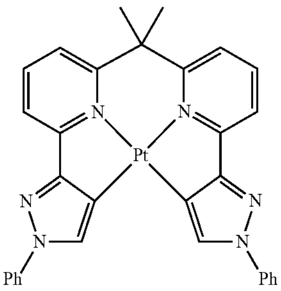 | US20060263635 |

TABLE 3-continued
| MATERIAL | EXAMPLES OF MATERIAL | PUBLICATIONS |
| --- | --- | --- |
| Cu complexes | 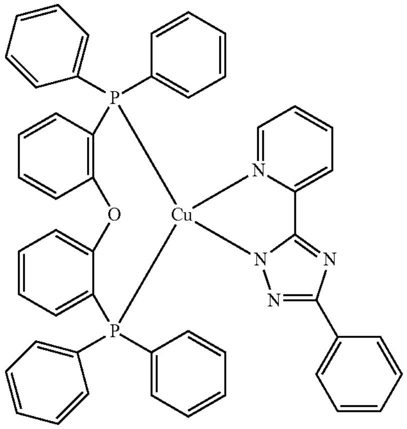 | WO2009000673 |
| Gold complexes | 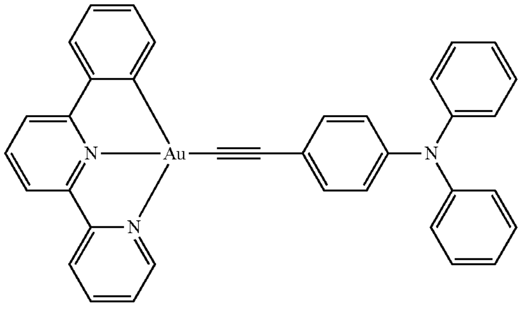 | Chem. Commun. 2906 (2005) |
| Rhenium(III) complexes | 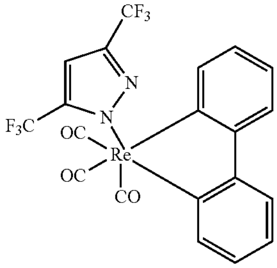 | Inorg. Chem. 42, 1248 (2003) |
| Deuterated organometallic complexes | 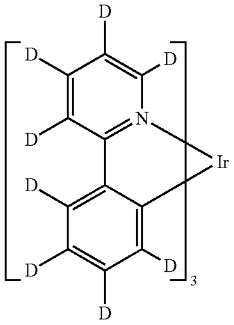 | US20030138657 |

TABLE 3-continued
| MATERIAL | EXAMPLES OF MATERIAL | PUBLICATIONS |
|---|---|---|
| Organometallic complexes with two or more metal centers | 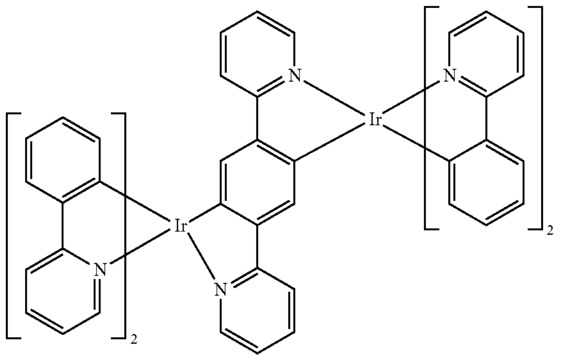 | US20030152802 |
| | 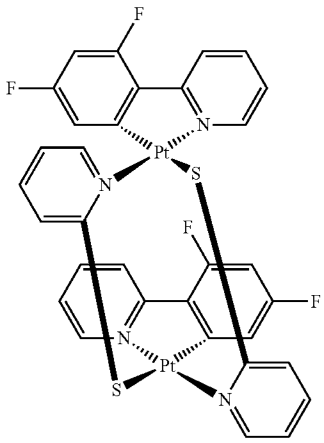 | US7090928 |
| | Blue dopants | |
| Iridium(III) organometallic complexes | 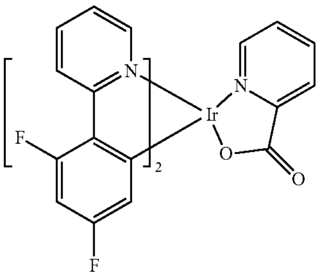 | WO2002002714 |
| | 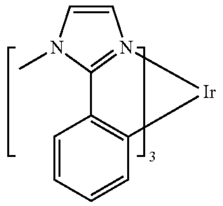 | WO2006009024 |
| | 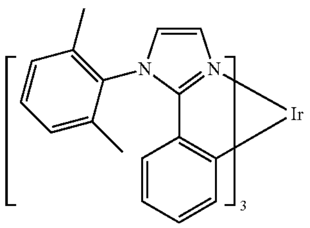 | US20060251923 |

TABLE 3-continued
| MATERIAL | EXAMPLES OF MATERIAL | PUBLICATIONS |
| --- | --- | --- |
| | 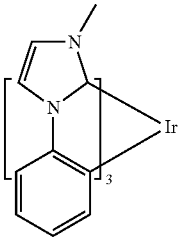 | US7393599, WO2006056418, US20050260441, WO2005019373 |
| | 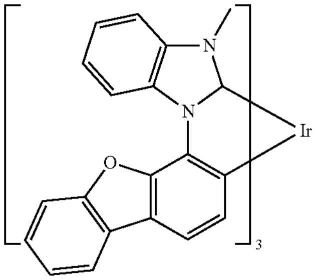 | US7534505 |
| | 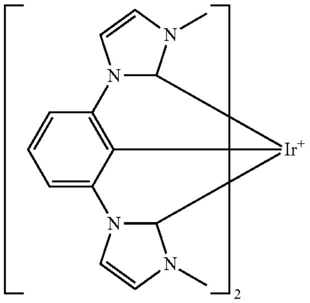 | US7445855 |
| | 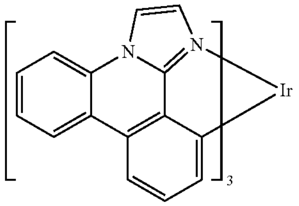 | US20070190359, US20080297033 |
| | 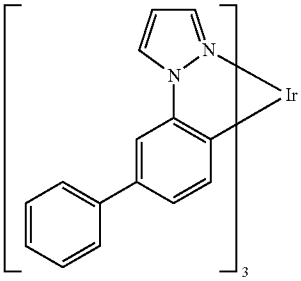 | US7338722 |
| | 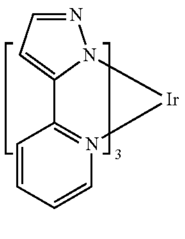 | US20020134984 |

TABLE 3-continued
| MATERIAL | EXAMPLES OF MATERIAL | PUBLICATIONS |
| --- | --- | --- |
| | 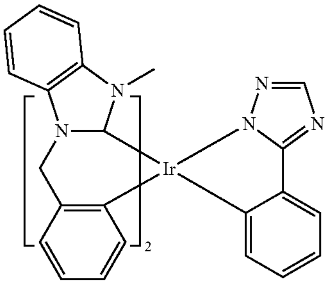 | Angew. Chem. Int. Ed. 47, 1 (2008) |
| | 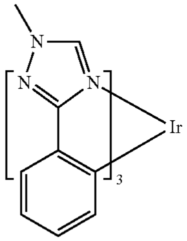 | Chem. Mater. 18, 5119 (2006) |
| | 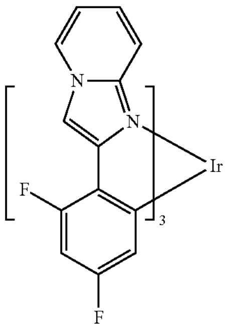 | Inorg. Chem. 46, 4308 (2007) |
| | 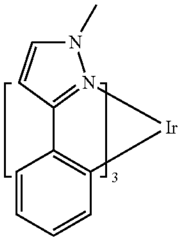 | WO2005123873 |
| | 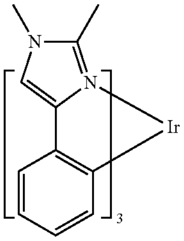 | WO2005123873 |
| | 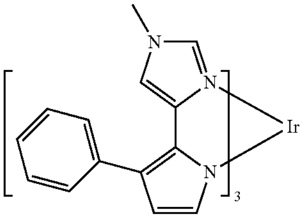 | WO2007004380 |

TABLE 3-continued
| MATERIAL | EXAMPLES OF MATERIAL | PUBLICATIONS |
| --- | --- | --- |
| | 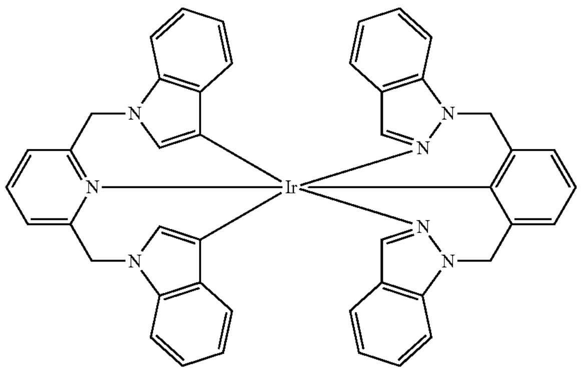 | WO2006082742 |
| Osmium(II) complexes | 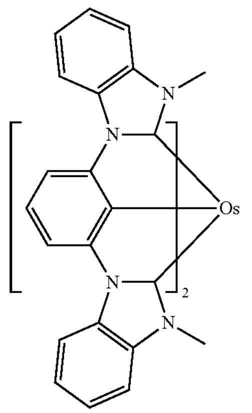 | US7279704 |
| | 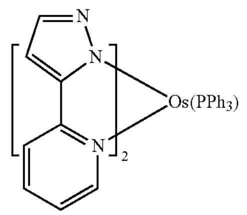 | Organometallics 23, 3745 (2004) |
| Gold complexes | 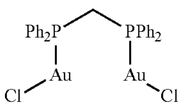 | Appl. Phys. Lett. 74, 1361 (1999) |
| Platinum(II) complexes | 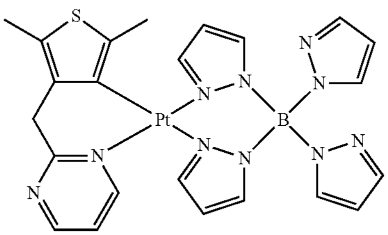 | WO2006098120, WO2006103874 |

TABLE 3-continued
| MATERIAL | EXAMPLES OF MATERIAL | PUBLICATIONS |
|---|---|---|
| | Exciton/hole blocking layer materials | |
| Bathocuprine compounds (e.g., BCP, BPhen) | 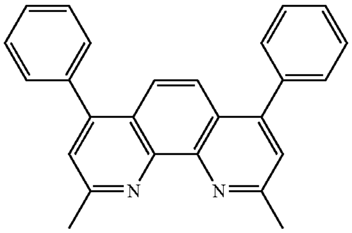 [SMILES: Cc1cc(-c2ccccc2)c2ccc3c(-c4ccccc4)cc(C)nc3c2n1] | Appl. Phys. Lett. 75, 4 (1999) |
| | 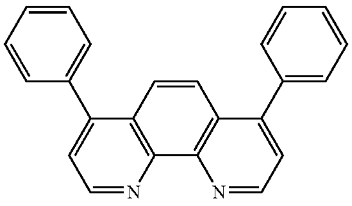 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 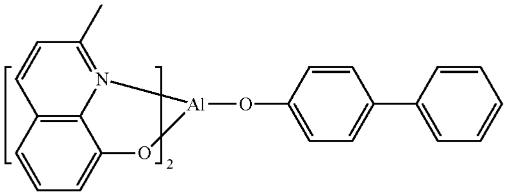 | Appl. Phys. Lett. 81, 162 (2002) |
| 5-member ring electron deficient heterocycles such as triazole, oxadiazole, imidazole, benzoimidazole | 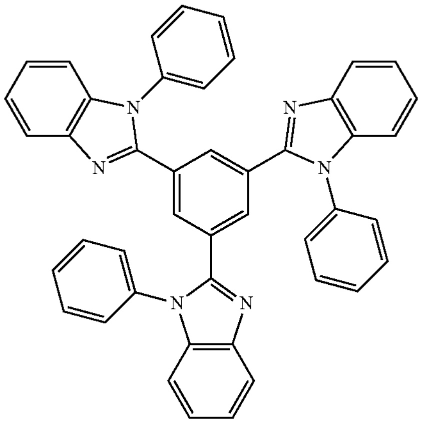 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 3-continued
| MATERIAL | EXAMPLES OF MATERIAL | PUBLICATIONS |
| --- | --- | --- |
| Triphenylene compounds | 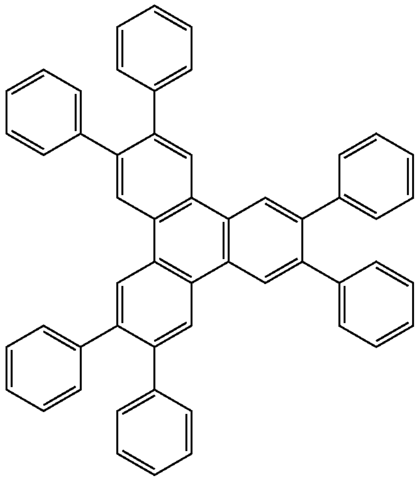 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 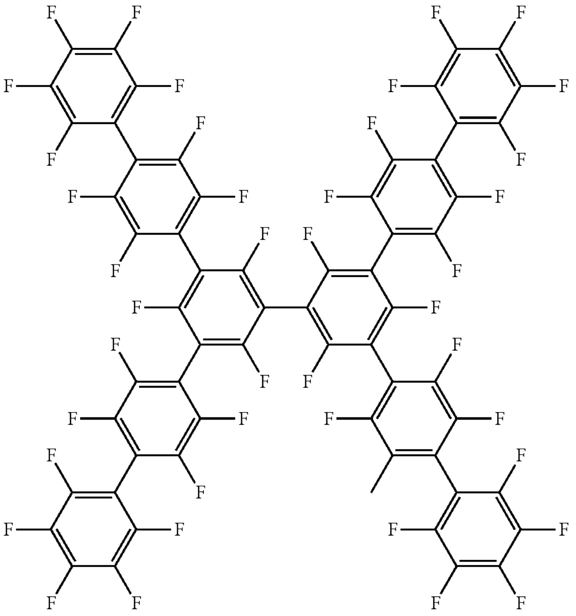 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 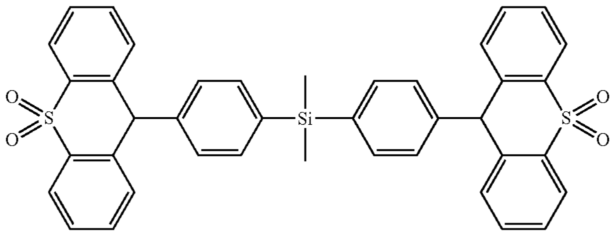 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 3-continued
| MATERIAL | EXAMPLES OF MATERIAL | PUBLICATIONS |
|---|---|---|
| | Electron transporting materials | |
| Anthracene-benzoimidazole compounds | 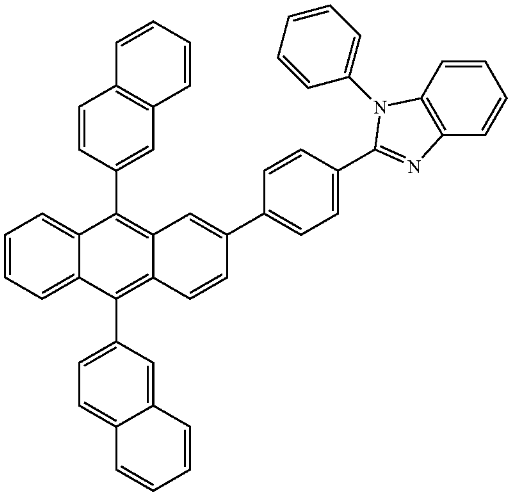 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 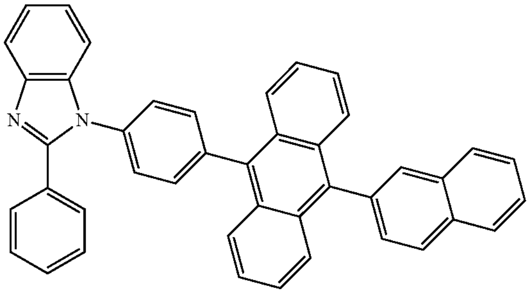 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 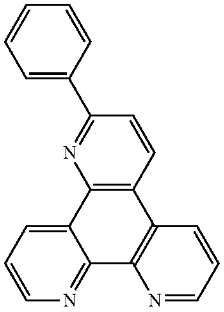 [SMILES: c1ccc(-c2ccc3c4cccnc4c4ncccc4c3n2)cc1] | US20090115316 |
| Anthracene-benzothiazole compounds | 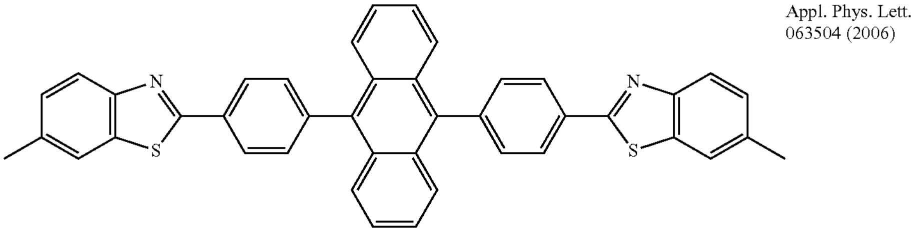 | Appl. Phys. Lett. 89, 063504 (2006) |
| Metal 8-hydroxyquinolates (e.g., $Alq_3$, $Zrq_4$) | 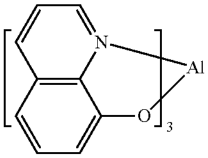 | Appl. Phys. Lett. 51, 913 (1987) US7230107 |

TABLE 3-continued
| MATERIAL | EXAMPLES OF MATERIAL | PUBLICATIONS |
|---|---|---|
| Metal hydroxybenoquinolates | 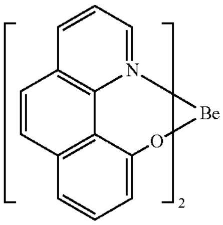 | Chem. Lett. 5, 905 (1993) |
| Bathocuprine compounds such as BCP, BPhen, etc | 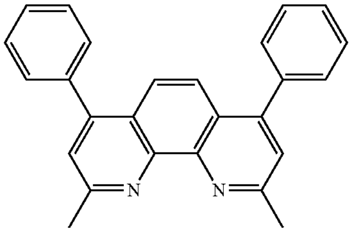 [SMILES: Cc1cc(-c2ccccc2)c2ccc3c(-c4ccccc4)cc(C)nc3c2n1] | Appl. Phys. Lett. 91, 263503 (2007) |
| | 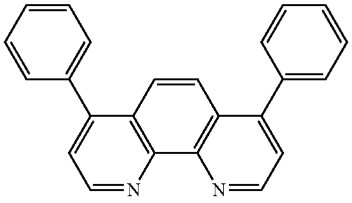 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 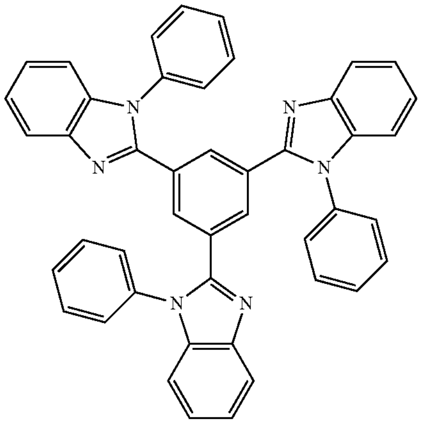 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 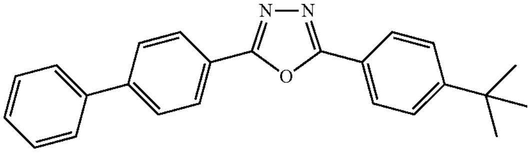 [SMILES: CC(C)(C)c1ccc(-c2nnc(-c3ccc(-c4ccccc4)cc3)o2)cc1] | Appl. Phys. Lett. 55, 1489 (1989) |
| | 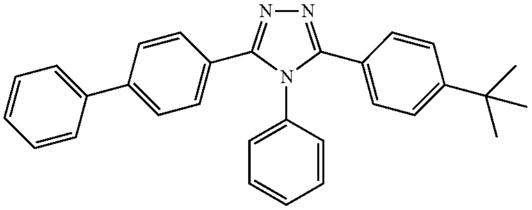 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |

TABLE 3-continued
| MATERIAL | EXAMPLES OF MATERIAL | PUBLICATIONS |
| --- | --- | --- |
| Silole compounds | 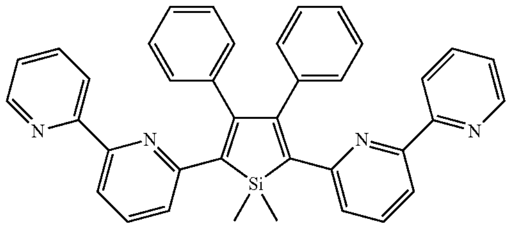 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 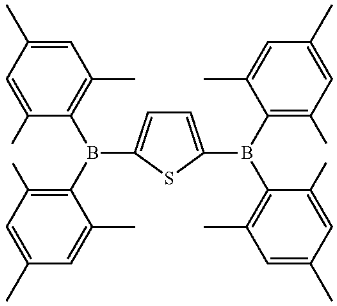 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 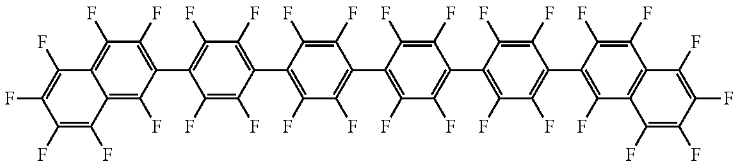 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 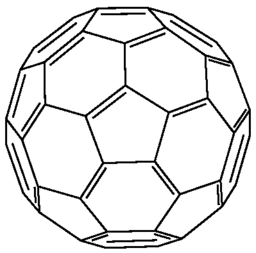 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 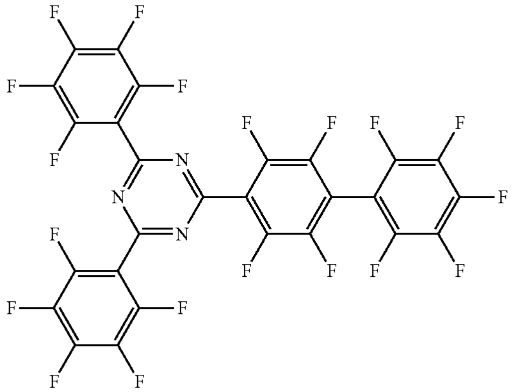 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 3-continued

| MATERIAL | EXAMPLES OF MATERIAL | PUBLICATIONS |
|---|---|---|
| Zn (N^N) complexes | 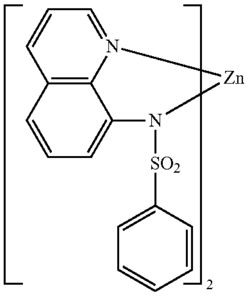 | US6528187 |

EXPERIMENTAL

Compound Examples

Several of the compounds were synthesized as follows:

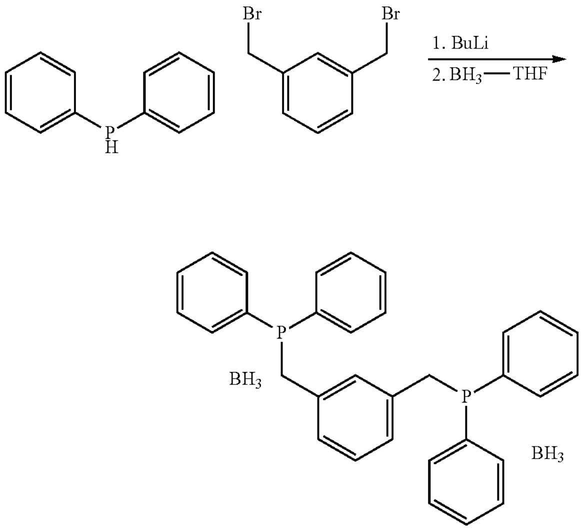

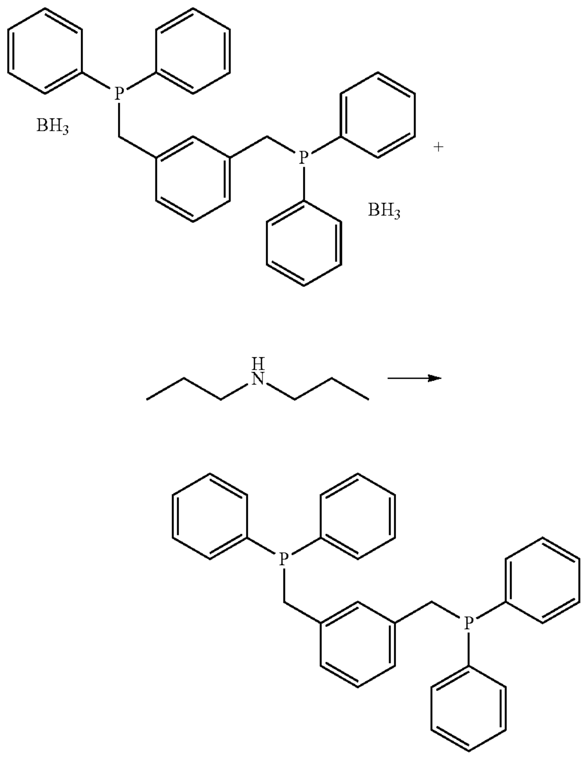

A solution of diphenylphosphine (5.80 mL, 33.3 mmol) in 200 mL THF was cooled to −78° C. BuLi (14.67 mL, 36.7 mmol, 2.5 M in hexane) was added dropwise to give an orange-red solution, which was warmed to room temperature for 30 minutes before re-cooling to −78° C. 1,3-bis(bromomethyl)benzene (3.78 g, 14.33 mmol) in 30 mL of THF was then added drop-wise and the solution allowed to slowly warm to room temperature overnight. After heating to reflux for 2 h, the mixture was cooled to room temperature and BH3•THF (100 mL, 100 mmol, 1 M in THF) was added dropwise via canula. The reaction was stirred overnight at which point TLC (1/1 dichloromethane/hexane) showed no starting material. The reaction was poured over 300 mL of ice and extracted with dichloromethane. After removal of the solvent, the crude material was chromatographed on silica gel with (1/1 dichloromethane/hexane) to give the desired product, as confirmed by NMR.

The starting material (2.5 g, 4.98 mmol) was dissolved in dipropylamine (50 mL, 365 mmol) and heated to reflux for 16 h, at which time NMR indicated the absence of starting material. After removal of the solvent, the crude product was chromatographed on a triethylamime-pretreated silica gel column eluting with 1/1 hex/dichloromethane. The product (1.8 g) was obtained as a colorless oil, as confirmed by NMR.

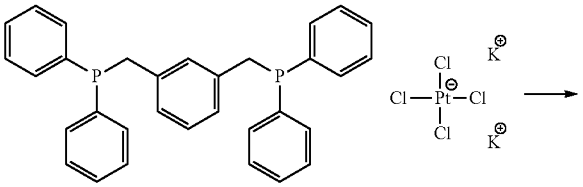

-continued

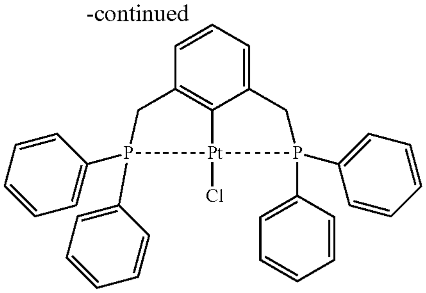

Dissolved potassium tetrachloroplatinate(II) (1.575 g, 3.79 mmol) in 50 mL water and added 1,3-bis((diphenylphosphino)methyl)benzene (1.8 g, 3.79 mmol) in 50 mL acetonitrile. The reaction was heated to reflux for 18 h. Water was added and the reaction was extracted with dichloromethane. The volume of solvent was reduced and the product was precipitated with MeOH, washed with MeOH and ether and dried. The crude solid was sublimed (200° C., $10^{-5}$ mbar) to give 1.7 g of the product as a pale yellow solid. The product was confirmed by NMR.

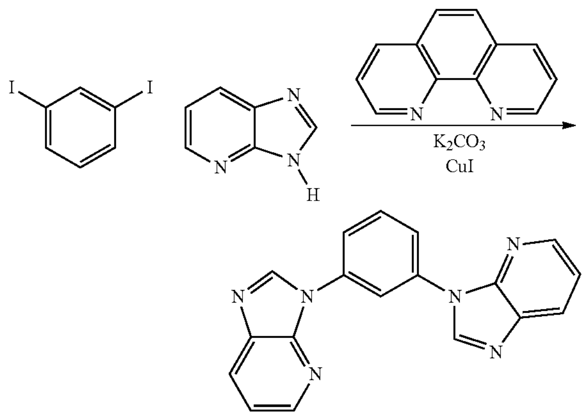

To a 250 mL 3-neck flask 1,10-phenanthroline (0.66 g, 3.66 mmol), potassium carbonate (5.55 g, 40.2 mmol), 1,3-diiodobenzene (6.02 g, 18.25 mmol), 3H-imidazo[4,5-b]pyridine (4.75 g, 39.9 mmol), and copper(I) iodide (0.75 g, 3.94 mmol) were added, followed by 50 mL of DMF. The mixture was degassed for 15 minutes and then heated at 120° C. for 24 h. After cooling to room temperature, 100 mL of water was added and extracted with 4×100 mL $CH_2Cl_2$. The extracts were washed with 100 mL water, dried and evaporated. The crude product was chromatographed on a silica column, eluting with $CH_2Cl_2$ and then 98:2 $CH_2Cl_2$:MeOH. The first fractions contained a mixture of the desired product and mono-addition product which were separated by vacuum distillation (220° C., 60 mbar) to give 1.2 g of the desired product as a white solid. The product was confirmed by NMR and GC/MS.

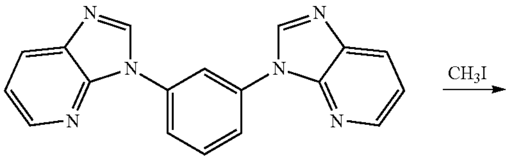

-continued

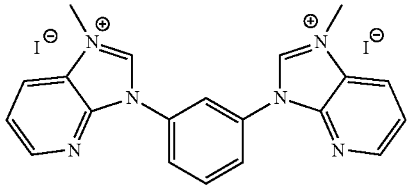

1,3-Bis(3H-imidazo[4,5-b]pyridin-3-yl)benzene (2.78 g, 8.90 mmol) was suspended in 10 mL of DMF in a glass pressure bottle. Iodomethane (5.54 mL, 89 mmol) was then added and the mixture warmed in an oil bath to 90° C. for 20 h. After cooling, ether was added to precipitate the product, which was filtered and washed with ether to yield 5.0 g of the desired product as confirmed by NMR.

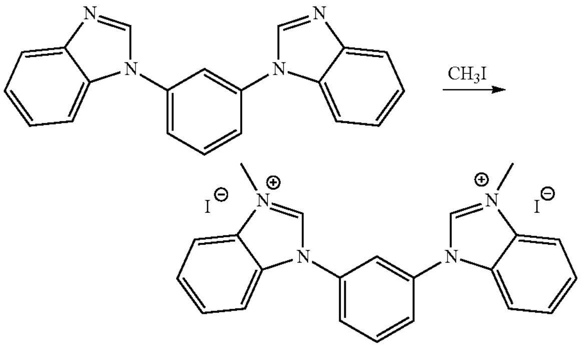

1,3-Bis(1-H-benzo[d]imidazol-1-yl)benzene was synthesized according to the method of Zhang et. al. (*Chem. Commun.* 2008, 46, 6170). A 350 mL glass pressure bottle was charged with 1,3-bis(1-H-benzo[d]imidazol-1-yl)benzene (7.0 grams, 22.6 mmol), dimethylformamide (200 mL) and iodomethane (21.0 mL, 337 mmol). The flask was sealed and placed in an oil bath and heated to 80° C. for 22 h. After cooling to ambient temperature, the product was filtered and washed with ether to give a tan solid. The desired product as confirmed by NMR.

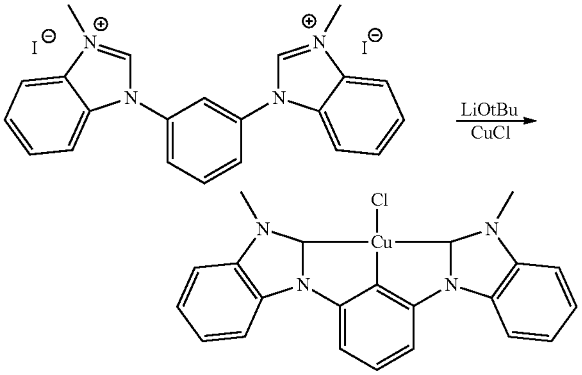

Copper (I) chloride (0.50 g, 5.05 mmol), lithium tert-butoxide (0.40 g, 5.05 mmol) and 35 mL of THF were placed in a 50 mL round bottom flask and stirred for 18 h. The bis (benzimidazole) iodide salt (0.50 grams, 0.84 mmol) was then added and the reaction mixture stirred for 20 h. The crude product was then filtered and washed with additional THF.

The product was then stirred in 200 mL of dichloromethane for 3 h, filtered and the filtrate was evaporated to give a tan powder. The desired product as confirmed by NMR.

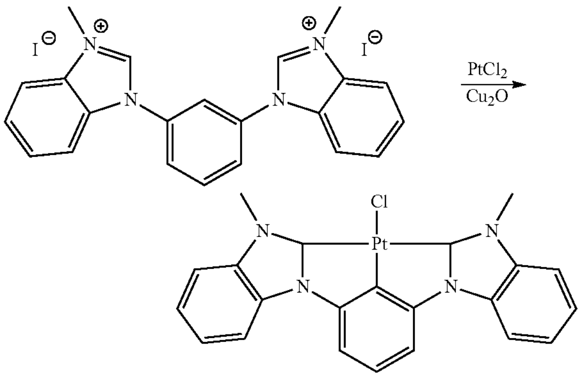

A 100 mL round-bottom flask was charged with of bis (benzimidazole) iodide salt (0.50 g, 0.84 mmol), copper (I) oxide (0.60 g, 4.20 mmol) and 50 ml of DMSO and stirred at 150° C. for 18 h. Platinum(II) chloride (0.21 grams, 0.80 mmol) was then added and the reaction stirred for an additional 5 h before being diluted with water (100 mL). The product was extracted with dichloromethane and chromatographed on a silica gel column, eluting with dichloromethane to give the product as a yellow solid. The desired product as confirmed by NMR.

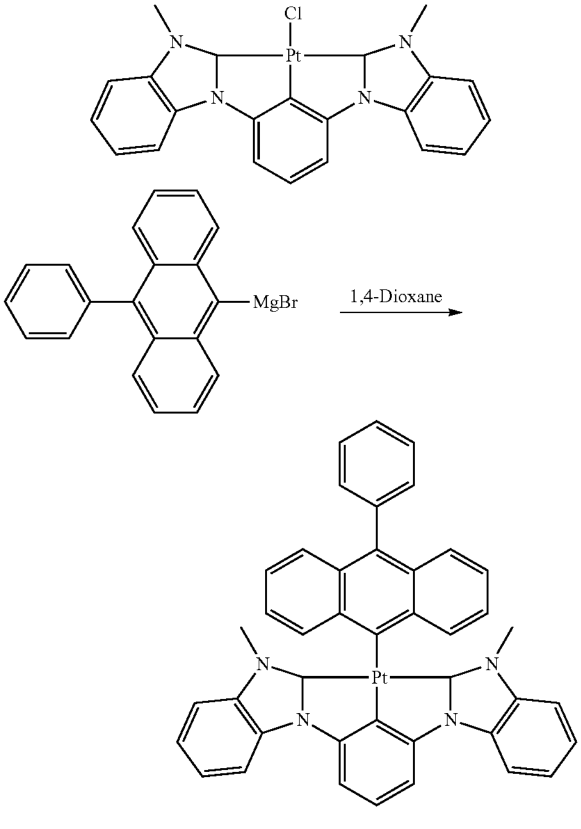

To magnesium in 5 mL of 1,4-dioxane is added dropwise 9-bromo-10-phenylanthracene in 10 mL of 1,4-dioxane. After complete addition, reflux for 30 minutes and cool to room temperature. Add platinum chloride complex in 20 mL of 1,4-dioxane and heat the reaction mixture to reflux overnight. Cool to room temperature, quench with water and extract 3 times with dichloromethane. Remove the solvent and chromatograph the crude product on silica gel.

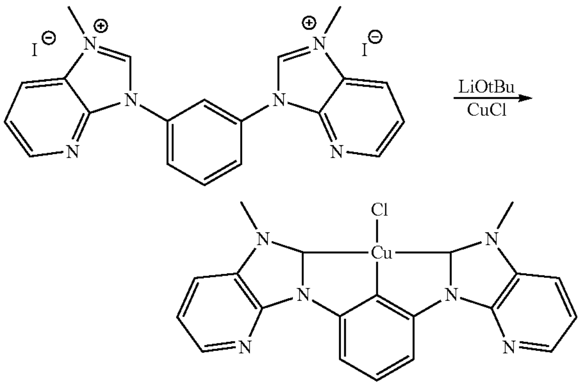

Place copper (I) chloride, lithium tert-butoxide and THF in a round-bottom flask and stir for 18 h. Add the bis(azabenzimidazole) iodide salt and stir for 20 h. Filter the crude product and wash with additional THF. Stir the crude product in 200 mL of dichloromethane for 3 h, filter and evaporate the solvent from the filtrate to give a tan powder.

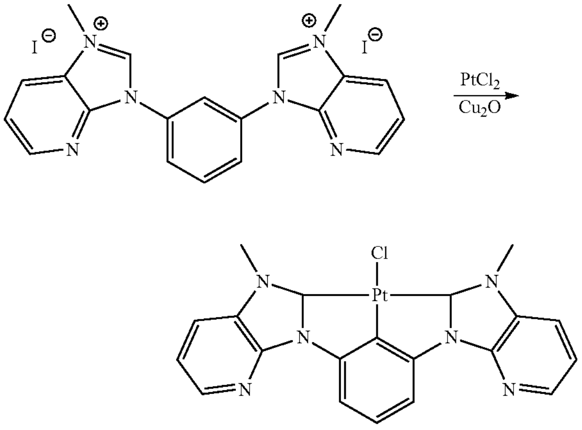

Charge a 100 mL round-bottom flask with the bis(azabenzimidazole) iodide salt, copper (I) oxide and DMSO and stir at 150° C. for 18 h. Add platinum(II) chloride and stir the reaction for an additional 5 h. Dilute with water and extract with dichloromethane. After removal of the solvent, chromatograph the crude product on a silica gel column.

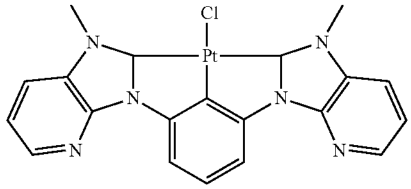

-continued

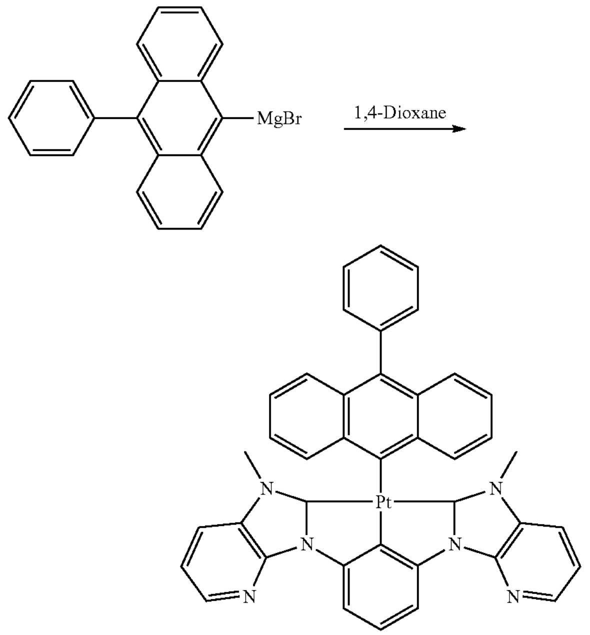

Add dropwise 9-bromo-10-phenylanthracene in 10 mL of 1,4-dioxane to magnesium in 5 mL of 1,4-dioxane. After complete addition, reflux for 30 minutes and cool to room temperature. Add platinum chloride complex in 20 mL of 1,4-dioxane and heat the reaction mixture to reflux overnight. Cool to room temperature, quench with water and extract 3 times with dichloromethane. Remove the solvent and chromatograph the crude product on silica gel.

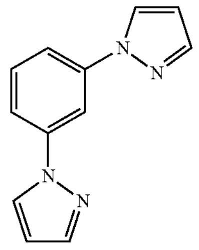 [SMILES: c1cc(-n2cccn2)cc(-n2cccn2)c1]

The intermediate above was synthesized according to the methodology of Develay et al. *Inorganic Chemistry* 47 (23) pp 11129-11142 (2008).

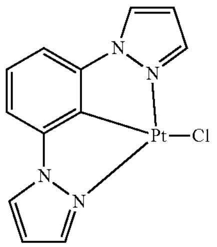

The complex was prepared according to the procedure of Willison et al., *Inorg. Chem.* 47 (4) pp 1258-1260 (2008).

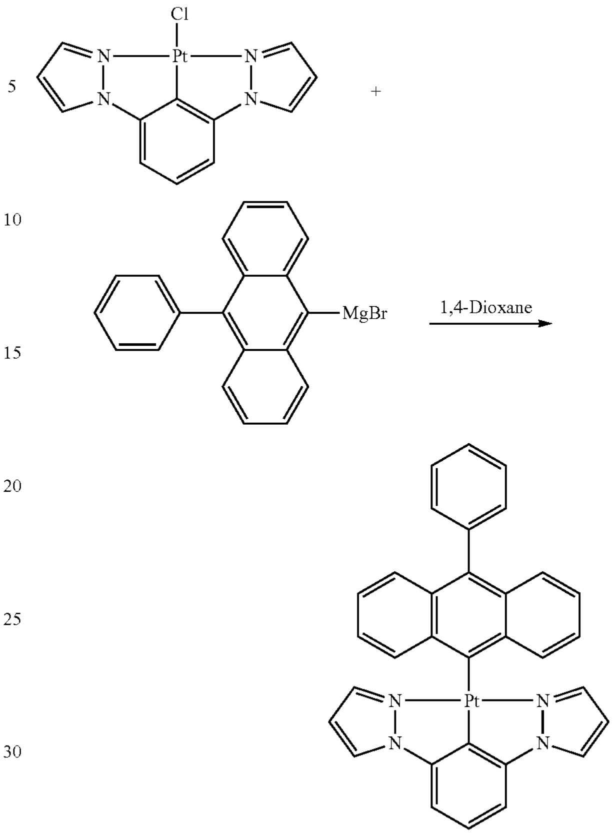

Add dropwise 9-bromo-10-phenylanthracene in 10 mL of 1,4-dioxane to magnesium in 5 mL of 1,4-dioxane. After complete addition, reflux for 30 minutes and cool to room temperature. Add platinum chloride complex in 20 mL of 1,4-dioxane and heat the reaction mixture to reflux overnight. Cool to room temperature, quench with water and extract 3 times with dichloromethane. Remove the solvent and chromatograph the crude product on silica gel.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound according to Formula II:

Formula II

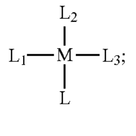

wherein the ligand L has a structure according to Formula I:

Formula I

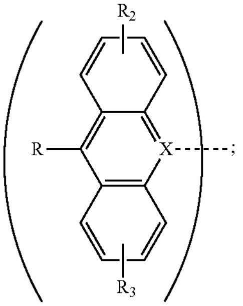

wherein X is C or N;

wherein the ligand L is coordinated to a metal M through coordinating atom X;

wherein M is a transition metal;

wherein $L_1$, $L_2$, and $L_3$ are different from L and independently C, N, O, Si, P, S, or Se coordinating ligands to the metal M;

wherein the compound is selected from the group consisting of:

Formula III (a)

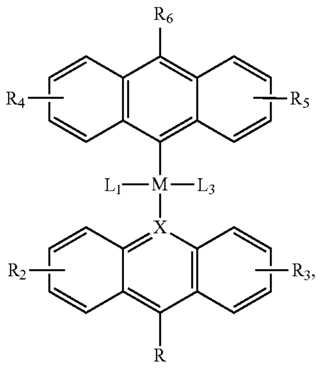

(b) Formula III, wherein any three of L, $L_1$, $L_2$, and $L_3$ are linked together to form a tridentate ligand; and (c) Formula III, wherein any two of L, $L_1$, $L_2$, and $L_3$ are linked together to form a bidentate ligand;

wherein R and $R_6$ are independently selected from alkyl, alkenyl, alkynyl, amino, alkoxy, silyl, phosphino, mercaptyl, aryl or heteroaryl;

wherein $R_2$, $R_3$, $R_4$, and $R_5$ may represent mono, di, tri, or tetra substitutions; and wherein $R_2$, $R_3$, $R_4$, and $R_5$ are independently selected from the group consisting of hydrogen, alkyl, alkoxy, amino, alkenyl, alkynyl, aryl and heteroaryl.

2. The compound of claim 1, wherein the metal M is a third row transition metal.

3. The compound of claim 1, wherein the metal M is Pt.

4. The compound of claim 1, wherein the compound is neutral.

5. The compound of claim 1, wherein the compound is charged.

6. The compound of claim 1, wherein R is aryl or heteroaryl.

7. The compound of claim 1, wherein R is selected from the group consisting of:

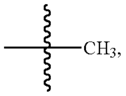, 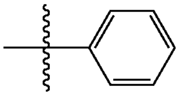, 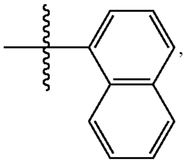,

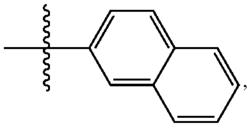, 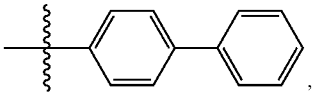,

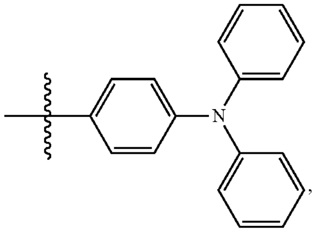,

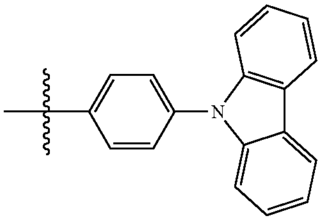

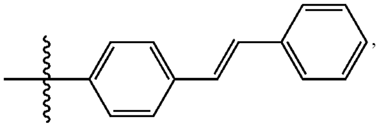,

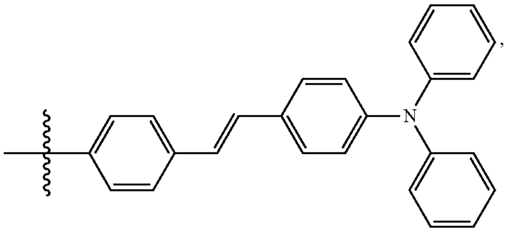,

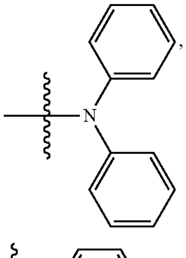, 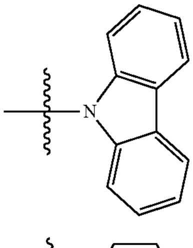

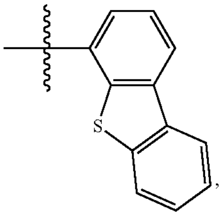, 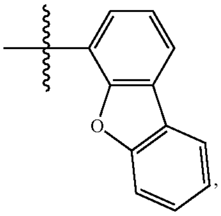,

-continued

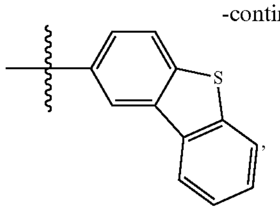,

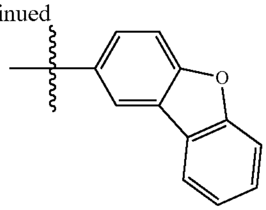

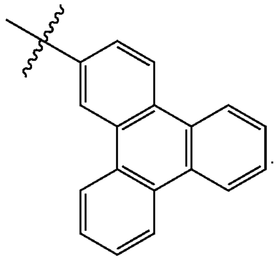.

8. The compound of claim 1, wherein the tridentate ligand forms at least one 5-member cyclometallating ring with M.

9. The compound of claim 1, wherein $R_2$ and $R_3$ are fused cyclic or heterocyclic rings.

10. The compound of claim 1, wherein one of $L_1$, $L_2$, and $L_3$ is anthracenyl.

11. A first device comprising an organic light emitting device, comprising:

an anode;

a cathode; and an organic layer, disposed between the anode and the cathode, further comprising a compound according to Formula II:

Formula II

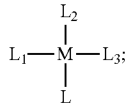

wherein the ligand L has a structure according to Formula I:

Formula I

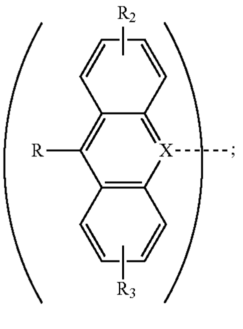

wherein X is C or N;

wherein the ligand L is coordinated to a metal M through coordinating atom X;

wherein M is a transition metal;

wherein $L_1$, $L_2$, and $L_3$ are different from L and independently C, N, O, Si, P, S, or Se coordinating ligands to the metal M;

wherein the compound is selected from the group consisting of:

(a)

Formula III

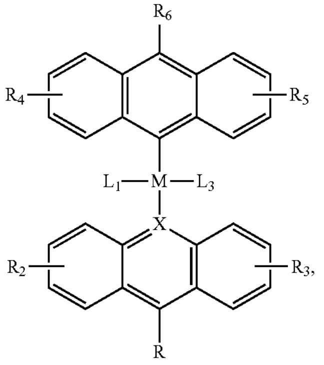

(b) Formula III, wherein any three of L, $L_1$, $L_2$, and $L_3$ are linked together to form a tridentate ligand; and (c) Formula III, wherein any two of L, $L_1$, $L_2$, and $L_3$ are linked together to form a bidentate ligand, wherein R and $R_6$ are independently selected from alkyl, alkenyl, alkynyl, amino, alkoxy, silyl, phosphino, mercaptyl, aryl or heteroaryl;

wherein $R_2$, $R_3$, $R_4$, and $R_5$ may represent mono, di, tri, or tetra substitutions; and wherein $R_2$, $R_3$, $R_4$, and $R_5$ are independently selected from the group consisting of hydrogen, alkyl, alkoxy, amino, alkenyl, alkynyl, aryl and heteroaryl.

12. The first device of claim 11, wherein the metal M is a $3^{rd}$ row transition metal.

13. The first device of claim 11, wherein the metal M is Pt.

14. The first device of claim 11, wherein the compound is neutral.

15. The first device of claim 11, wherein the compound is charged.

16. The first device of claim 11, wherein R is aryl or heteroaryl.

17. The first device of claim 11, wherein R is selected from the group consisting of:

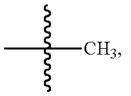

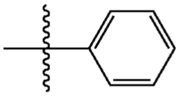,

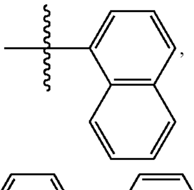,

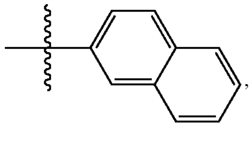,

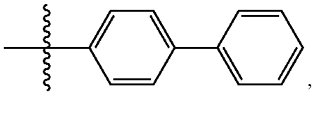,

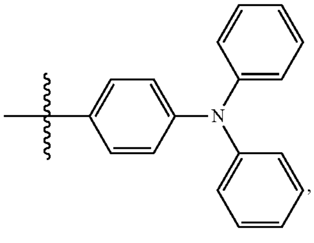,

-continued

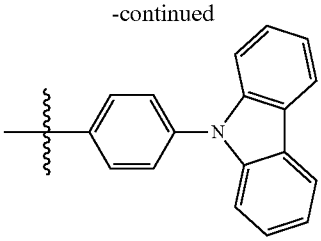

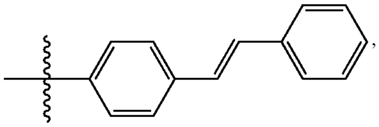,

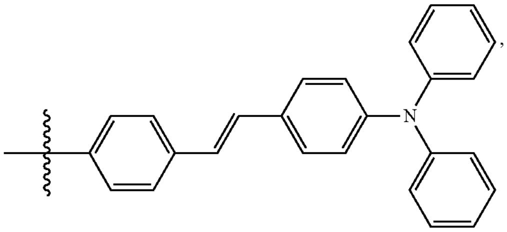,

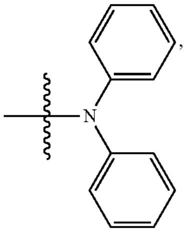,

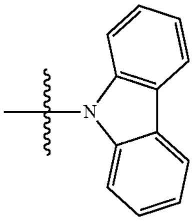

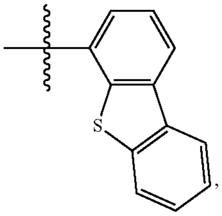,

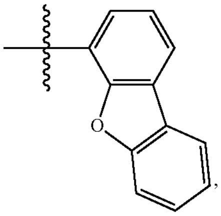,

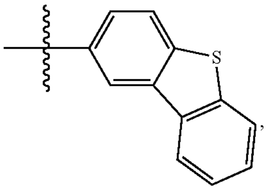,

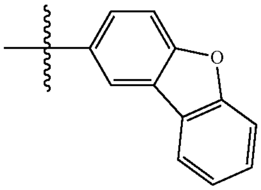

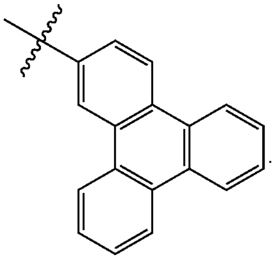.

18. The first device of claim 11, wherein the tridentate ligand forms at least one 5-member cyclometallating ring with M.

19. The first device of claim 11, wherein the organic layer is an emissive layer and the compound is an emissive dopant.

20. The first device of claim 11, wherein the device is a consumer product.

21. The first device of claim 11, wherein the device is an organic light emitting device.

22. The first device of claim 11, wherein $R_2$ and $R_3$ are fused cyclic or heterocyclic rings.

23. The first device of claim 11, wherein one of $L_1$, $L_2$, and $L_3$ is anthracenyl.

24. A compound selected from the group consisting of:

Compound 1G

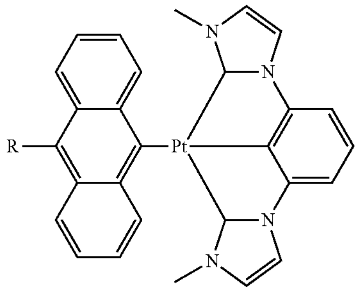

Compound 2G

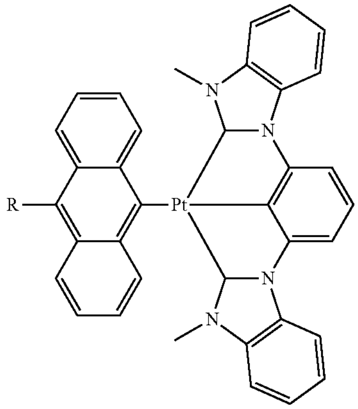

Compound 3G

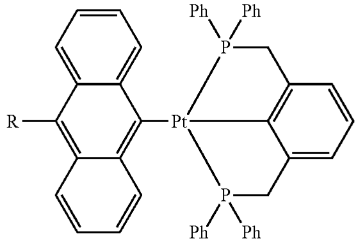

Compound 4G

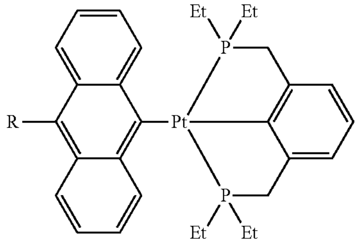

Compound 5G

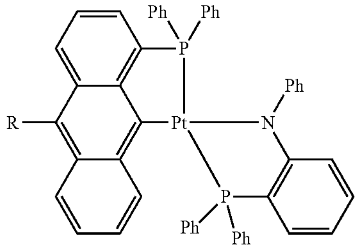

-continued
Compound 6G
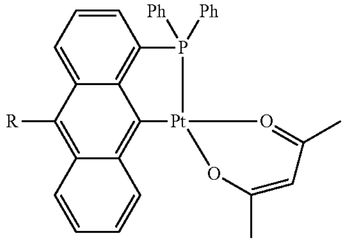
Compound 7G
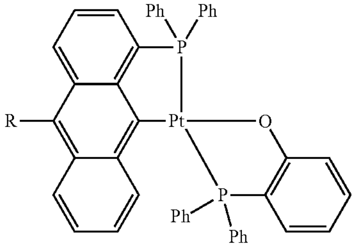
Compound 8G
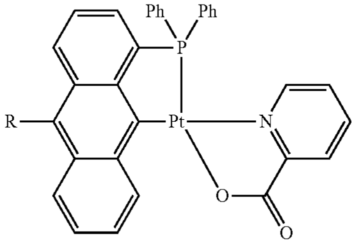
Compound 9G
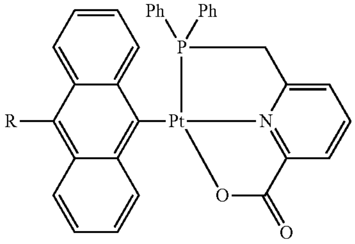
Compound 10G
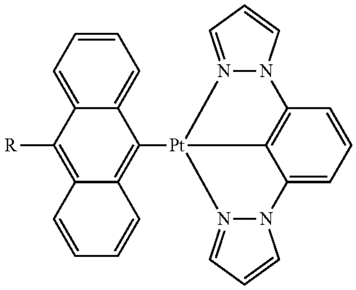
-continued
Compound 11G
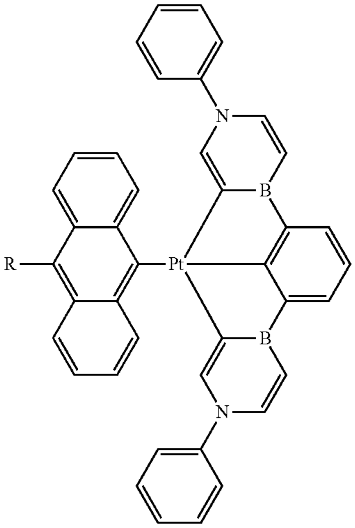
Compound 12G
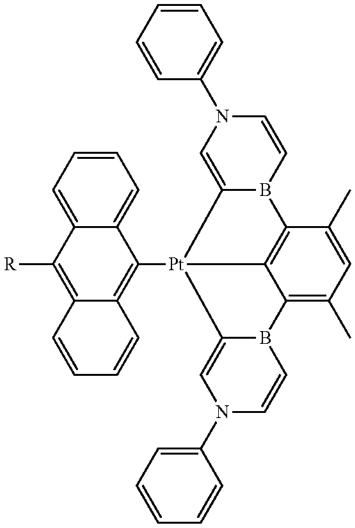
Compound 13G
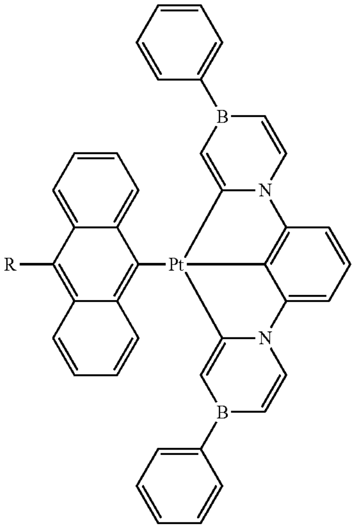

-continued
Compound 14G
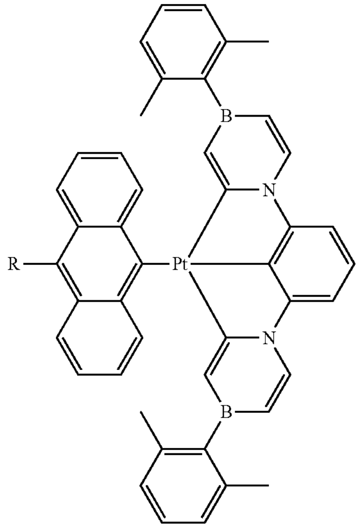
Compound 15G
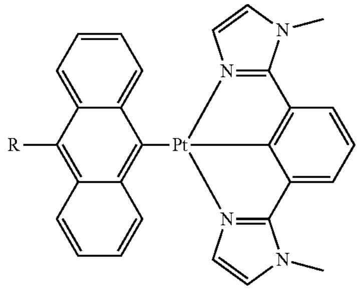
Compound 16G
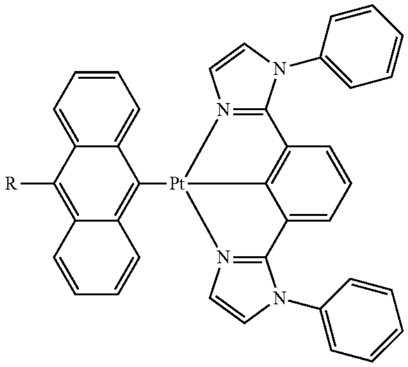
Compound 17G
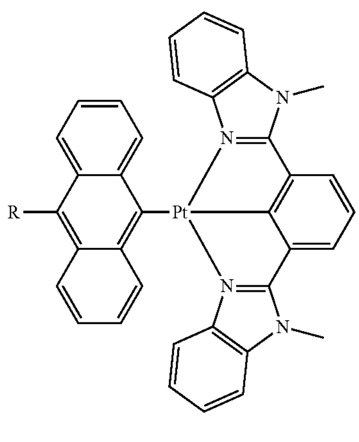
-continued
Compound 18G
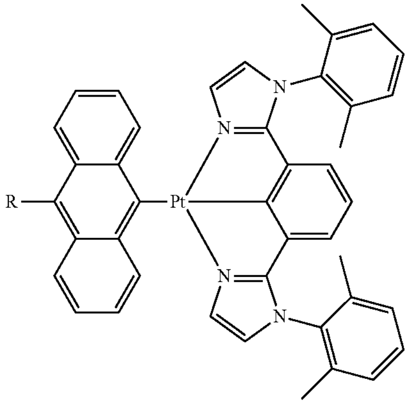
Compound 19G
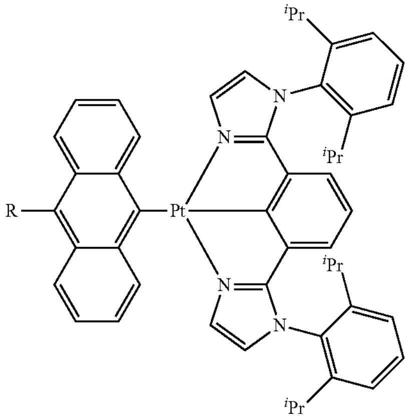
Compound 20G
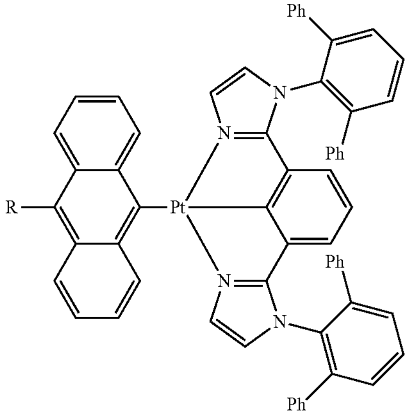
Compound 21G
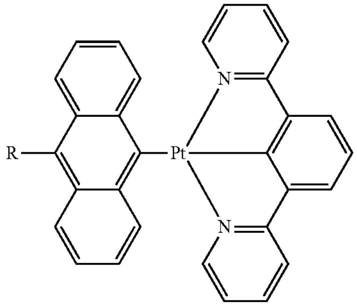

-continued
Compound 22G
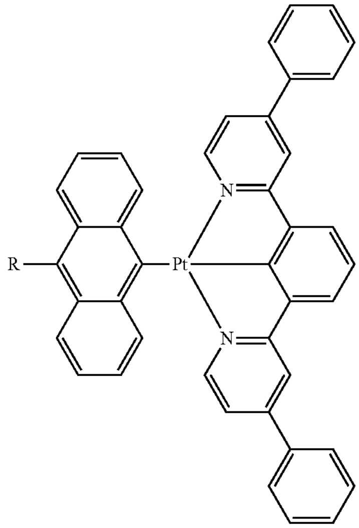
Compound 23G
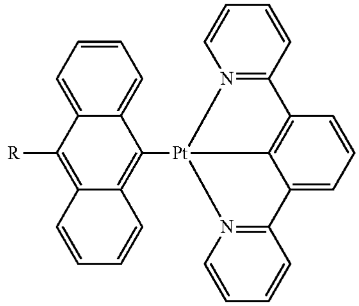
Compound 24G
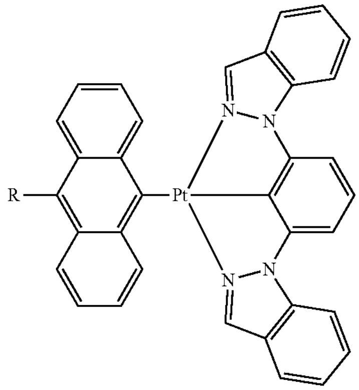
Compound 25G
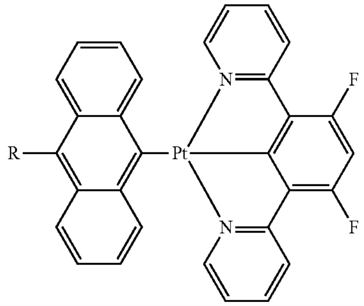
-continued
Compound 26G
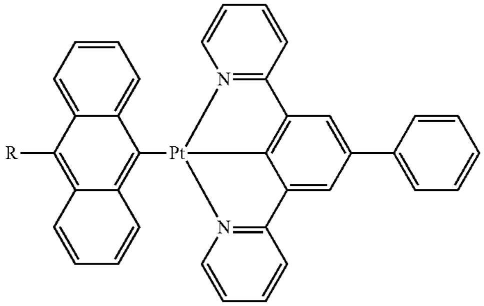
Compound 27G
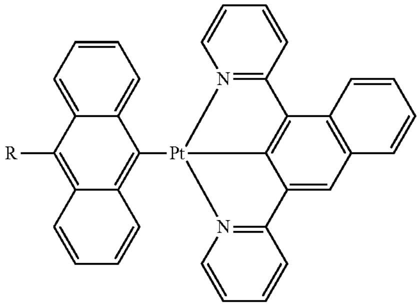
Compound 28G
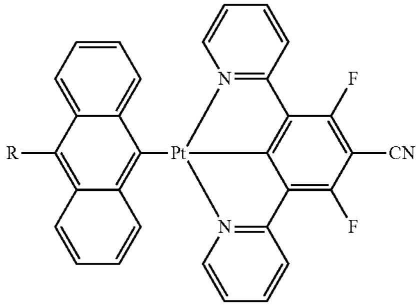
Compppund 29G
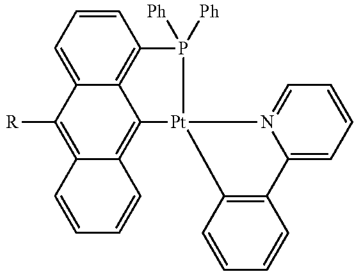
Compound 30G
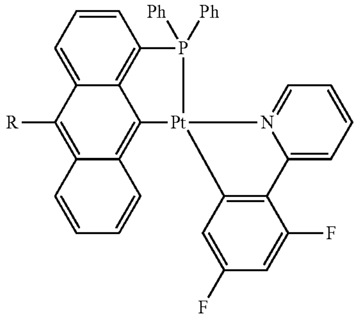

-continued
Compound 31G
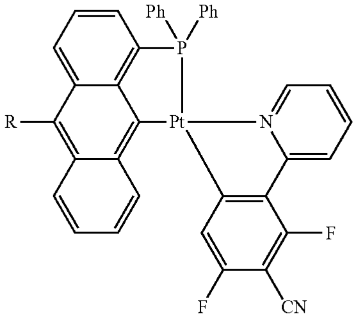
Compound 32G
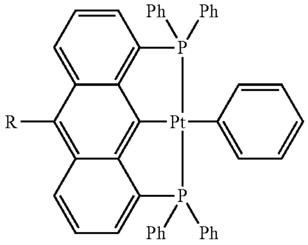
Compound 33G
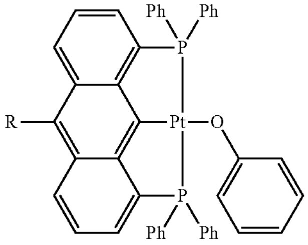
Compound 34G
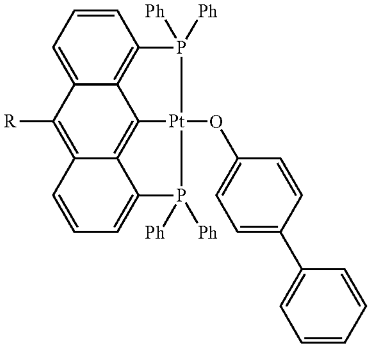
Compound 35G
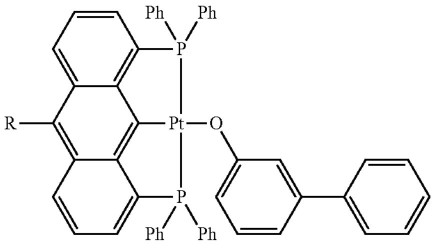
-continued
Compound 36G
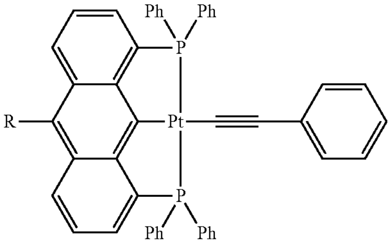
Compound 37G
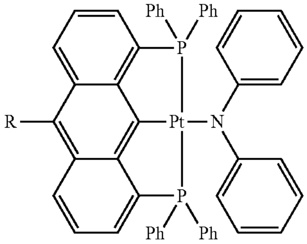
Compound 38G
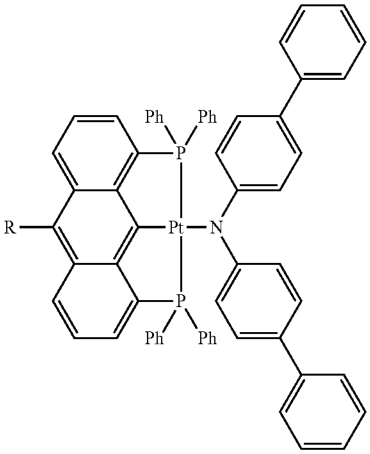
Compound 39G
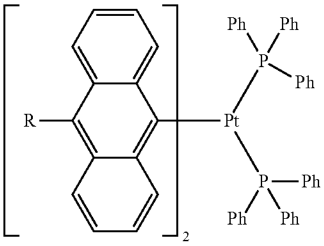
Compound 40G
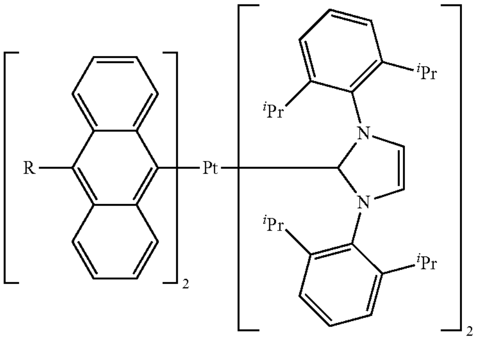

-continued
Compound 40G
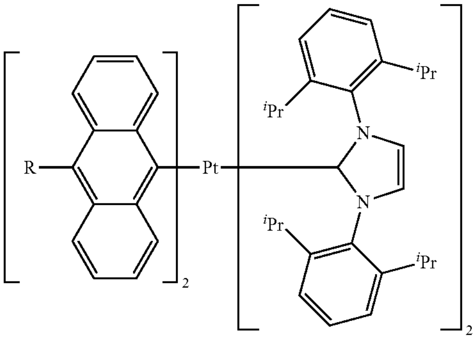
Compound 41G
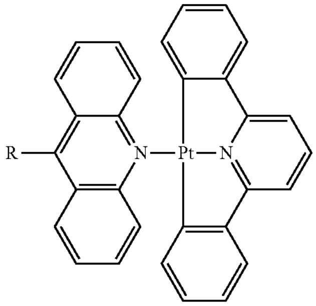
Compound 42G
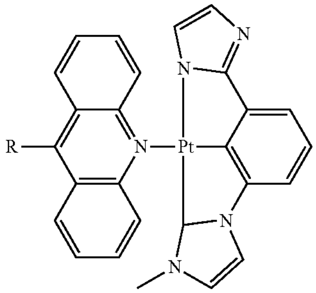
Compound 43G
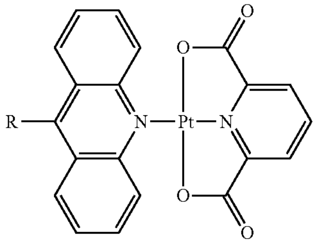
Compound 44G
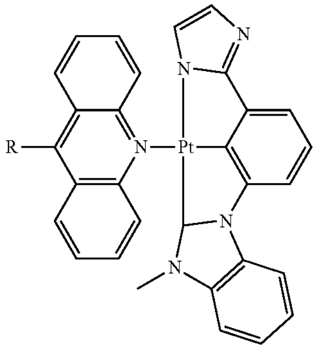
-continued
Compound 45G
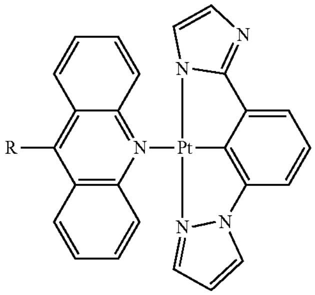
Compound 46G
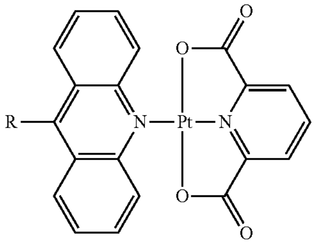
Compound 47G
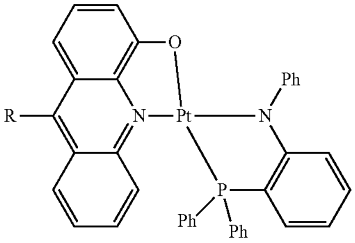
Compound 48G
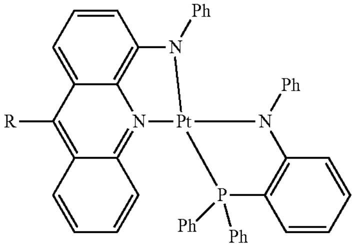
Compound 49G
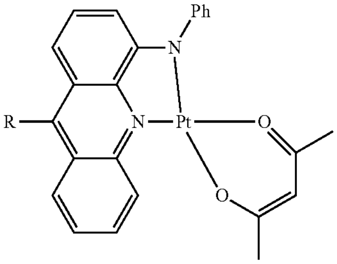
Compound 50G
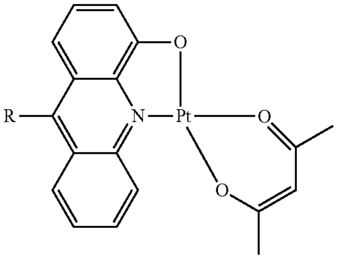

-continued
Compound 51G
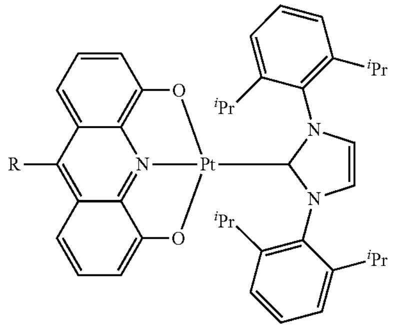
Compound 52G
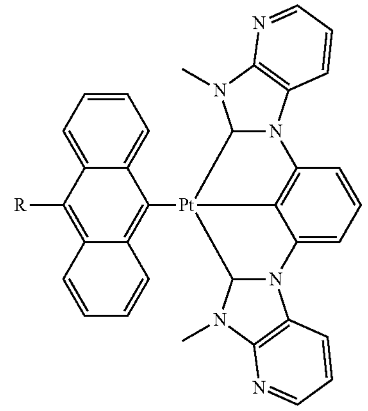
Compound 53G
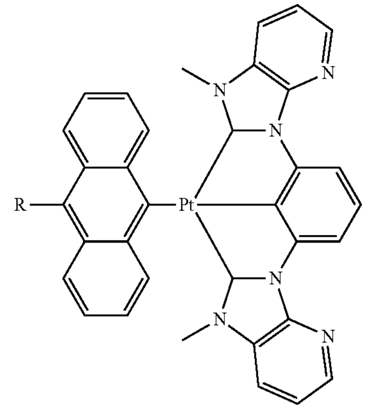
Compound 54G
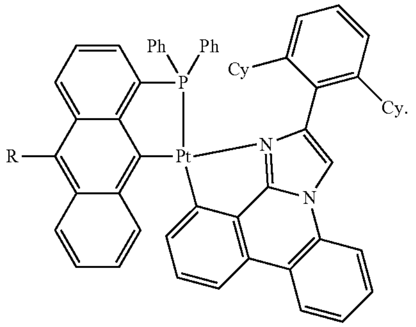
25. The compound of claim 24, wherein R is selected from the group consisting of:
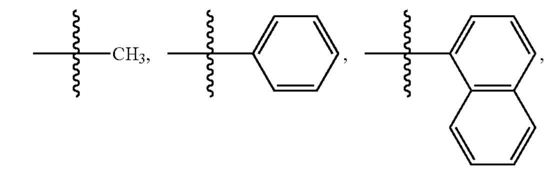
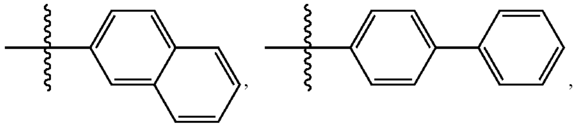
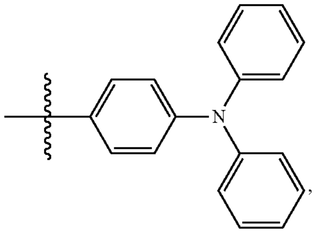
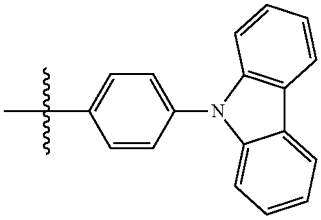
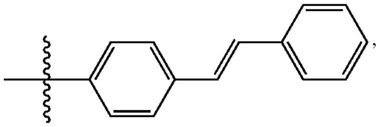
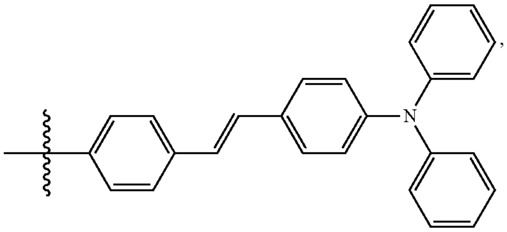
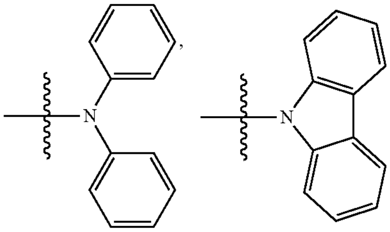
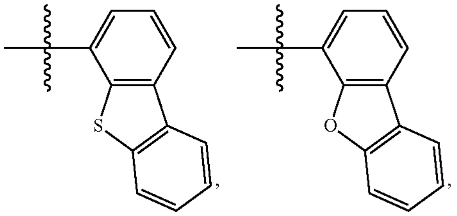

-continued
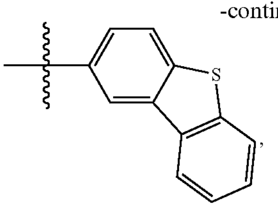
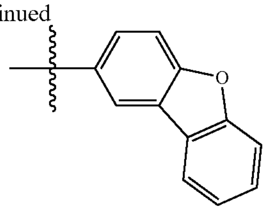
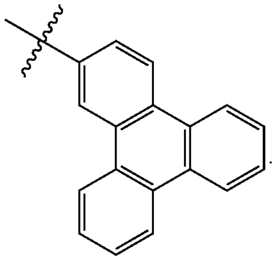
26. A first device comprising an organic light emitting device, comprising:
an anode;
a cathode; and
an organic layer, disposed between the anode and the cathode, further comprising a compound selected from the group consisting of:
Compound 1G
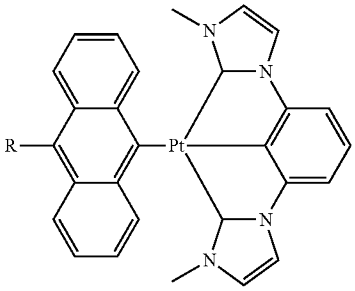
Compound 2G
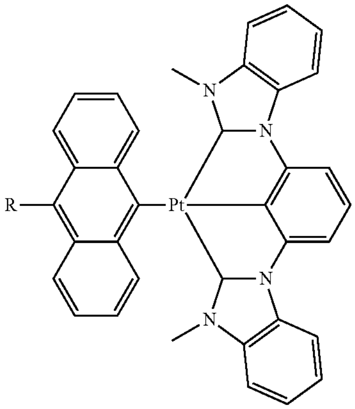
Compound 3G
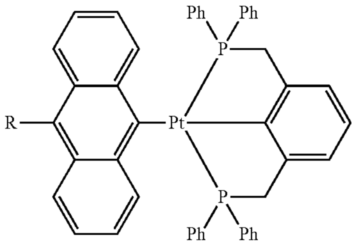
-continued
Compound 4G
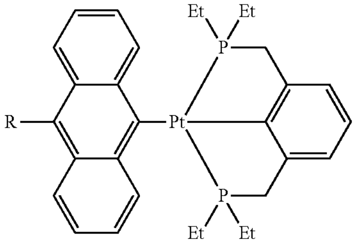
Compound 5G
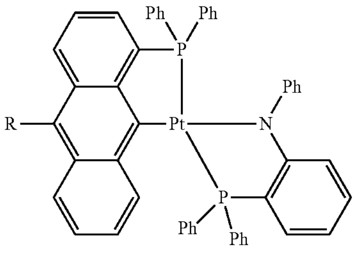
Compound 6G
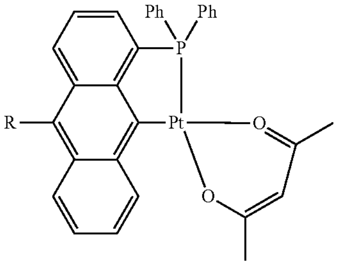
Compound 7G
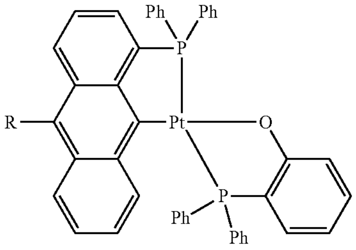
Compound 8G
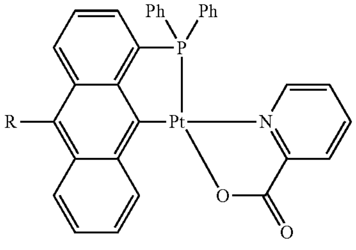
Compound 9G
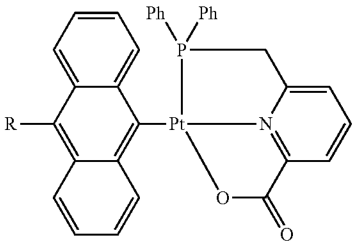

-continued
Compound 10G
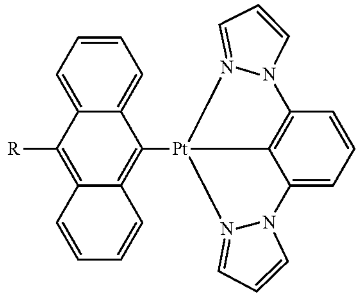
Compound 11G
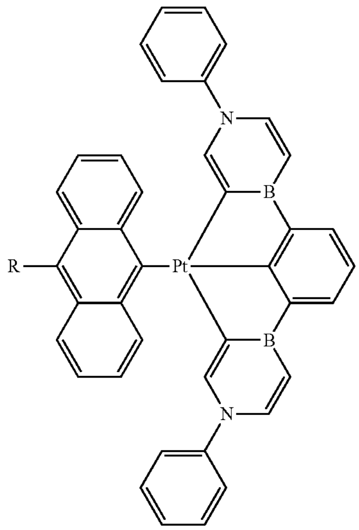
Compound 12G
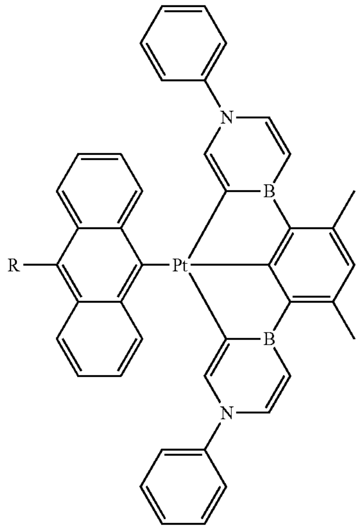
-continued
Compound 13G
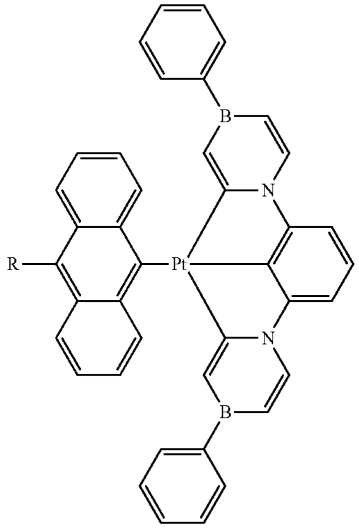
Compound 14G
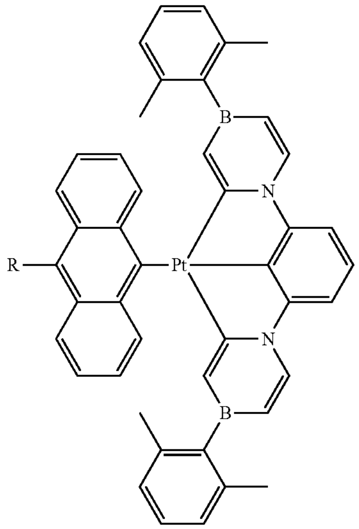
Compound 15G
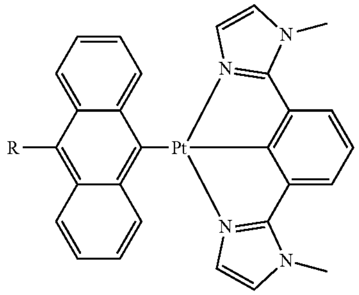

-continued
Compound 16G
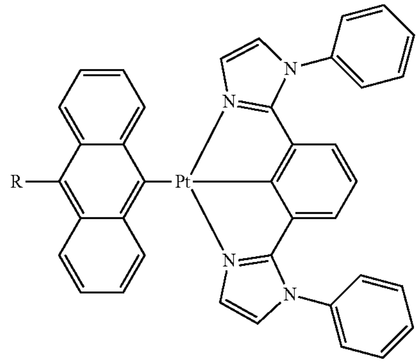
Compound 17G
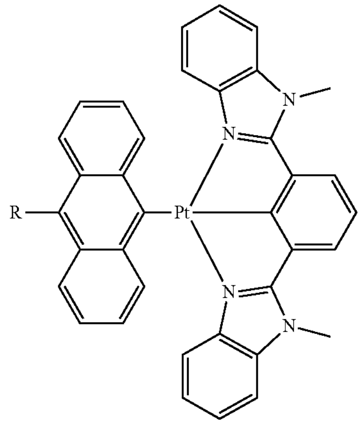
Compound 18G
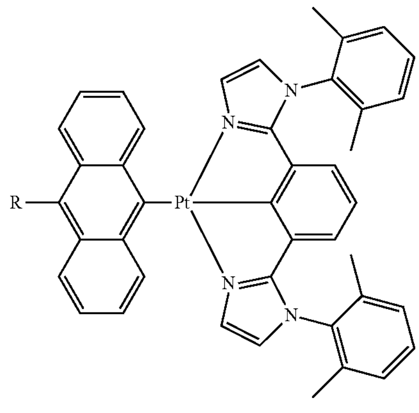
Compound 19G
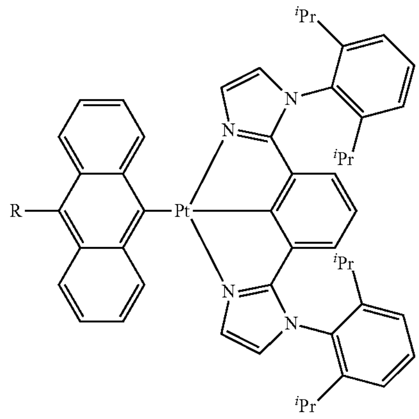
-continued
Compound 20G
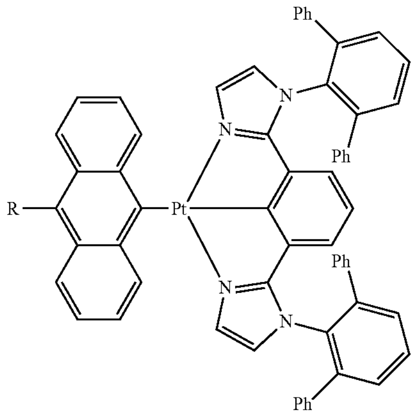
Compound 21G
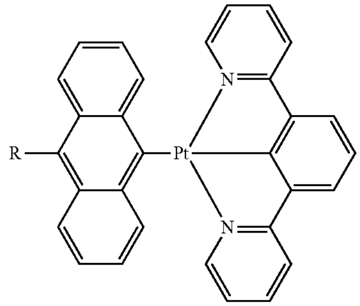
Compound 22G
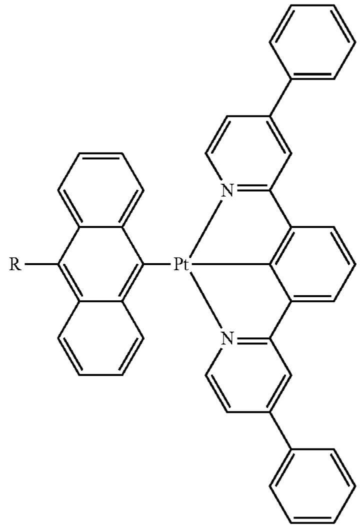
Compound 23G
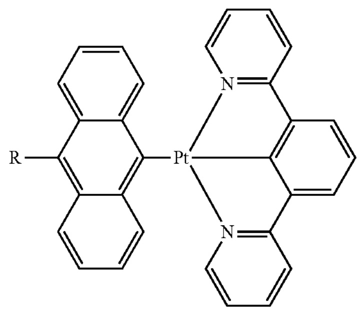

-continued
Compound 24G
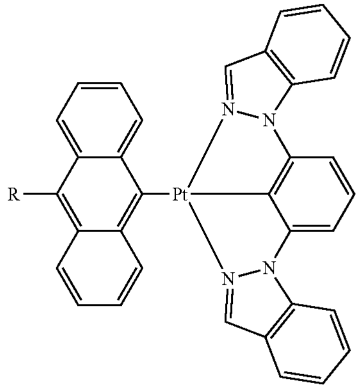
Compound 25G
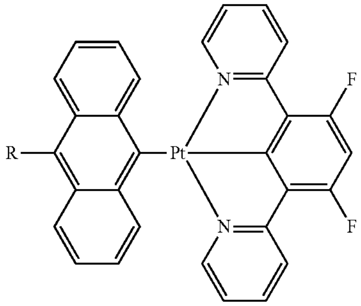
Compound 26G
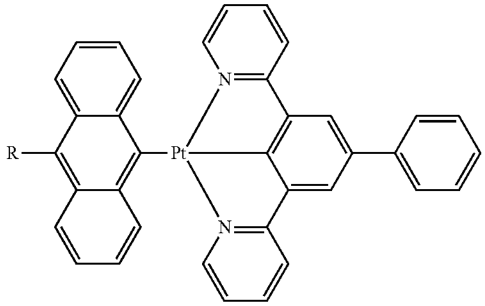
Compound 27G
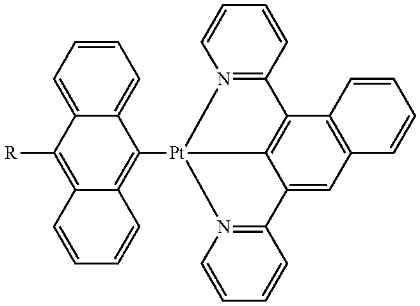
-continued
Compound 28G
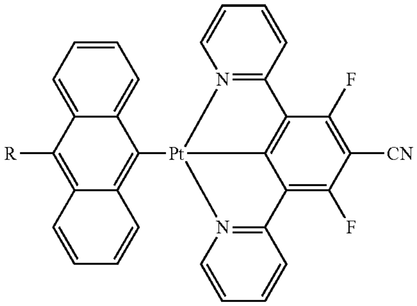
Compppund 29G
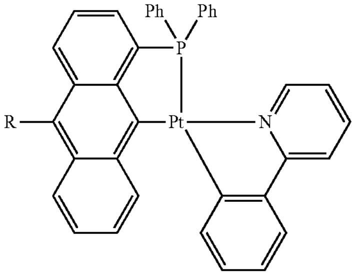
Compound 30G
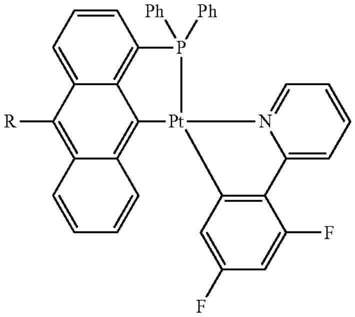
Compound 31G
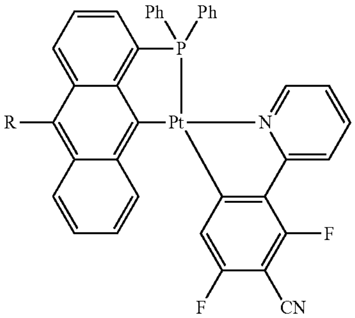
Compound 32G
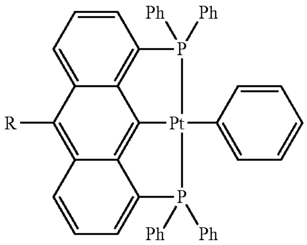

-continued
Compound 33G
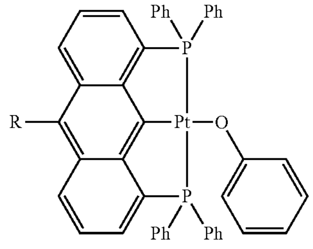
Compound 34G
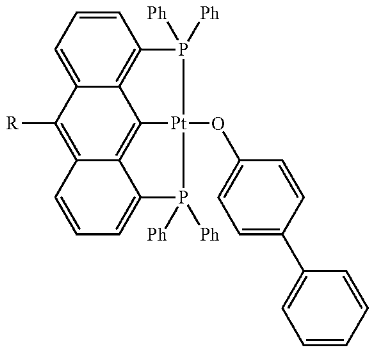
Compound 35G
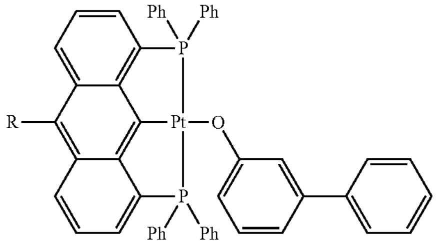
Compound 36G
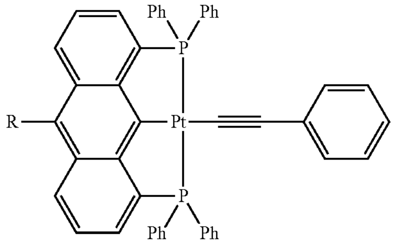
Compound 37G
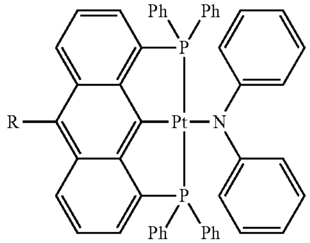
-continued
Compound 38G
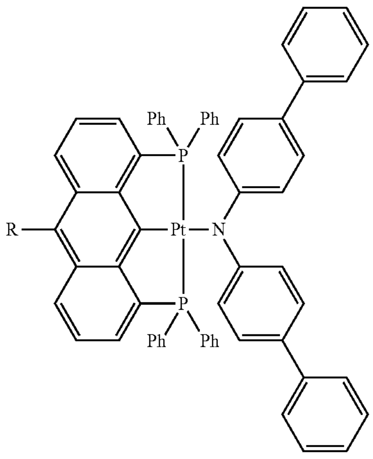
Compound 39G
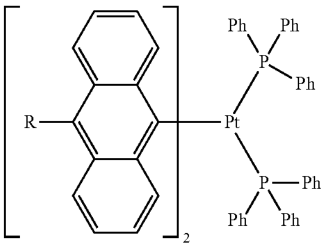
Compound 40G
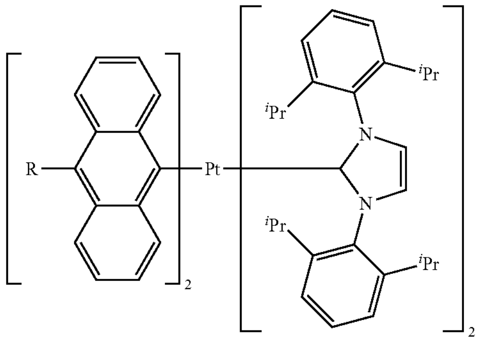
Compound 41G
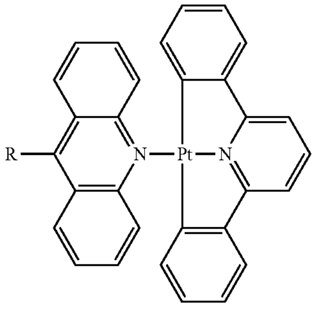

-continued
Compound 42G
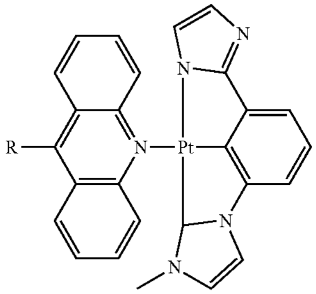
Compound 43G
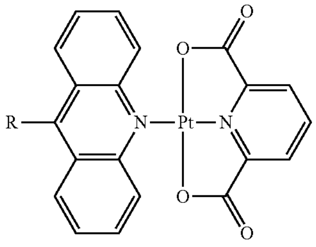
Compound 44G
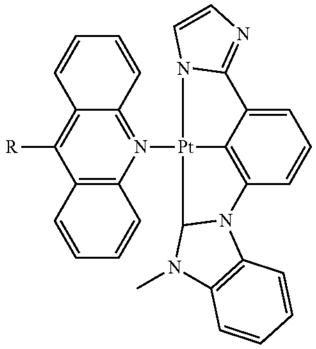
Compound 45G
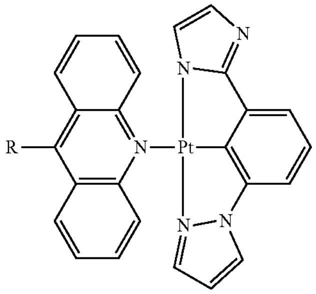
Compound 46G
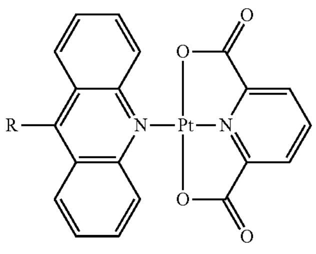
-continued
Compound 47G
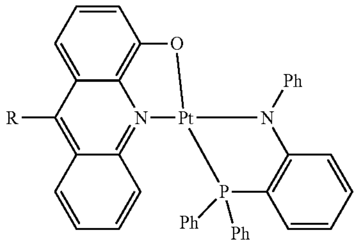
Compound 48G
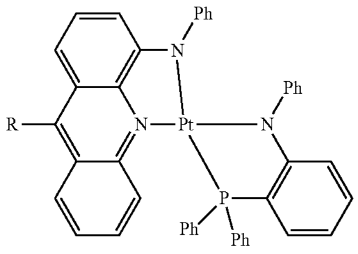
Compound 49G
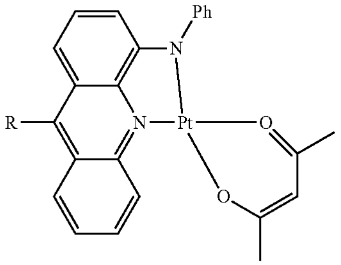
Compound 50G
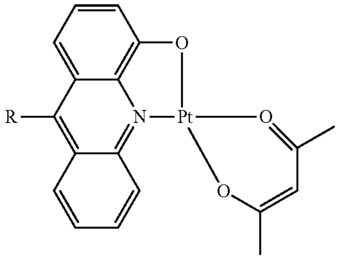
Compound 51G
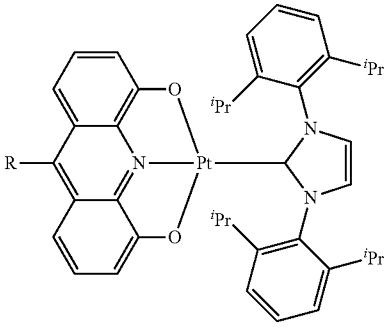

-continued
Compound 52G
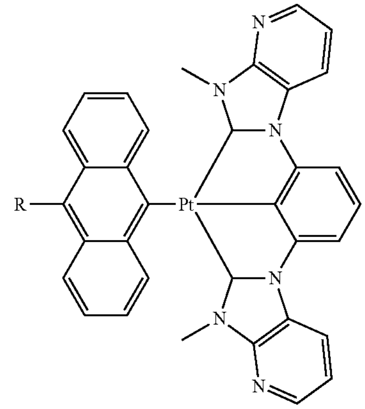
Compound 53G
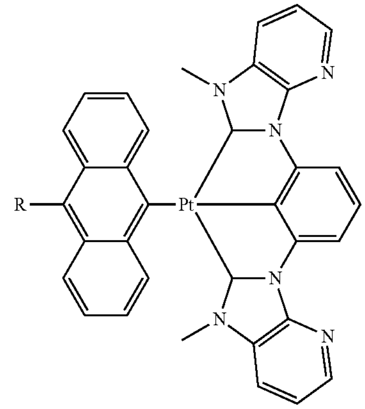
Compound 54G
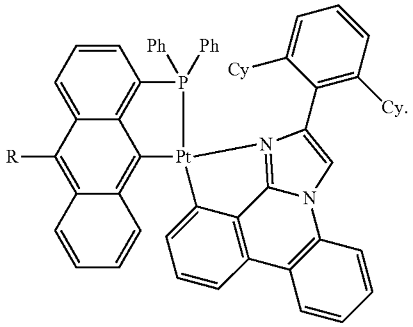
27. The first device of claim 26, wherein R is selected from the group consisting of:
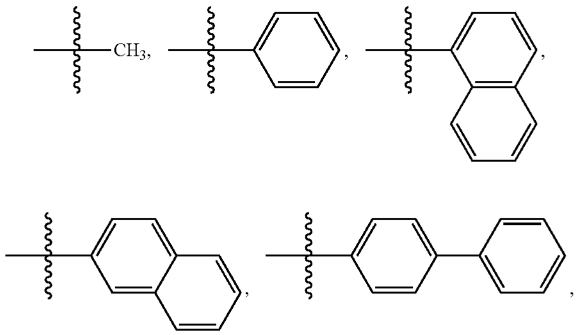
-continued
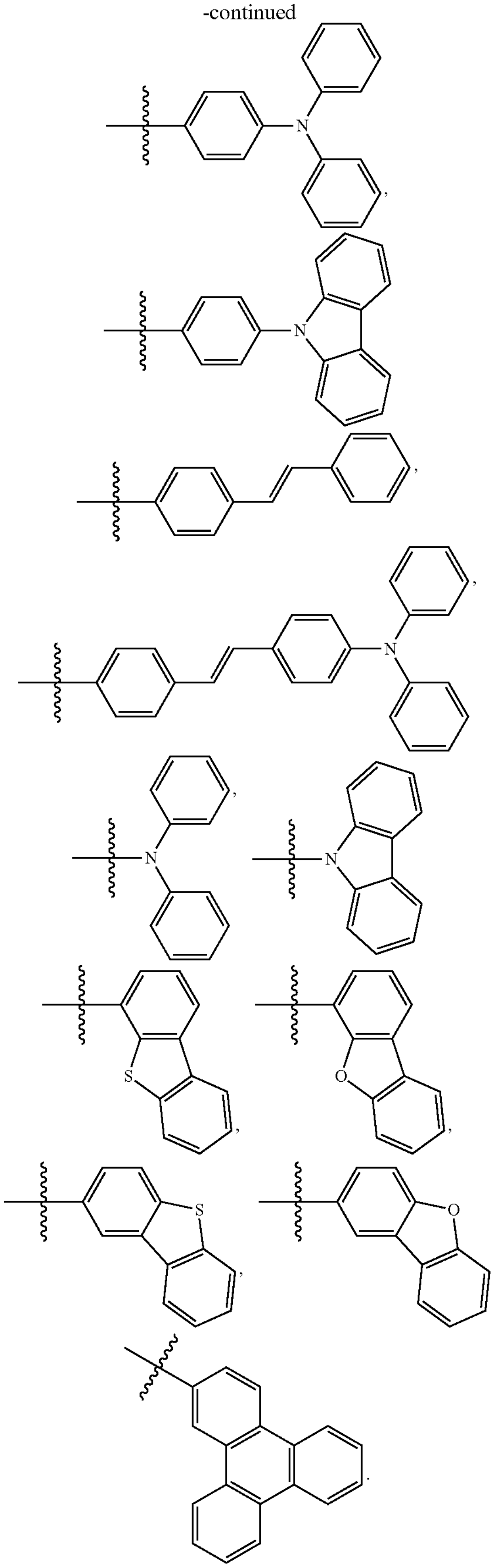
* * * * *